(12) United States Patent
Barbut et al.

(10) Patent No.: US 7,468,027 B2
(45) Date of Patent: Dec. 23, 2008

(54) PARTIAL AORTIC OCCLUSION DEVICES AND METHODS FOR CEREBRAL PERFUSION AUGMENTATION

(75) Inventors: Denise R. Barbut, New York, NY (US); Peter T. Keith, St. Paul, MN (US); Steven W. Berhow, St. Michael, MN (US); Jon P. St. Germain, Elk River, MN (US)

(73) Assignee: CoAxia, Inc., Maple Grove, MN (US)

( * ) Notice: Subject to any disclaimer, the term of this patent is extended or adjusted under 35 U.S.C. 154(b) by 321 days.

(21) Appl. No.: 11/256,549

(22) Filed: Oct. 21, 2005

(65) Prior Publication Data

US 2006/0047262 A1 Mar. 2, 2006

Related U.S. Application Data

(63) Continuation of application No. 10/052,688, filed on Jan. 18, 2002, now abandoned, which is a continuation of application No. 09/841,929, filed on Apr. 24, 2001, now Pat. No. 6,743,196, which is a continuation-in-part of application No. 09/528,969, filed on Mar. 20, 2000, now Pat. No. 6,565,552, which is a continuation-in-part of application No. 09/260,371, filed on Mar. 1, 1999, now Pat. No. 6,231,551.

(51) Int. Cl.
| | |
|---|---|
| A61N 1/362 | (2006.01) |
| A61M 29/00 | (2006.01) |
| A61M 31/00 | (2006.01) |
| A61M 37/00 | (2006.01) |

(52) U.S. Cl. .................. 600/18; 604/103.07

(58) Field of Classification Search ............ 604/22, 604/48, 500, 505, 506, 507, 509, 96.01, 101.01–102.05, 604/98.01, 103, 103.03, 103.07, 104, 158, 604/1, 164.01, 164.03, 264, 532, 236, 907, 604/914, 915, 919; 606/159, 192–194, 198, 606/200; 600/16–18; 128/898
See application file for complete search history.

(56) References Cited

U.S. PATENT DOCUMENTS 3,634,924 A 1/1972 Blake (Continued)

FOREIGN PATENT DOCUMENTS

WO WO 99/15227 4/1999

(Continued)

OTHER PUBLICATIONS

Simeone, F.A. Enhancement of Cerebral Blood Flow by Intermittent Aortic Occlusion. Cerebral Blood Flow and Intracranial Pressure. Proc. 5th int. Symp., Roma-Siena 1971, part II. Europ. Neurol. 8:142-144 (1972).*

(Continued)

*Primary Examiner*—Catherine S. Williams
(74) *Attorney, Agent, or Firm*—O'Melveny & Myers LLP

(57) ABSTRACT

Methods are provided for partial aortic obstruction for cerebral perfusion augmentation in patients suffering from global or focal cerebral ischemia. Alternatively, the methods can be used to partially obstruct aortic blood flow to condition the spinal cord to secrete neuroprotective agents prior to abdominal aortic aneurysm repair. Partial obstruction of a vessel can be accomplished by a device comprising an elongate catheter and a distally mounted expandable member. The expandable member may comprise one or two balloons. Other medical devices, such as an angioplasty, stent, or atherectomy catheter, can be inserted distal the expandable member to provide therapeutic intervention.

4 Claims, 48 Drawing Sheets

U.S. PATENT DOCUMENTS

| | | |
|---|---|---|
| 3,692,018 A | 9/1972 | Goetz |
| 3,720,200 A | 3/1973 | Laird |
| 4,368,739 A | 1/1983 | Nelson |
| 4,531,936 A | 7/1985 | Gordon |
| 4,600,015 A | 7/1986 | Evans |
| 4,601,706 A | 7/1986 | Aillon |
| 4,697,574 A | 10/1987 | Karcher |
| 4,701,160 A | 10/1987 | Lindsay |
| 4,712,566 A | 12/1987 | Hok |
| 4,723,549 A | 2/1988 | Wholey |
| 4,733,669 A | 3/1988 | Segal |
| 4,744,863 A | 5/1988 | Guckel |
| 4,777,951 A | 10/1988 | Cribier |
| 4,798,588 A | 1/1989 | Aillon |
| 4,853,669 A | 8/1989 | Guckel |
| 4,883,459 A | 11/1989 | Calderon |
| 4,941,473 A | 7/1990 | Tenerz |
| 4,996,082 A | 2/1991 | Guckel |
| 5,002,532 A | 3/1991 | Gaiser |
| 5,085,223 A | 2/1992 | Lars |
| 5,116,305 A * | 5/1992 | Milder et al. .............. 600/18 |
| 5,195,942 A | 3/1993 | Weil |
| 5,202,939 A | 4/1993 | Belleville |
| 5,216,032 A | 6/1993 | Manning |
| 5,221,258 A | 6/1993 | Shturman |
| 5,290,247 A | 3/1994 | Crittenden |
| 5,330,451 A | 7/1994 | Gabbay |
| 5,330,498 A | 7/1994 | Hill |
| 5,334,142 A | 8/1994 | Paradis |
| 5,392,117 A | 2/1995 | Belleville |
| 5,437,633 A | 8/1995 | Manning |
| 5,449,342 A | 9/1995 | Hirose |
| 5,458,574 A | 10/1995 | Machold |
| 5,486,192 A | 1/1996 | Walinsky |
| 5,505,701 A | 4/1996 | Anaya Fernandez de Lomana |
| 5,531,776 A | 7/1996 | Ward |
| 5,599,329 A | 2/1997 | Gabbay |
| 5,662,671 A | 9/1997 | Barbut |
| 5,678,570 A | 10/1997 | Manning |
| RE35,648 E | 11/1997 | Tenerz |
| 5,702,368 A | 12/1997 | Stevens |
| 5,711,754 A | 1/1998 | Miyata |
| 5,716,386 A | 2/1998 | Ward |
| 5,814,016 A | 9/1998 | Valley |
| 5,820,593 A | 10/1998 | Safar |
| 5,824,034 A | 10/1998 | Schmitt |
| 5,827,237 A | 10/1998 | Macoviak |
| 5,855,210 A | 1/1999 | Stermann |
| 5,891,012 A | 4/1999 | Downey |
| 6,010,522 A | 1/2000 | Barbut |
| 6,146,370 A | 11/2000 | Barbut |
| 6,161,547 A | 12/2000 | Barbut |
| 6,165,199 A | 12/2000 | Barbut |
| 6,190,304 B1 | 2/2001 | Downey |
| 6,231,551 B1 | 5/2001 | Barbut |
| 6,296,654 B1 | 10/2001 | Ward |
| 6,468,200 B1 * | 10/2002 | Fischi .............. 600/18 |
| 6,767,345 B2 | 7/2004 | St. Germain |

FOREIGN PATENT DOCUMENTS

| | | |
|---|---|---|
| WO | WO 9930765 | 6/1999 |
| WO | WO 9958174 | 11/1999 |

OTHER PUBLICATIONS

Simeone, et al. Experimental aigmentation of cerebral blood flow by internittent aortic occlusion. J. Neurosurgery, vol. 36, Jun. 1972, 700-713.*

Simeone, "Intra-Aortic Ballon Counterpulsation Augments Cerebral Blood Flow in a Canine Model of a Subarachnoid Hemorrhage-Induced Cerebrovasospasm," Neurosurgery 37(6):1233-1234 (1995).

Apostolides et al., "Intra-aortic Balloon Pump Counterpulsation in the Management of Concomitant Cerebral Vasospasm and Cardiac Failure after Subarachnoid Hemorrhage: Technical Case Report," *Neurosurgery*, 38:5, May 1996, pp. 1056-1060.

Bhayana et al., "Effects of Intraaortic Balloon Pumping on Organ Perfusion in Cardiogenic Shock," *Journal of Surgical Research*, 26(2):108-113 (1979).

Boston et al, "Differential Perfusion: A New Technique for Isolated Brain Cooling During Cardiopulmonary Bypass," *Ann. Thorac. Surg.* 69:1346-50 (2000).

Cheung et al, "Relationships Between Cerebral Blood Flow Velocities and Arterial Pressures During Intra-Aortic Counterpulsation," *Journal of Cardiothoracic and Vascular Anesthesia*, 12:1, pp. 51-57, Feb. 1998.

Edmunds, Jr. et al, "An Adjustable Pulmonary Arterial Band," *Trans. Amer. Soc. Artificial Internal Organs*, vol. XVII, 1972, pp. 217-223.

*Endovascular Angioplasty materials' catalog* (1999); 4 pages, including documents regarding (1) Scimed's Adanté PTCA balloon catheter, (2) Guidant's ACS RX Gemini™, (3) Nycomed Amersham's SEA*JET*® balloon catheter.

Nanas, et al., "Counterpulsation: Historical Background, Technical Improvements, Hemodynamic and Metabolic Effects," *Cardiology*, 84:156-157 (1994).

Nussbaum et al., "Intra-Aortic Balloon Counterpulsation Augments Cerebral Blood Flow in the Patient with Cerebral Vasospasm: a Xenon-Enhanced Computed Tomograph Study," *Neurosurgery*, 42(1):206-14 (1998).

Nussbaum et al., "Intra-Aortic Balloon Counterpulsation Augments Cerebral Blood Flow in a Canine Model of Subarachnoid Hemorrhage-Induced Cerebral Vasospasm," *Neurosurgery*, 36(4):879-86 (1995).

Sabiston, *Textbook of Surgery*, Sabiston, Ed., W.B. Saunders Company, publisher, 1981, pp. 2462-2463.

Tranmer et al., "Intra-aortic balloon counterpulsation: a treatment for ishcaemic stroke?" *Neurol. Res.*, 11(2):109-113 (1989).

Tranmer et al., Pulsatile Versus Nonpulsatile Blood Flow in the Treatment of Acute Cerebral Ischemia, *Neurosurgery*, 19(5):724-31 (1986).

* cited by examiner

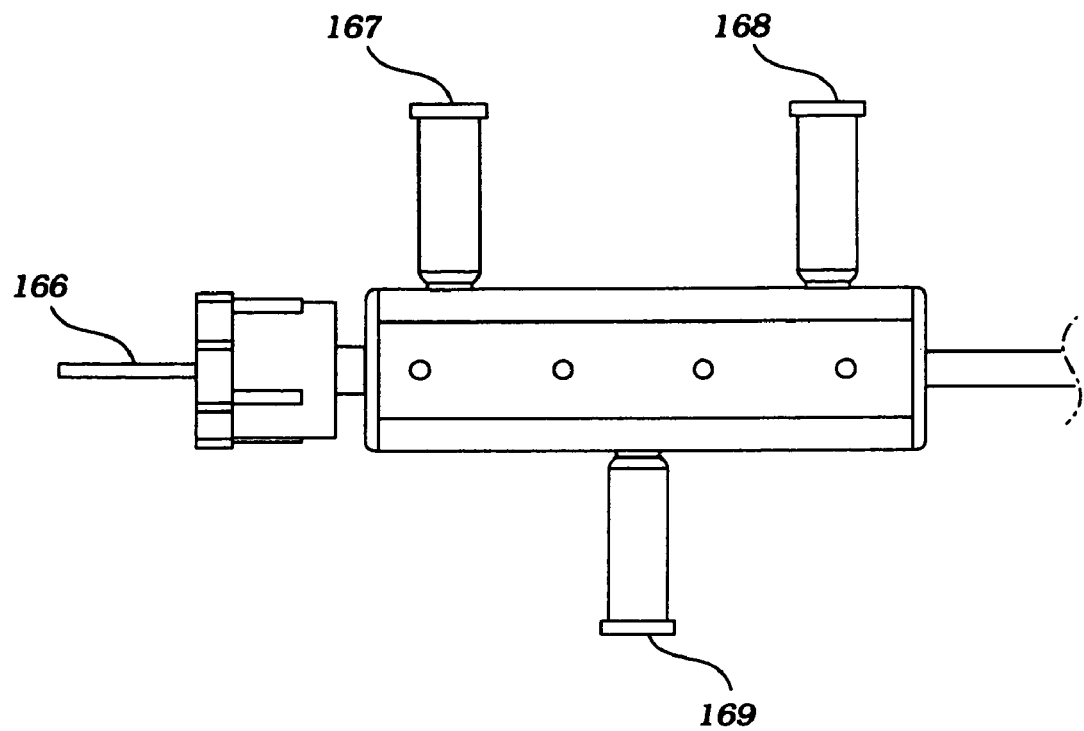
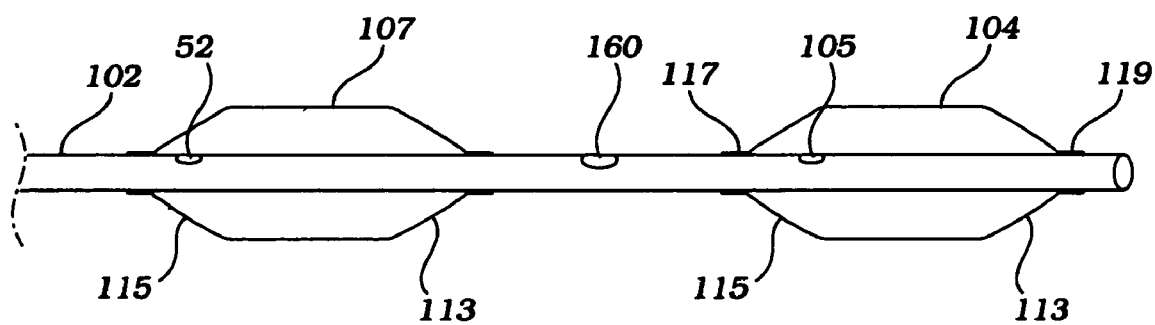
Fig. 6

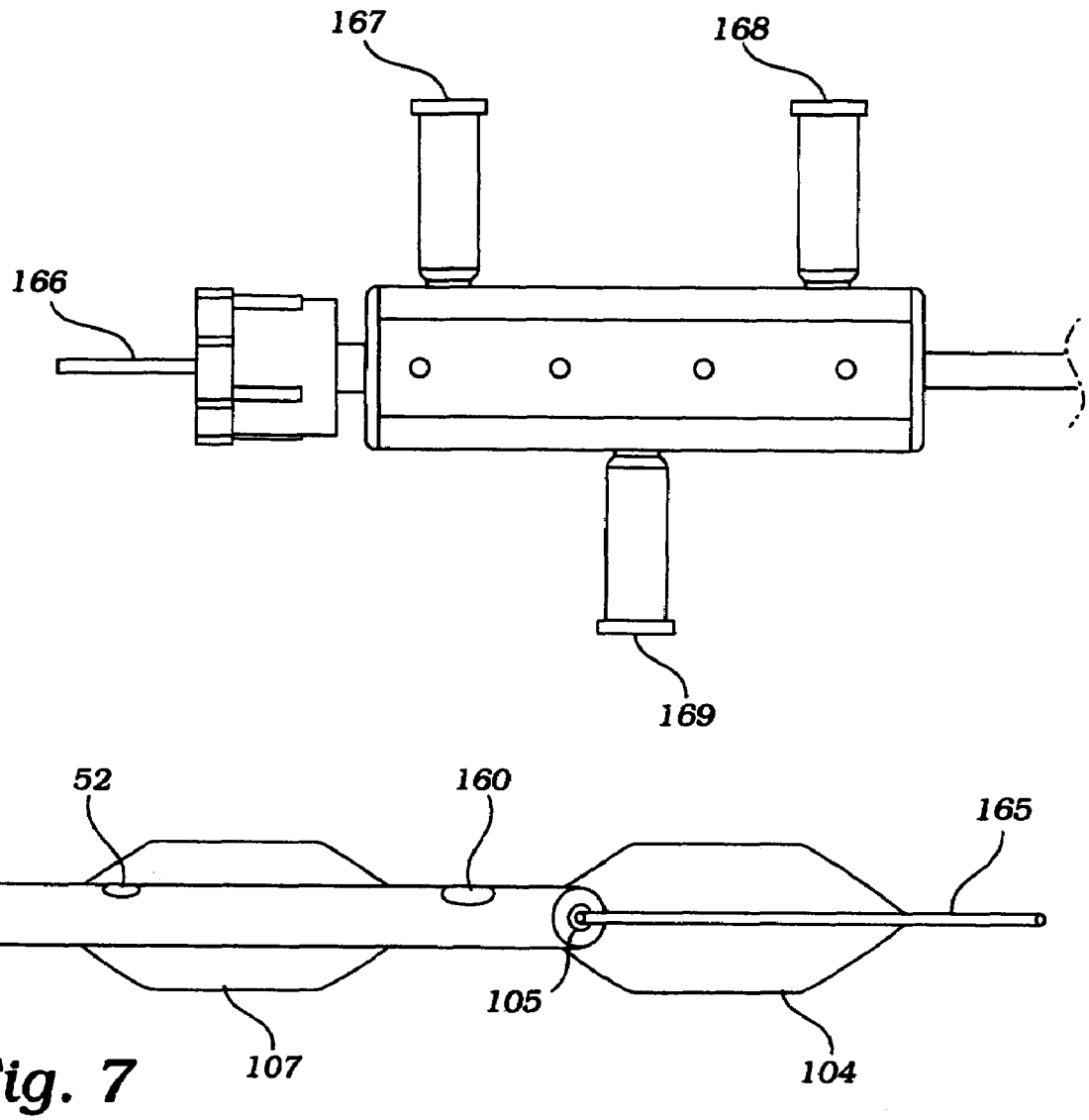
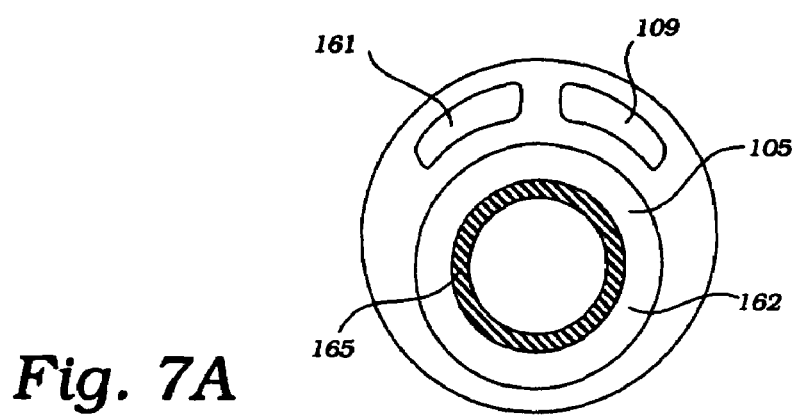
Fig. 7
Fig. 7A

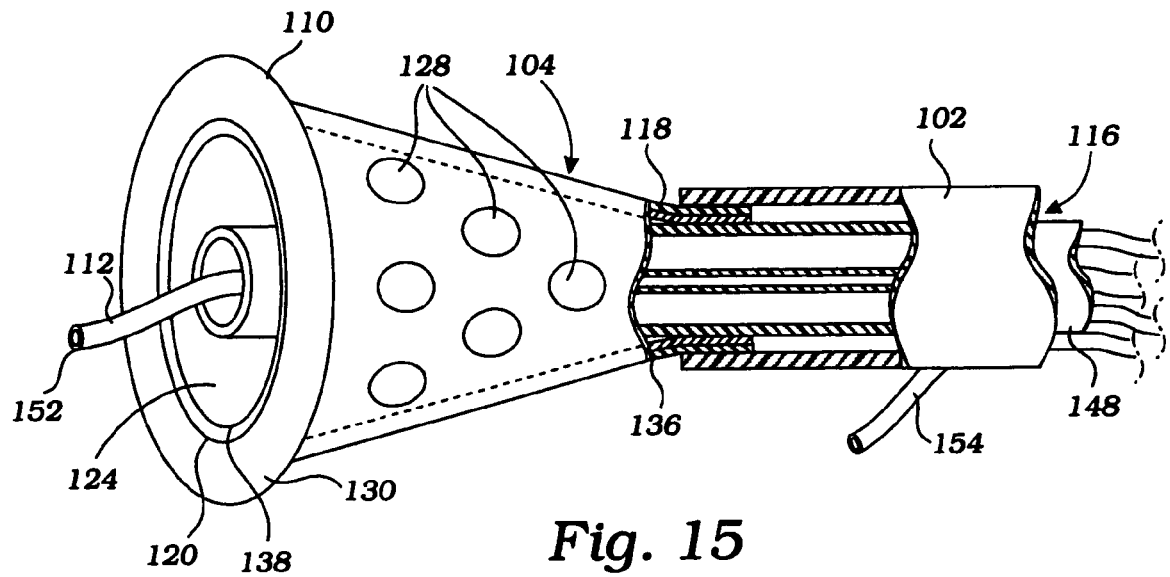
*Fig. 15*
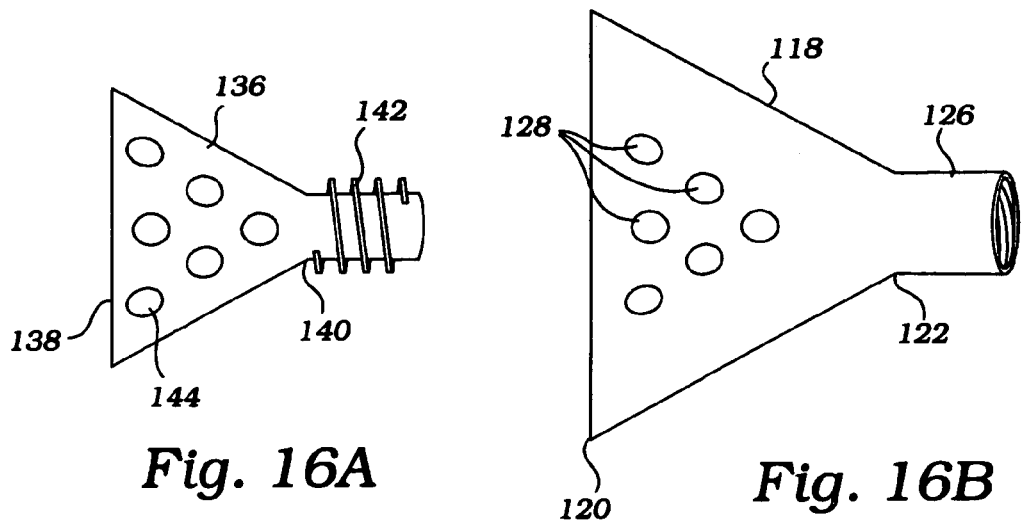
*Fig. 16A*  *Fig. 16B*

CAPILLARIES IN CORE WITHOUT AORTIC LIGATION

CAPILLARIES IN CORE WITH AORTIC LIGATION

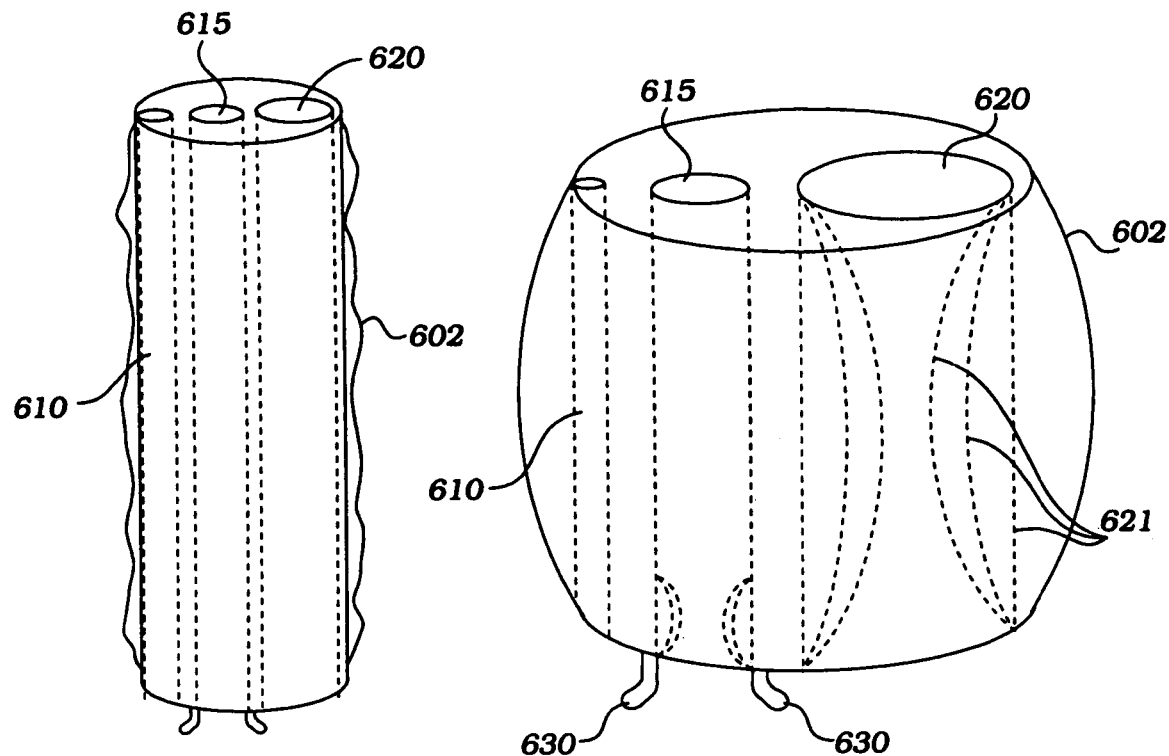
*Fig. 44E*  *Fig. 44F*
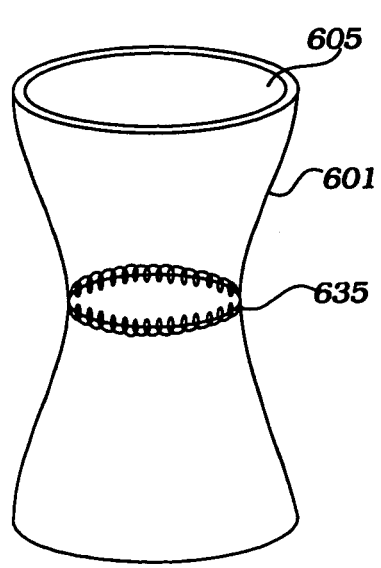
*Fig. 44G*  *Fig. 44H*

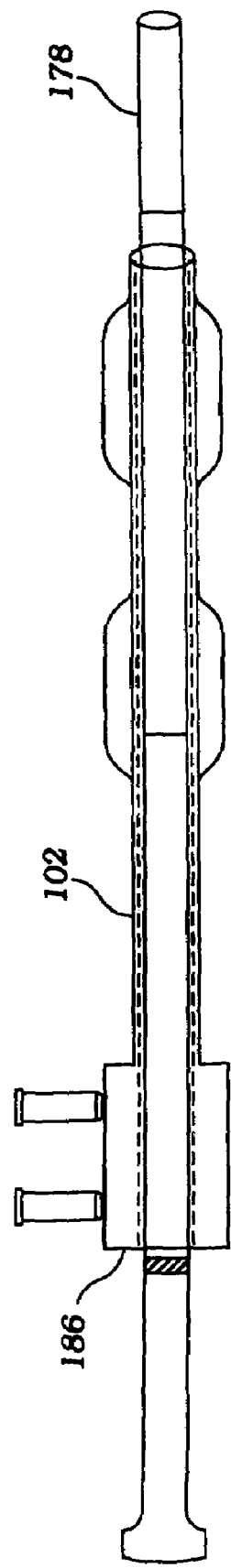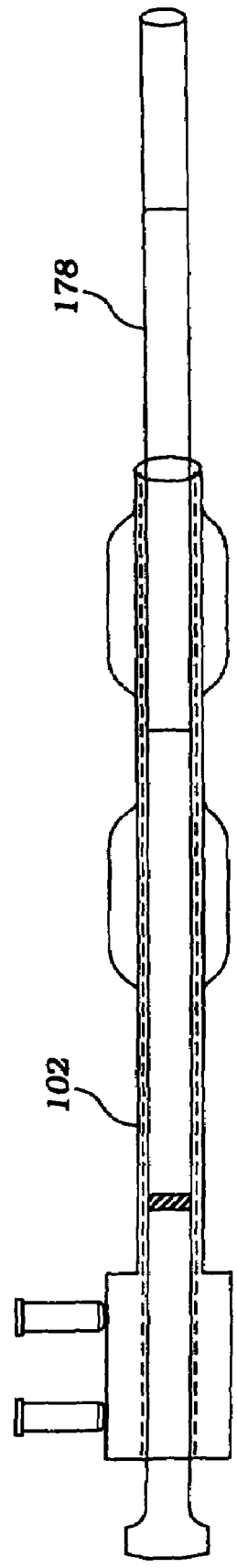

PARTIAL AORTIC OCCLUSION DEVICES AND METHODS FOR CEREBRAL PERFUSION AUGMENTATION

This is a continuation of U.S. application Ser. No. 10/052,688, filed Jan. 18, 2002, now abandoned which is a continuation of U.S. application Ser. No. 09/841,929, filed Apr. 24, 2001, now U.S. Pat. No. 6,743,196, which is a continuation-in-part of U.S. application Ser. No. 09/528,969, filed Mar. 20, 2000, now U.S. Pat. No. 6,565,552, which is a continuation-in-part of U.S. application Ser. No. 09/260,371, filed Mar. 1, 1999, now U.S. Pat. No. 6,231,551, all of which are incorporated herein by reference in their entirety.

FIELD OF THE INVENTION

The present invention relates generally to medical devices. More particularly, the invention relates to methods and devices for augmenting blood flow to a patient's vasculature. More particularly, the invention relates to apparatus and methods which provide partial obstruction ("coarctation") to aortic blood flow to augment cerebral perfusion in patients with global or focal ischemia. The devices and methods also provide mechanisms for continuous constriction and variable blood flow through the aorta.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Shock is the state in which failure of the circulatory system to maintain adequate cellular perfusion results in reduction of oxygen and nutrients to tissues. Within minutes of circulatory failure, tissues become ischemic, particularly in the heart and brain.

The two common forms of shock are cardiogenic shock, which results from severe depression of cardiac performance, and hemorrhagic shock, which results from trauma. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also cause cardiogenic shock by reducing cardiac output. Additional causes of cardiogenic shock include cardiac arrhythmia, such as ventricular fibrillation. Hemorrhagic shock is typically the result of penetrating injuries caused by, for example, traffic accidents and gunshot wounds. In this case, cardiac function is unimpaired and the cause of shock is blood loss.

Treatment of global cerebral ischemia involves treating the source of the systemic circulatory failure and ensuring adequate perfusion to the central nervous system. For example, treatment of cardiogenic shock due to prolonged cardiopulmonary bypass consists of cardiovascular support with the combination of inotropic agents such as dopamine, dobutamine, and intra-aortic balloon counterpulsation. Treatment of hemorrhagic shock consists of volume replacement and hemostasis. When these measures fail, supracoeceliac aortic clamping is used. Vasoconstrictors, such as norepinephrine, are also administered systemically to maintain systolic blood pressure (ideally above 80 mmHg). Unfortunately, these agents produce a pressure at the expense of flow, particularly blood flow to small vessels such as the renal arteries. The use of the vasoconstrictors is, therefore, associated with significant side effects, such as acute renal failure, congestive heart failure, and cardiac arrhythmias.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time due to the fact that some thrombi get absorbed into the circulation, or fragment and travel distally over a period of a few days. In June 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Vasospasm may be partially responsive to vasodilating agents. The newly developing field of neurovascular surgery, which involves placing minimally invasive devices within the carotid arteries to physically remove the offending lesion may provide a therapeutic option for these patients in the future, although this kind of manipulation may lead to vasospasm itself. Iatrogenic vasospasm and vasospasm caused by subarachnoid hemorrhage may respond to treatment with aortic constriction.

In both global and focal ischemia, patients develop neurologic deficits due to the reduction in cerebral blood flow. One treatment may include the use of devices to increase blood flow to the cerebral vasculature as the sole therapy. Alternatively, treatments include measures to increase blood flow to the cerebral vasculature to maintain viability of neural tissue, thereby increasing the length of time available for any adjunct interventional treatment and minimizing neurologic deficit while waiting for resolution of the ischemia. Augmenting blood flow to the cerebral vasculature is not only useful in treating occlusive or vasospastic cerebral ischemia, but may also be useful during interventional procedures, such as carotid angioplasty, stenting or endarterectomy, which might otherwise result in focal cerebral ischemia, and also cardiac procedures which may result in cerebral ischemia, such as cardiac catheterization, electrophysiologic studies, and angioplasty.

New devices and methods are thus needed for augmentation of cerebral blood flow in treating patients with either global or focal ischemia caused by reduced perfusion, thereby minimizing neurologic deficits.

SUMMARY OF THE INVENTION

In one embodiment, the invention provides vascular obstruction, occlusion, and/or constriction devices and methods for augmenting blood flow to a patient's cerebral vasculature, including the carotid and vertebral arteries. The terms obstruction, occlusion, and constriction are used interchangeably herein to refer to partial or complete blockage of a vessel, and to any of the devices that provide such blockage. The devices comprise an obstructing, occluding, or constricting mechanism distally mounted on a catheter for delivery to a vessel, such as the aorta. The obstructor, occluder, and/or constrictor is collapsed to facilitate insertion into and removal from the vessel, and expanded during use to at least partially obstruct blood flow.

In one embodiment, the devices comprise an elongate catheter having a proximal and a distal region. The catheter may also have a lumen extending between the proximal and distal regions. An expandable device, e.g., a balloon in certain cases, is carried at the distal region of the catheter. The catheter in certain embodiments may include a second expandable device carried at the distal region of the catheter, proximal the first expandable device. In certain embodiments, the catheter will also include blood pressure measuring capabilities distal and/or proximal the first and/or second (when present) expandable devices.

In use, the catheter having one expandable device is located in the descending aorta so that the expandable device is suprarenal or infrarenal. The expandable device is then expanded to partially or completely obstruct the descending aorta. Cerebral blood flow and cerebral blood pressure rises and is maintained at an increased level as desired. Cephalad blood pressure and/or cerebral blood flow may be monitored, and the expandable device adjusted as needed. Therapeutic instruments may be deployed through the lumen (when present) of the catheter to perform procedures cephalad.

In another embodiment, the constrictor, when expanded, has a maximum periphery that conforms to the inner wall of the vessel, thereby providing a sealed contact between it and the vessel wall. The constrictor typically has a blood conduit allowing blood flow from a location upstream to a location downstream. The devices further include a variable flow mechanism in operative association with the blood conduit, thereby allowing blood flow through the conduit to be adjusted and controlled. The devices can optionally include a manometer and/or pressure limiter to provide feedback to the variable flow mechanism for precise control of the upstream and downstream blood pressure.

In certain embodiments, the constrictor includes a second lumen for passage of other medical devices. Devices, such as an infusion, atherectomy, angioplasty, hypothermia catheters or devices (selective cerebral hypothermia with or without systemic hypothermia, and typically hypothermia will be combined with measures to increase perfusion to overcome the decreased cerebral blood flow caused by the hypothermia, such that hypothermia and coarctation are complimentary), or electrophysiologic study (EPS) catheter, can be introduced through the constrictor to insert in the vessel to provide therapeutic interventions at any site rostrally. Where cerebral cooling is desired in combination with coarctation, a cooling wire can be introduced through the constrictor to insert into a desired vessel. Alternatively, cooling catheter devices can be inserted through the constrictor to infuse cool blood selectively into one side of the brain. Devices and methods described in U.S. application Ser. No. 09/792,732, filed Feb. 23, 2001; Ser. No. 09/792,600, filed Feb. 23, 2001; Ser. No. 09/483,370, filed Jan. 14, 2000; Ser. No. 09/256,965, filed Feb. 24, 1999, now abandoned; 60/076,222, filed Feb. 25, 1998, now abandoned; 60/096,218, filed Aug. 12, 1998, now abandoned; and U.S. Pat. Nos. 6,161,547, 6,165,199, and 6,146,370, all incorporated herein by reference in their entirety, can be used for cooling or other procedures.

In another embodiment, the expandable constrictor comprises an outer conical shell and an inner conical shell. Each shell has an apex and an open base to receive blood flow. One or a plurality of ports traverses the walls of the two conical shells. Blood flows through the open base and through the ports. The inner shell can be rotated relative to the outer shell so that the ports align or misalign with the ports in the outer shell to allow variable blood flow past the occluder, thereby providing adjustable and controlled flow. The inner shell is rotated by a rotating mechanism, e.g., a torque cable disposed within the elongate tube and coupled to the inner shell. The constrictor can be expanded by, e.g., a resilient pre-shaped ring, graduated rings, or a beveled lip formed at the base of the shell, and collapsed by, e.g., pull wires distally affixed to the occluder or a guide sheath.

In another embodiment, the outer conical shell includes a plurality of resilient flaps, which are pivotally affixed to the base or the apex and can be displaced to variably control blood flow through the conduit. The flaps can be displaced by a plurality of pull wires affixed to the flaps.

In still another embodiment, the constrictor comprises a first cylindrical balloon mounted to a distal end of the catheter, and a second toroidal balloon disposed about the cylindrical balloon. The chamber of the first balloon communicates with an inflation lumen. Blood flow occurs through the cylindrical balloon and through the center of the toroidal balloon. The toroidal balloon is expanded by inflation through a second and independent inflation lumen to reduce blood flow through the cylindrical balloon. In this manner, the first balloon provides an inflatable sleeve and the second toroidal balloon provides variable control of blood flow through the sleeve. Other embodiments include an expandable sleeve (not a balloon) surrounded by a toroidal balloon, or a spring mechanism, for adjustably constricting the flow of blood through the cylindrical sleeve.

In use, the obstruction/occlusion/constriction devices described above are inserted into the descending aorta through an incision on a peripheral artery, such as the femoral, subclavian, axillary or radial artery, in a patient suffering from global or focal cerebral ischemia, typically stroke, shock or vasospasm, or during cardiac surgery (including any operation on the heart, with or without CPB), or during aortic surgery (during circulatory arrest, as for aortic arch surgery, repair of an abdominal aortic aneurysm, or thoracic aneurysm repair, to reduce perfusion and the amount of blood loss in the operating field). The devices can be introduced over a guide wire.

With assistance of transesophageal echocardiography (TEE), transthoracic echocardiography (TTE), intravascular ultrasound (IVUS), aortic arch cutaneous ultrasound, or angiogram, the constrictor is positioned downstream from the takeoff of the brachiocephalic artery and upstream from the renal arteries. When the constrictor is inserted in its preferred position, i.e., below the renal arteries, no visualization is necessary with any imaging equipment. The constrictor is expanded to at least partially obstruct blood flow in the aorta and maintained during systole, during diastole, or during systole and diastole. The constrictor preferably achieves continuous apposition to the wall of the vessel, resulting in reduced embolization. The pressure limiter, connected to the rotary unit and the pressure monitor, prevents the upstream and downstream blood pressure from exceeding, respectively, a set maximum and minimum pressure differential.

Flow rates can be varied within one cardiac cycle (e.g., 80% during systole, 20% during diastole, or 70% during systole, 30% during diastole), and every few cycles or seconds (e.g., 80% for 6 cycles, 20% for 2 cycles, or 70% for 5 cycles, 10% for 1 cycle). In certain cases it may be preferred to cycle between lesser and greater occlusion so that the brain does not autoregulate. This ensures constant and continued increased cerebral perfusion. In this manner, blood in the descending aorta is diverted to the cerebral vasculature, thereby increasing cerebral perfusion and minimizing neurological deficits. By selectively increasing cerebral blood flow, the use of systemically administered vasoconstrictors or inotropic agents to treat shock may be reduced or eliminated.

In another method, in patients anticipating a major cardiothoracic surgery, such as abdominal aortic aneurysm repair, the device is introduced and deployed approximately 24 hours prior to surgery, thereby inducing mild artificial spinal ischemia. This induces endogenous neuroprotective agents to be released by the spinal cord and/or brain in response to the ischemia, thereby protecting the tissue from ischemic insult of surgery. This technique is known as "conditioning." The devices are inserted into the descending aorta. To induce spinal ischemia, the constrictor is positioned downstream from the takeoff of the brachiocephalic artery and upstream from the renal artery and expanded to partially occlude blood flow in the aorta, resulting in reduction of blood flow to the spinal cord. A similar technique may be employed to condition the brain to stimulate production of neuroprotective agents. To induce cerebral ischemia, the constrictor is positioned upstream from the takeoff of the innominate artery, or between the innominate artery and the left common carotid artery.

It will be understood that there are many advantages in using the partial aortic occlusion devices and methods disclosed herein. For example, the devices can be used (1) to provide variable partial occlusion of a vessel; (2) to augment and maintain cerebral perfusion in patients suffering from global or focal ischemia; (3) to condition the brain or spinal cord to secrete neuroprotective agents prior to a major surgery which will necessitate reduced cerebral or spinal perfusion; (4) to prolong the therapeutic window in global or focal ischemia; (5) to accommodate other medical devices, such as an atherectomy catheter; (6) prophylactically by an interventional radiologist, neuroradiologist, or cardiologist in an angiogram or fluoroscopy suite; (7) for prevention of cerebral ischemia in patients undergoing procedures, such as coronary catheterization or surgery, where cardiac output might fall as a result of arrhythmia, myocardial infarction or failure; (8) to treat shock, thereby eliminating or reducing the use of systemic vasoconstrictors; (9) to prevent hypotensive neurologic damage during carotid stenting, and (10) to rescue vasospasm induced by hemorrhage or interventional procedures.

BRIEF DESCRIPTION OF THE DRAWINGS

FIG. 6 illustrates another embodiment of the devices constructed according to the present invention for providing partial occlusion of a vessel.

FIG. 7 illustrates another embodiment of the devices constructed according to the present invention for providing partial occlusion of a vessel.

FIG. 7A illustrates a cross-sectional view of the device shown in FIG. 7.

FIG. 15 illustrates a constrictor of the device depicted in FIG. 14.

FIG. 16A illustrates an outer conical shell employed in the constrictor of FIG. 15.

FIG. 16B illustrates an inner conical shell employed in the constrictor of FIG. 15.

FIG. 44E depicts another embodiment of the constrictor having a manometer and lumen allowing passage of other devices.

FIG. 44F depicts the inflated constrictor of FIG. 44E.

FIG. 44G depicts another embodiment of the constrictor having a spring mechanism constricting its lumen.

FIG. 44H depicts the constrictor of FIG. 44G with the spring mechanism relaxed.

FIG. 48E depicts the guiding catheter of FIG. 48D disposed within the catheter of FIG. 48B.

FIG. 48F depicts adjustment of the guiding catheter within the catheter of FIG. 48B.

DETAILED DESCRIPTION OF THE PREFERRED EMBODIMENTS

The devices and methods disclosed herein are most useful in treating patients suffering from global cerebral ischemia due to systemic circulatory failure, and focal cerebral ischemia due to thromboembolic occlusion of the cerebral vasculature. However, it will be understood that the devices and methods can be used in other medical conditions, such as hypertension and spinal cord conditioning.

Figure 1:
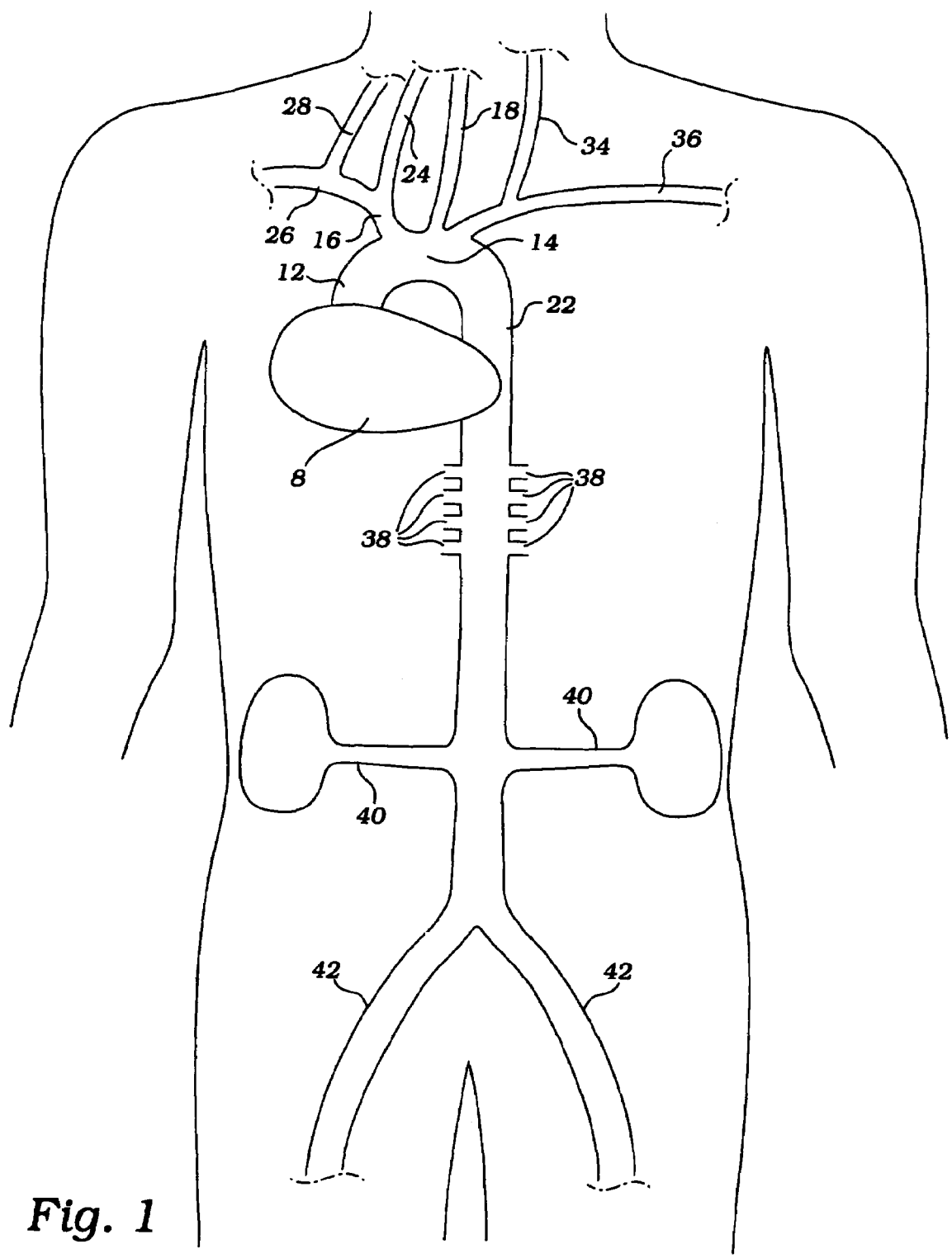
FIG. 1 illustrates a patient's systemic arterial circulation relevant to the present invention.

Systemic arterial circulation relevant to the methods of the present invention is described in FIG. 1. During systole, oxygenated blood leaving heart 8 enters aorta 10, which includes ascending aorta 12, aortic arch 14, and descending aorta 22. The aortic arch gives rise to brachiocephalic trunk 16, left common carotid artery 18, and left subclavian artery 20. The brachiocephalic trunk branches into right common carotid artery 24 and right subclavian artery 26. The right and left subclavian arteries, respectively, give rise to right vertebral artery 28 and left vertebral artery 34. The descending aorta gives rise to a multitude of arteries, including lumbar (i.e., spinal) arteries 38, which perfuse the spinal cord, renal arteries 40, which perfuse the kidneys, and femoral arteries 42, which perfuse the lower extremities.

Figure 2A:
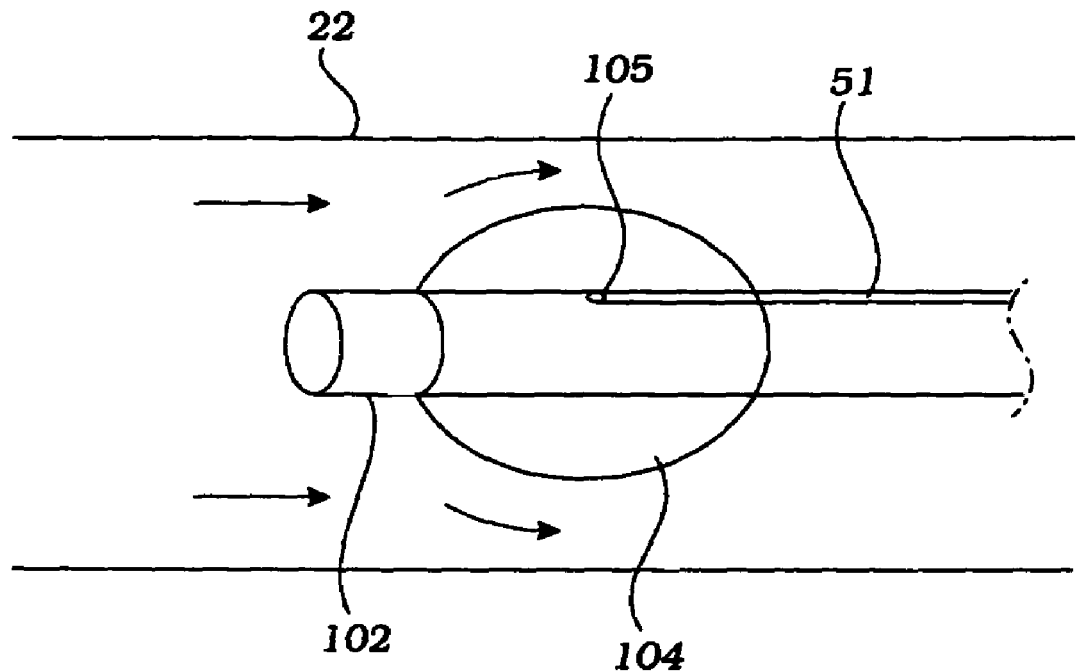
FIG. 2A illustrates an embodiment of the devices constructed according to the present invention for providing partial occlusion of a vessel.

In one embodiment as shown in FIG. 2A, the obstruction device comprises elongate catheter 102 having a proximal end and a distal end, shown here positioned within descending aorta 22. The distal end has expandable member 104, e.g., a balloon. Balloon 104 communicates with inflation lumen 51 through port 105. In another embodiment, depicted in FIG. 2B, ports 111 are included in the surface of catheter 102 to allow blood flow through the distal end of catheter 102 to pass through the catheter downstream constrictor 104.

Figure 3:
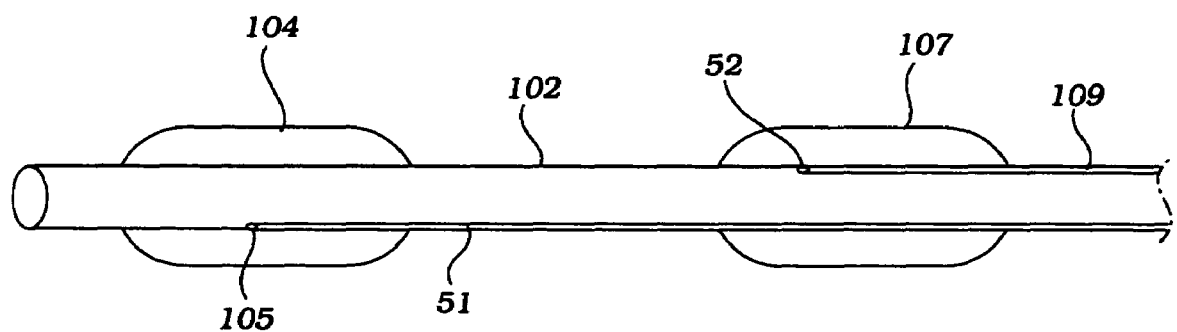
FIG. 3 illustrates another embodiment of devices having two expandable members according to the present invention for providing partial occlusion of a vessel.

In another embodiment as shown in FIG. 3, the obstruction device comprises elongate catheter 102 having a proximal end and a distal end. The distal end has first expandable member 104 and second expandable member 107, e.g., balloons, and in certain embodiments elongate balloons, mounted and spaced from each other. Balloon 104 communicates with inflation lumen 51 through port 105. Balloon 107 communicates with inflation lumen 109 through port 52. Balloon 104 and balloon 107 are thus able to be inflated independent of each other, or, in other embodiments, are inflated from a common inflation lumen.

It will be understood that the constrictor, when implemented as a balloon, can be of any shape that is suitable for use in the aorta. An elongate balloon (e.g., balloons 104 and 107 in FIG. 3), elliptical or sausage-shape, is particularly desirable because this shape is more stable within rapidly flowing blood. A spherical balloon (although useful in the disclosed inventions) will tend to rock within the aorta, and rotate and bend the catheter to which it is affixed. The use of an elongate balloon, however, reduces the rocking and rotating within the vessel because this shape effectively eliminates one of the degrees of freedom present with a spherical balloon.

In certain embodiments, the catheter is equipped with blood pressure measuring capabilities proximal and/or distal to one or each expandable member. The blood pressure measuring capabilities may comprise a manometer mounted on the catheter or a channel communicating with a transducer at the proximal end and a port at the distal end of the catheter. Blood pressure measuring may also be accomplished by use of a fiber optic in vivo pressure transducer as described in U.S. Pat. Nos. 5,392,117 and 5,202,939, incorporated herein by reference in their entirety, or a Radi pressure wire as described in U.S. Pat. Nos. Re 35,648; 5,085,223; 4,712,566; 4,941,473; 4,744,863; 4,853,669; and 4,996,082, incorporated herein by reference in their entirety.

Figure 4:
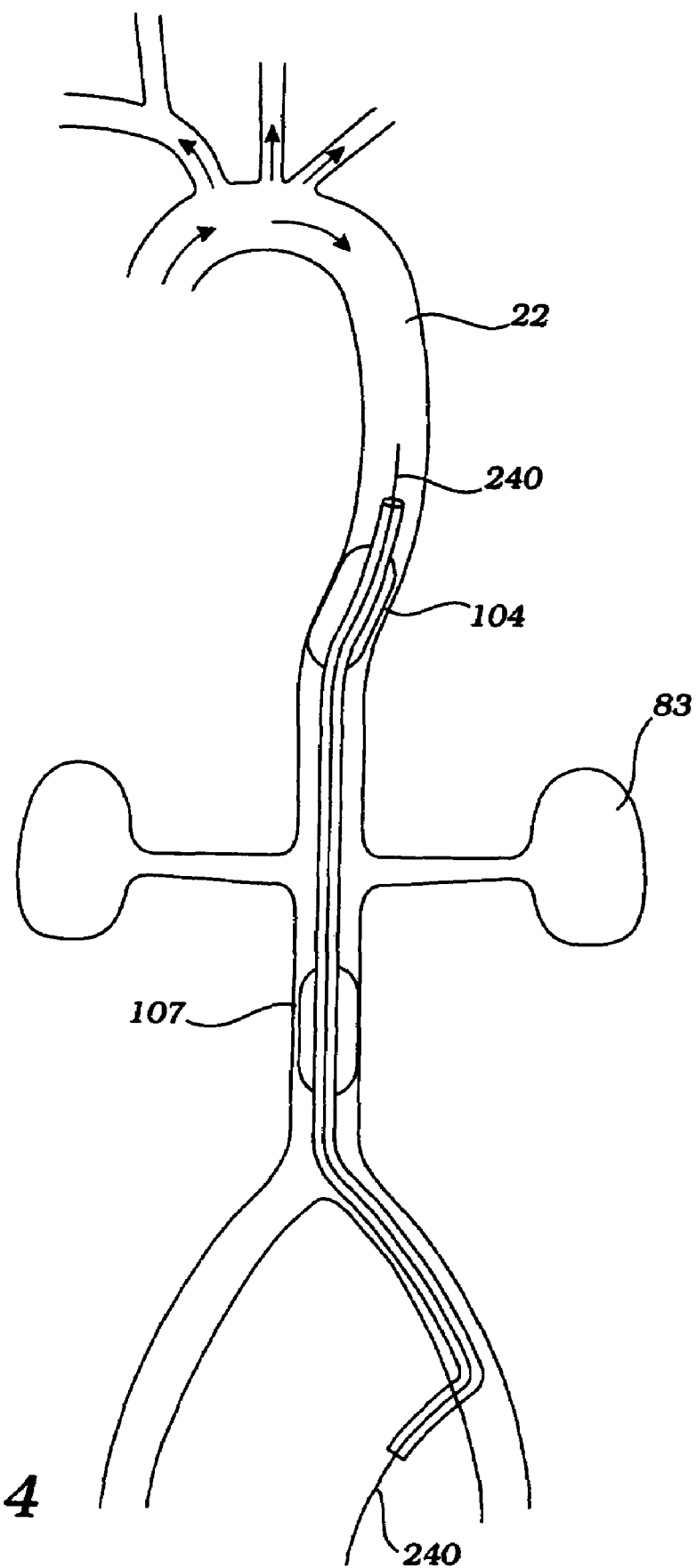
FIG. 4 illustrates deployment of the device shown in FIG. 3 in the aorta.

In use, the catheter is inserted in descending aorta 22, and advanced to a position such that first constricting balloon 104 is upstream of the renal arteries, celiac, and superior mesenteric artery, and second constricting balloon 107 is downstream of these arteries as shown in FIG. 4. A two-balloon device permits independent regulation and adjustment of cerebral blood flow and renal blood flow. Thus, downstream balloon 107 is first expanded while measuring cerebral blood flow until the desired increase over baseline is obtained, e.g., 100% increase. This step will also result in increased blood flow to the renal and superior mesenteric arteries. If this step results in inadequate cerebral blood flow increase, then upstream balloon 104 is expanded to constrict upstream the renal and superior mesenteric arteries until the desired cerebral blood flow increase is obtained. Deployment of the upstream constrictor reduces blood flow to the renal and superior mesenteric arteries as compared with blood flow before deployment of the upstream constrictor.

If the deployment of downstream balloon 107 produces the desired increase in cerebral blood flow, then upstream balloon 104 will not be deployed in certain procedures. In other procedures, upstream balloon 104 is deployed so that constriction in downstream balloon 107 can be reduced, thereby partially relieving the renal and superior mesenteric arteries of increased flow. It will be understood that inclusion of a balloon downstream is desirable in some cases because it allows the surgeon to maintain renal blood flow at or above baseline while increasing blood flow to the brain. It may also be desirable to achieve constriction predominantly downstream of the renal arteries that supply blood to kidneys 83 to avoid obstructing the spinal arteries that lie upstream the renal arteries. It may also be desirable to have both balloons 107 and 104 partially inflated, rather than either balloon fully inflated, to avoid blocking arteries that branch from the aorta.

Alternatively, both balloons may be inflated simultaneously until a desired increase in cerebral flow is achieved. In this manner, flow to the renal arteries will be maintained at substantially the initial baseline flow. If it is desired to further adjust renal blood flow while maintaining the cerebral blood flow and/or increase in proximal aortic pressure, the two balloons can be simultaneously adjusted, e.g., one increased and one decreased, until the desired renal blood flow is achieved.

It will be understood that one objective for the devices and methods described herein is to increase cerebral blood flow during stroke. Expansion of a constrictor in the descending aorta produces increased blood pressure upstream of the constrictor, which leads to increased cerebral blood flow. A small change in upstream blood pressure, however, can produce a very large change in cerebral blood flow. Cerebral blood flow can be measured by transcranial Doppler, functional MRI, CT scan, PET scan, SPECT scan, or any other suitable technique known in the art. In certain procedures therefore, it may be desirable to adjust expansion of constrictors 107 and/or 104 in response to measured cerebral blood flow increase instead of, or in addition to, measured blood pressure increase upstream the constrictor and/or measured blood pressure decrease downstream the constrictor. If cerebral blood flow is to be used as a measure, then a baseline blood flow is measured before expansion of the constrictor. The constrictor is then expanded while measuring blood flow until a desired increase in flow is achieved. Typically, the desired increase will be 50 percent or greater, 60 percent or greater, 70 percent or greater, 80 percent or greater, 90 percent or greater, or 100 percent or greater of baseline blood flow, or more than 100 percent. The amount of increased cerebral blood flow will depend on a variety of factors including the patient's baseline blood pressure. If the blood pressure is excessively high, it may be desirable to achieve a smaller increase in cerebral blood flow, so as not to increase the proximal aortic pressure to an excessive value. In addition, the increase in the amount of pressure or flow achievable will also depend on baseline conditions. For example, the lower the baseline aortic pressure, the larger the pressure increase achievable.

Figure 5A:
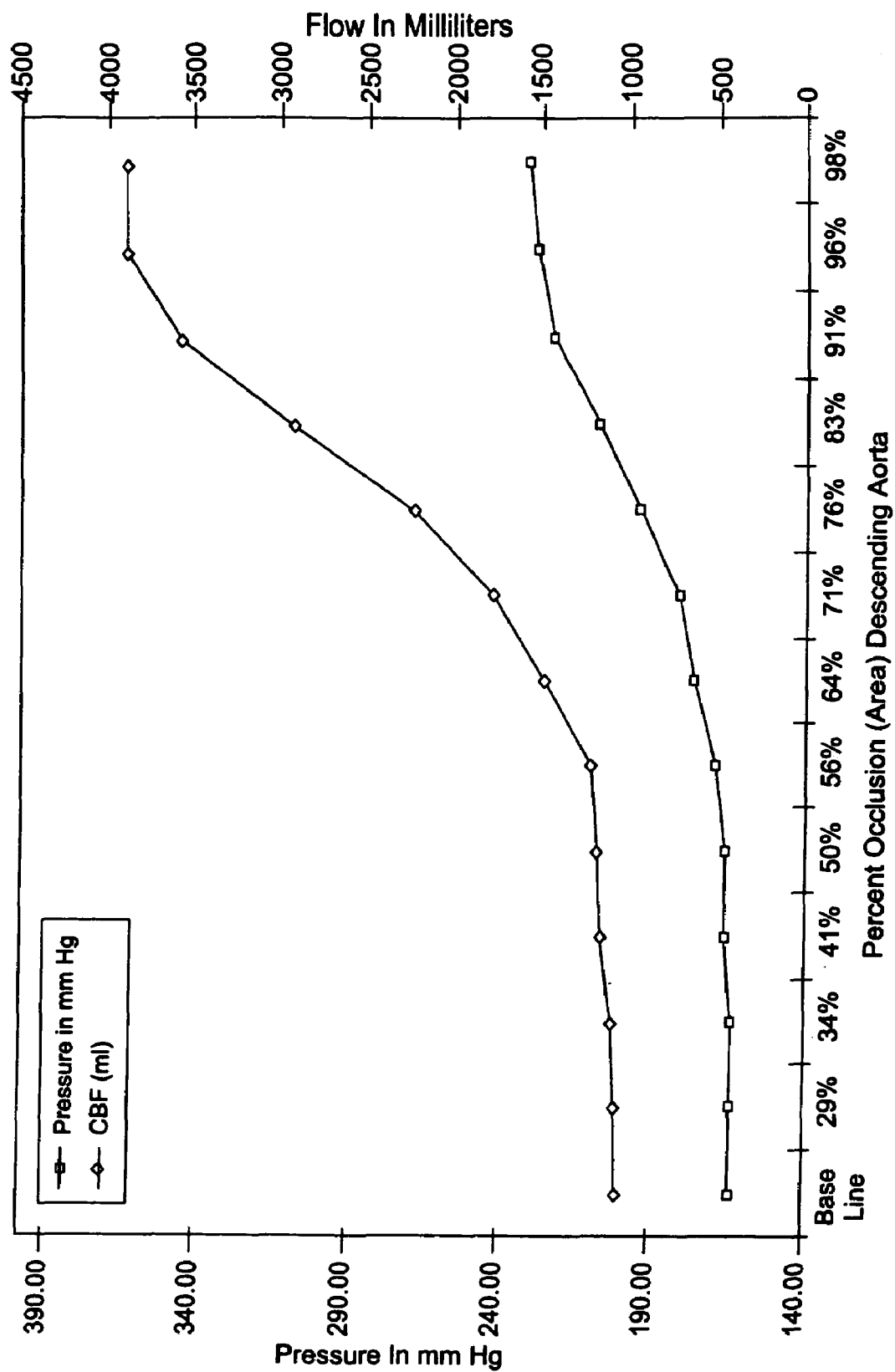
FIG. 5A illustrates a plot of cerebral blood flow and aortic pressure v. percent occlusion area of the descending aorta during use of the devices constructed according to the present invention for providing partial occlusion of a vessel.

A plot of upstream aortic blood pressure and cerebral blood flow versus percent occlusion of the cross-sectional area of the descending aorta is shown in FIG. 5A. As can be seen from these data generated in a model system, a favorable increase in cerebral blood flow and aortic blood pressure occurs at 50 percent occlusion and greater, at 56 percent occlusion and greater, and at 64 percent occlusion and greater. An even more favorable increase occurs at 71 percent occlusion and greater, 76 percent occlusion and greater, and at 83 percent occlusion and greater. A still more favorable increase can be seen at 91 percent occlusion and greater, 96 percent occlusion and greater, and at 98 percent occlusion and greater.

Figure 5B:
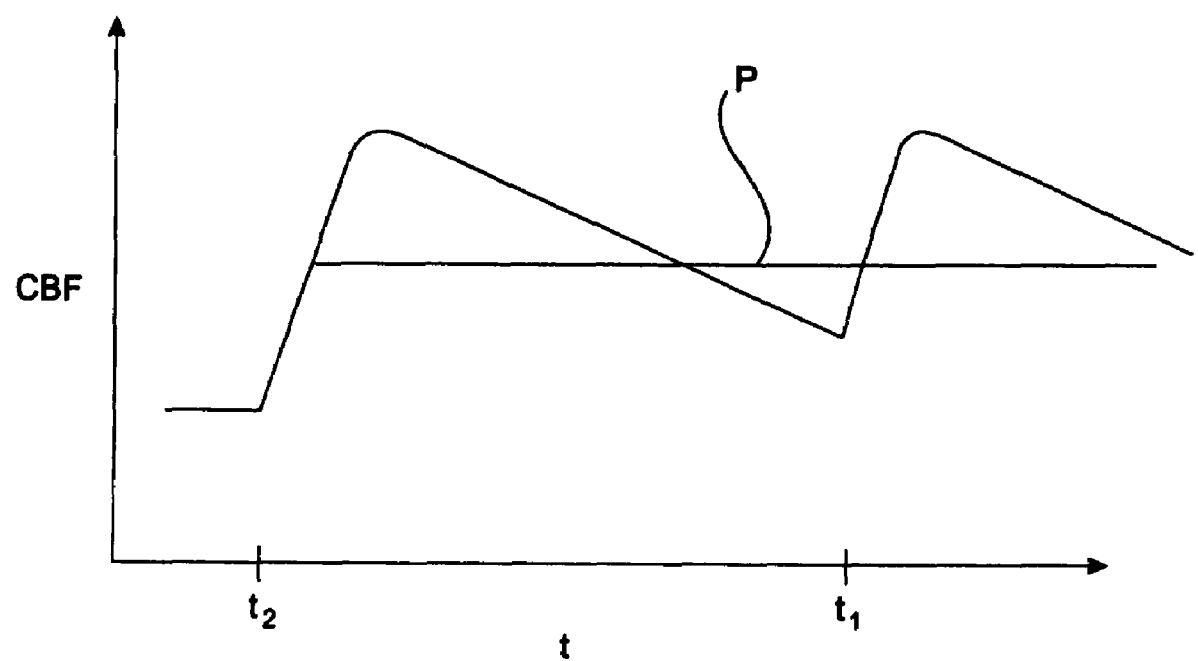
FIG. 5B illustrates a plot of cerebral blood flow v. time during use of the devices constructed according to the present invention for providing partial occlusion of a vessel.

It will further be understood that, when constriction is applied, there is a sharp increase in cerebral blood flow. The initial percent increase in cerebral flow is believed to be significantly higher than the percent increase in upstream aortic pressure in the presence of stroke. This appears to be the case for both the ischemic brain and the normal brain. A plot of cerebral blood flow versus time as set forth in FIG. 5B, however, shows that the cerebral blood flow rate decays with time after the initial application of the constrictor at time=$t_1$. This decay is possibly due to autoregulation within the brain. When the constriction is released, even for a short time (e.g., 10 seconds, 20 seconds, 30 seconds, 1 minute, or more), and then applied again (time=$t_2$), there is again a sharp increase in cerebral blood flow followed by gradual decay. Thus, one contemplated treatment regimen would include periodic (every 30 minutes or one hour) release of constriction to "reset" the autoregulatory system followed by re-expansion of the occluder at time $t_2$. Another contemplated treatment regimen would include a gradual increase in constriction with time in order to maintain an approximately constant rate of increased cerebral blood flow.

The aorta is a curved vessel that bends as it progresses from the aortic arch to the branch at the femoral arteries, as shown in FIG. 4. When one or both of the occlusion balloons are inflated, the blood pressure in the aorta upstream of the occluder(s) is caused to increase, while the pressure below the occluder(s) is decreased from baseline. With significant obstruction, e.g., 85-95 percent diameter obstruction, this pressure drop along the length of the occlusion balloon(s) can be significant, on the order of 20-150 mmHg. This pressure drop, by acting on the cross-sectional area of the occlusion balloon(s) creates a substantial longitudinally directed compressive force on the shaft of the catheter. The pressure drop and force are pulsatile in nature (due to systole and diastole) and tend to pulsatilly push the occlusion device down and back up.

To minimize this motion it is desirable to reinforce the catheter shaft. One way to reinforce the shaft is to incorporate stiffening mandrel or stylet 240. This may be incorporated within the shaft at the point of manufacture or it may be introduced within the shaft once the occlusion device is positioned in the aorta. Furthermore, the mandrel or stylet 240 may be a solid wire, or may be a hollow tube, such as a hypotube.

In use, a guidewire is advanced into the aorta. Catheter 102 is advanced over the guidewire. Once the catheter is in place, the guidewire is removed and mandrel 240 is advanced into a lumen of the catheter until it reaches the proper position. In certain procedures, the mandrel has a curvature at the end to forcibly deflect the occlusion balloon(s) to the wall of the aorta. The mandrel is then periodically rotated to reposition constrictors 104 and 107 at a new location along the lumenal wall of aorta 22. This periodic movement ensures that branching vessels are not deprived of blood for too long.

Although the balloon(s) of this embodiment will tend to be deflected to the wall of the aorta, the mandrel will further assure that the balloon will be deflected, resulting in an eccentric annular flow path for the balloon. Although an eccentric annulus has less flow resistance than a concentric annulus, it is desirable to prevent this non-centering embodiment from periodically becoming centered, as this would allow the flow resistance to vary over time.

A further dual balloon device is illustrated in FIG. 6. Distal balloon 104 and proximal balloon 107 are both fabricated of an elastomeric material such as blow molded polyurethane. Both are preferably molded to have an initial inflated diameter of about 10 mm, with a capability of being inflated to 25 mm with increasing pressure. It is anticipated that other sizes could be utilized. For example, the distal balloon could be larger than the proximal balloon, with an initial diameter of 15 mm, and a capability of being inflated to 35 mm with increasing pressure.

Both balloons may have a body length of from 3-6 cm, preferably about 4 cm. The distal tapered cone 113 and proximal tapered cone 115 may have a length of 1-3 cm, and about 2 cm. Each balloon has two cylindrical waists 117 and 119 which are used in the securing of the balloons to catheter shaft 102. The balloons may be adhesively bonded to the catheter shaft, or may be thermally bonded. Other suitable means of joining the balloons are also contemplated.

Figure 6A:
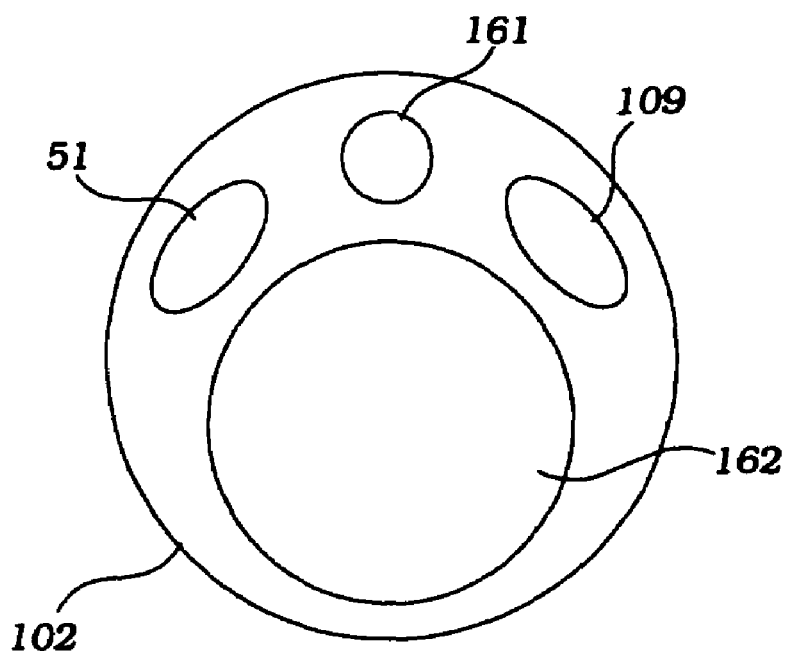
FIG. 6A illustrates a cross-sectional view of the device shown in FIG. 6.
Figure 6B:
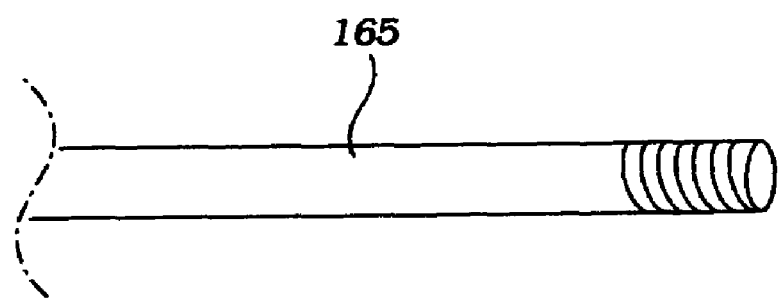
FIG. 6B illustrates a hypotube with an atraumatic tip.
Figure 6C:
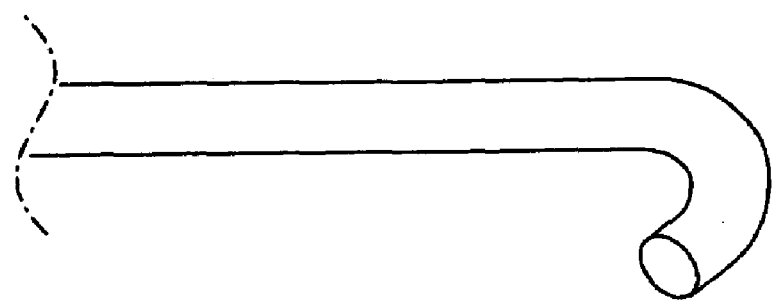
FIG. 6C illustrates a pig-tailed atraumatic tip for a catheter.
Figure 6D:
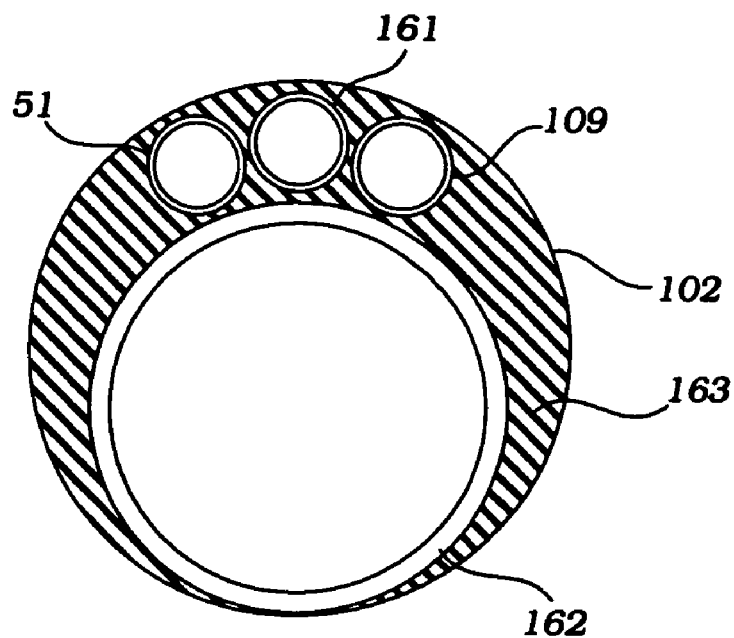
FIG. 6D illustrates a cross-sectional view of an alternative design for the catheter of FIG. 6.
Figure 6E:
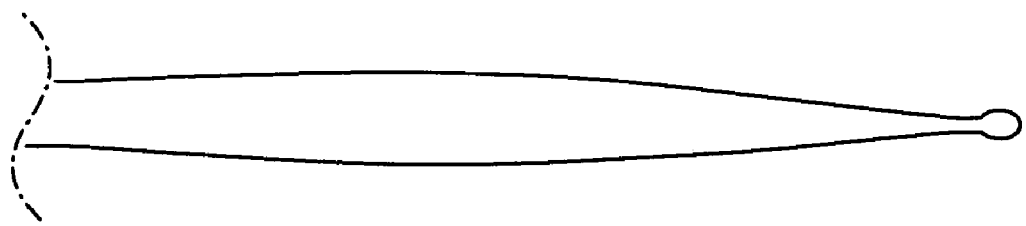
FIG. 6E illustrates a stylet for use in the present invention.
Figure 6F:
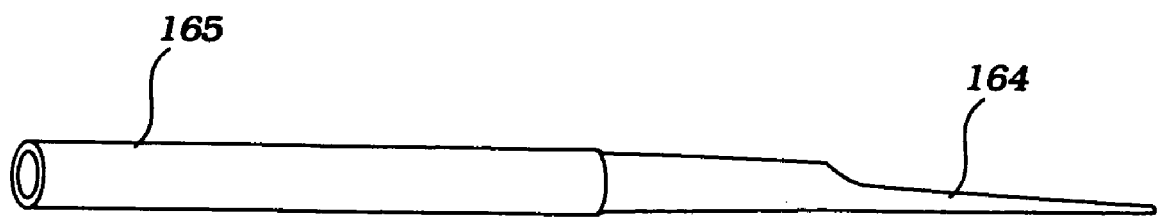
FIG. 6F illustrates a hypotube having a skive.

The balloons 104 and 107 are mounted on the distal region of catheter shaft 102. In this embodiment, the catheter shaft structure includes a unitary extruded multi-lumen tube (see cross-section in FIG. 6A), which extends for the full length of the device, with the exception of a soft tip attached at the distal end. The multi-lumen tube is preferably formed of an extrudable polymer, such as Pebax, polyethylene, polyurethane, polypropylene, or nylon. Alternatively, the shaft structure could be fabricated as illustrated in FIG. 6D. In this structure, individual thin walled tubes are used to define each lumen, and are preferably formed of a material suitable for very thin walls, such as polyimide or polyimide composite structures. As illustrated, the inter-balloon pressure monitoring lumen 161, and the inflation lumens 51 and 109 are defined by thin polyimide tubes, and the wire lumen is defined by a thin walled composite tube of PTFE, braided metal, and polyimide. The four thin walled tubes 51, 109, 161, and 162 are then encased within an extrusion or coating 163 of a polymeric material, such as Pebax, polyurethane, polyethylene, or other suitable polymer.

There are four lumens within tube 102, wire lumen 162, inter-balloon pressure monitoring lumen 161, and two inflation lumens 51 and 109, one each for delivery of inflation fluid to each balloon. Each balloon is inflated via ports 52 and 105 which allow fluid communication between the inflation lumen and the balloon interior. The portion of the inflation lumens which extend distally of their respective ports are occluded by suitable means such as an adhesive plug.

The inter-balloon pressure monitoring lumen 161 is in fluid communication with the surrounding blood via a port 160 in the tubing wall. When a suitable fluid such as saline resides in this lumen during used of the device, the blood pressure at the port is transmitted down the lumen to a pressure transducer. When the device is positioned as preferred, with the two balloons spanning the renal arteries, the renal blood pressure can be monitored, providing input to influence the degree of balloon inflation of the two balloons.

Wire lumen 162 is used during initial placement with a guide wire, which may be later removed, or may be left in place. The remaining space within the wire lumen may be used to monitor the blood pressure upstream from distal balloon 104. This is another input which may be used to influence the degree of inflation of one or both balloons.

Preferred tubing dimensions for the inflation lumens are between 9 and 60 mils, more preferably between 1 and 20 mils. Preferred tubing dimensions for the pressure lumens are between 5 and 60 mils, more preferably between 8 and 20 mils. Preferred tubing dimensions for the main lumens are between 30 and 80 mils, more preferably between 35 and 60 mils.

As mentioned, the shaft structure also includes a soft tip. Preferably, this is a single lumen tube fabricated of a more flexible material than that of the multi-lumen tubing. The tip is attached to the distal end of the multi-lumen tube by suitable means such as a thermal or adhesive butt joint. The single lumen within the tip creates an extension of the wire lumen. The soft tip is preferably about 2 to 10 cm long, and serves as an atraumatic tip facilitating catheter introduction and positioning, as well as providing an atraumatic "bumper" to the device during long term indwelling use. The tip may be straight, and may further include a tapering dimension on the outer and inner diameters. The tip may also be fabricated in a "pigtail" shape (FIG. 6C), which straightens in the presence of a guide wire extending through the wire lumen, but returns to the curled shape upon removal of the guide wire. A pigtail shape is relatively atraumatic.

The device as described is relatively flexible for smooth advancement over a guidewire, and may be introduced into the aorta without the need for fluoroscopic guidance. Radio-opaque markers would nonetheless preferably be provided, in the instances where fluoroscopic guidance is utilized, or if a simple plate x-ray is used to assist in device positioning.

As mentioned previously, when one or both balloons of a dual balloon device are inflated, significant longitudinal compressive forces can be imposed on the catheter. To help stabilize the device, the shaft structure of this embodiment provides for subsequent introduction of a stiffening element, such as a wire stylet, or a hypotube. If a wire stylet is used, the initial delivery guidewire is removed, to make room for the stylet. The stylet (FIG. 6E) is preferably tapered, and has a bulbous tip, facilitating smooth introduction into the wire lumen. The stylet may be quite large, occupying most of the available lumen. However, it is preferable to still maintain a clearance between the stylet and the wall of the wire lumen, to maintain the ability to monitor blood pressure. Alternately, the stylet may incorporate a pressure transducer mounted near the tip, in which case, the wire lumen can be fully occupied by the stylet.

If a hypotube is used as the stiffening element, the initial guide wire need not be removed, as long as the inner diameter of the hypotube is large enough to accommodate the guide wire, which is typically either 0.035 or 0.038 inches in diameter. Preferably, the hypotube has a diameter slightly less than the wire lumen diameter, and a tapering outer diameter toward the distal end, to facilitate smooth tracking in the wire lumen. Hypotube 165 (FIG. 6F) can further incorporate a "skive" to gain further flexibility near the distal end to facilitate smooth tracking. Alternately, the distal portion of the hypotube can have a helical cut of progressively tighter pitch (FIG. 6B), or other patterns of removed material in hypotube 165 to facilitate a gradually increasing flexibility. The inner lumen of the hypotube can be used as a pressure monitoring lumen for the upstream aortic pressure. Preferably the hypotube is coated both on the internal surface by a lubricious and non-thrombogenic material, such as a hydrophilic coating, PTFE liner, or a paralene coating. With both the wire stylet and the hypotube stiffening elements, it is contemplated that they could be incorporated initially within the device, as opposed to introduced subsequent to positioning of the balloons. If the stiffening element is initially incorporated into the shaft structure, it is preferred to connect somewhere in the distal region of the hypotube to the shaft tube, by suitable means such as an adhesive or thermal bonding.

Referring again to FIG. 6, at the proximal end of the device, a manifold structure is connected to the shaft structure. The manifold structure includes luer fittings that communicate with each of the lumens. Fitting 169 communicates with pressure monitoring lumen 161, fitting 167 communicates with proximal balloon inflation lumen 109, and fitting 168 communicates with distal balloon inflation lumen 51. The entire shaft structure and balloons are preferably coated with a non-thrombogenic coating, such as a hydrophilic coating, and/or a heparin coating. Other anti-thrombogenic agents are also possible, such as phospholcholine.

FIG. 7 illustrates an additional embodiment for a dual balloon occlusion device, and utilizes an alternative shaft structure. The shaft structure comprises two primary components-multi-lumen polymeric tube 102, and hypotube 165. The hypotube in this embodiment is fabricated directly into the device. The multi-lumen tube has three lumens, as shown in FIG. 7A. The main lumen 162 is circular. The hypotube resides within this lumen, and the remaining leftover annular space 105 serves as the inflation lumen for the distal balloon. Lumen 109 serves as the lumen for inflation of the proximal balloon, and lumen 161 serves as the lumen used in connection with inter-balloon pressure monitoring.

Hypotube 165 extends distally of the multi-lumen tube, and preferably terminates distal of the distal balloon. The hypotube is preferably lined on the inner surface, in a manner as described for the hypotube above. The lumen of the hypotube serves as the guide wire lumen as well as the pressure monitoring lumen for the upstream aortic pressure. The distal balloon is attached to the exterior of hypotube 165 by suitable means such as adhesive or thermal bonding. The distal end of the hypotube can incorporate features as described above to serve as a transition in stiffness. A soft tubular tip is preferably attached to the hypotube, creating an atraumatic tip.

Figure 8:
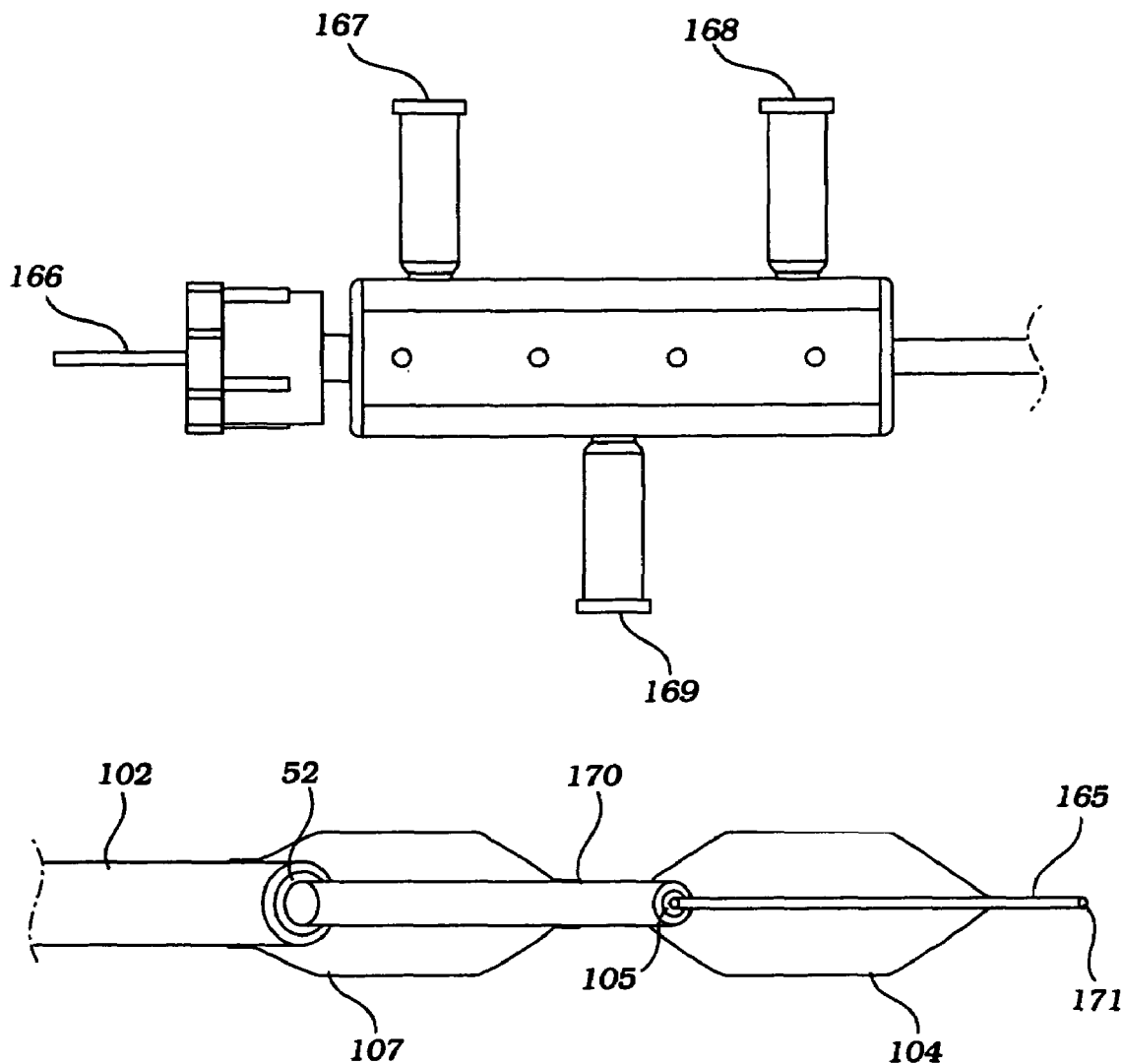
FIG. 8 illustrates another embodiment of the devices constructed according to the present invention for providing partial occlusion of a vessel.

FIG. 8 illustrates another embodiment of a dual balloon occlusion device, which utilizes an alternative shaft structure. The shaft structure is comprised of three coaxially positioned tubular components. Outer tube 102 is circular and polymeric, and defines lumen 52 which is used for inflation of proximal balloon 107. Middle tube 170 is circular and polymeric and defines lumen 105 which is used for inflation of distal balloon 104. Inner tube 165 is circular, and preferably a hypotube. The tubes are arranged such that proximal balloon 107 is attached proximally to outer tube 102, and distally to middle tube 170. The distal balloon is attached proximally to middle tube 170, and distally to inner tube 165.

Hypotube 165 defines lumen 171 which serves as a guide wire lumen, as well as a lumen for monitoring the upstream aortic blood pressure. The hypotube is preferably lined on the inner surface, in a manner as described for the hypotube above. The distal end of the hypotube can incorporate features as described above to serve as a transition in stiffness. A soft tubular tip is preferably attached to the hypotube, creating an atraumatic tip. As with the above embodiments, the entire shaft structure and balloons are preferably coated with a non-thrombogenic coating, such as a hydrophilic coating, and/or a heparin coating. Other anti-thrombogenic agents are also possible, such as phospholcholine.

Figure 9:
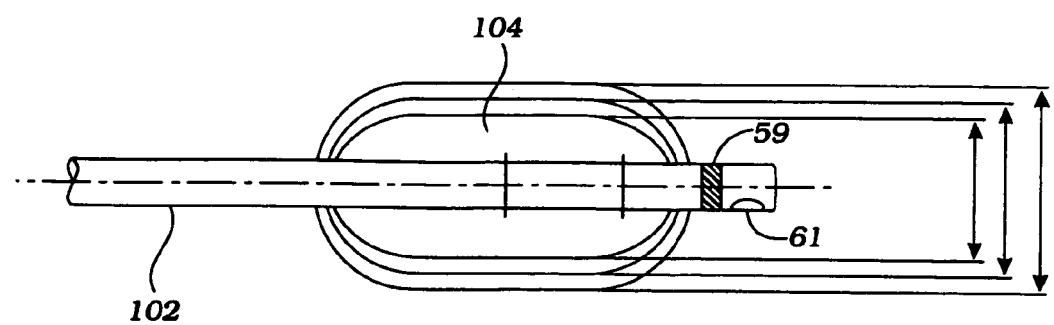
FIG. 9 illustrates a variable pressure balloon as used in devices constructed according to the present invention.

The balloon constrictors described herein are desirably blow molded from a material that is elastomeric, such as polyurethane, allowing an adjustable balloon diameter, as indicated in FIG. 9. The balloons will typically be sized to achieve full expansion, i.e., wrinkle-free expansion, at approximately 10 mm diameter in cross-section and at a pressure of 0.5-5 psi. A pressure of 5 psi at the low end of the operating range is desirable because the balloon is firm at this pressure and therefore resists the tendency to distort its geometry in a rapidly flowing blood stream. The balloon material will allow further expansion (beyond 10 mm) upon further inflation (e.g., by syringe) to a maximum diameter of approximately 25 mm and at a pressure of 12-50 psi. An operating range of approximately 10-25 mm balloon diameter is desirable to accommodate variations in patient anatomy and to allow the surgeon to vary constriction to adjust cerebral blood flow rate to the desired level. For larger aortas, a balloon of 15-30 mm may be desirable. A wrinkle-free balloon at 10 mm diameter cross-section is desired because wrinkles will produce unpredictable and variable flow properties, and wrinkles will produce a distortion in balloon material with material bunching together at the downstream edge of the balloon.

Figure 10:
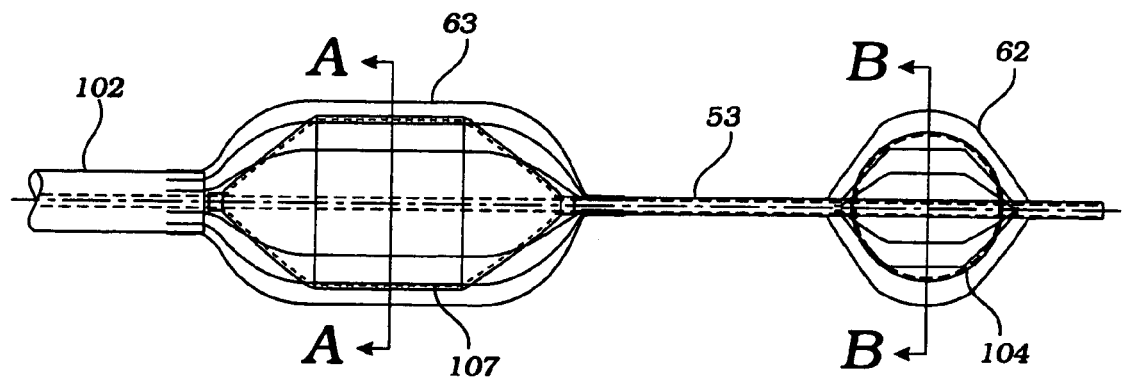
FIG. 10 illustrates another embodiment of the devices constructed according to the present invention having a constricting balloon with centering mechanism.
Figure 10A:
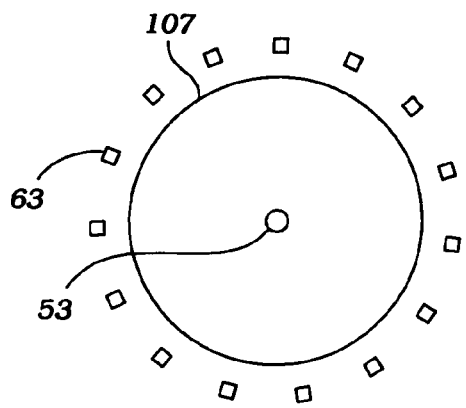
FIG. 10A illustrates a cross-section view of the device shown in FIG. 10 taken through section line A-A.
Figure 10B:
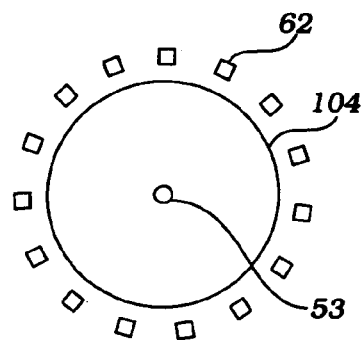
FIG. 10B illustrates a cross-section view of the device shown in FIG. 10 taken through section line B-B.

In other embodiments as depicted in FIG. 10, a centering mechanism will be used to maintain the constricting balloon apart from the vessel wall. Catheter 102 includes balloon 107, and inner sheath 53 includes balloon 104. The centering mechanism for balloon 107 here is provided by struts 63 mounted (either slideably or fixedly) at a proximal end to catheter 102, and at a distal end to inner tube 53. The centering mechanism for balloon 104 is provided by struts 62 mounted (either slideably or fixedly) at a proximal end to inner tube 53, and at a distal end to inner tube 53. A cross-section taken through section line A-A is shown in FIG. 10A, and a cross-section taken through section line B-B is shown in FIG. 10B. Alternative structures, such as a braid as a centering mechanism, are also contemplated.

Figure 11:
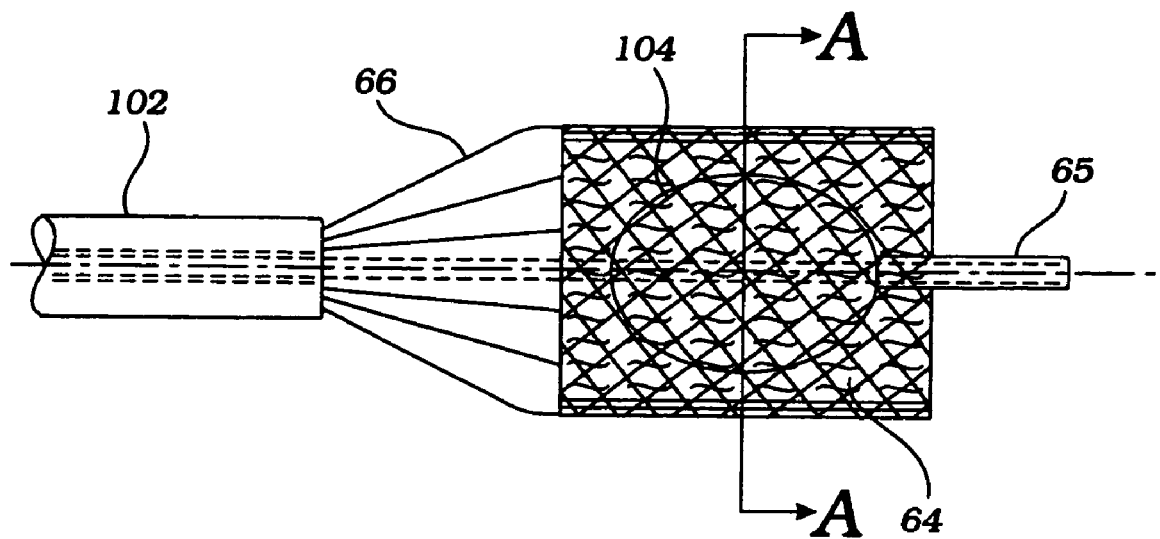
FIG. 11 illustrates another embodiment of the devices constructed according to the present invention having a constricting balloon with centering mechanism.
Figure 11A:
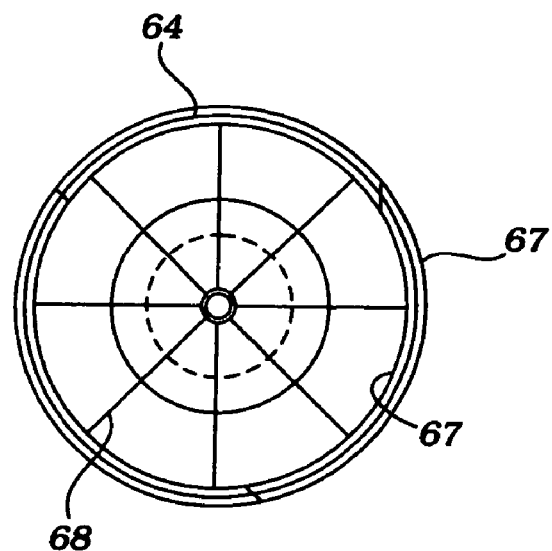
FIG. 11A illustrates a cross-section view of the device shown in FIG. 11 taken through section line A-A.

An alternative centering mechanism is shown in FIG. 11. Catheter 102 includes inner shaft 65 having a working channel. Constricting balloon 104 is bonded to shaft 65 at a distal end thereof. Self-expanding wires 66 are bonded at one end to catheter 102, and at a second end to centering mechanism 64. Here, centering mechanism 64 is a deployable wire mesh with fabric or polymer cover. A cross-section taken through section line A-A is shown in FIG. 11A. Wire mesh 64 is surrounded by cover 67. Distal supporting struts 68 are provided to strengthen the centering mechanism distally.

By maintaining the constricting balloon centered in the vessel, blood flows around the balloon on all sides. Thus, all branching vessels are perfused when this design is employed. Moreover, the velocity of blood flow increases in the region of the constrictor. This increased velocity in combination with the balloon channeling blood against the vessel wall can actually increase perfusion of branching vessels in certain cases. It will be understood that, in the absence of a centering mechanism and without a mandrill, the catheter and the one or more balloons will contact and bear against the lumenal wall of the aorta.

Figure 12:
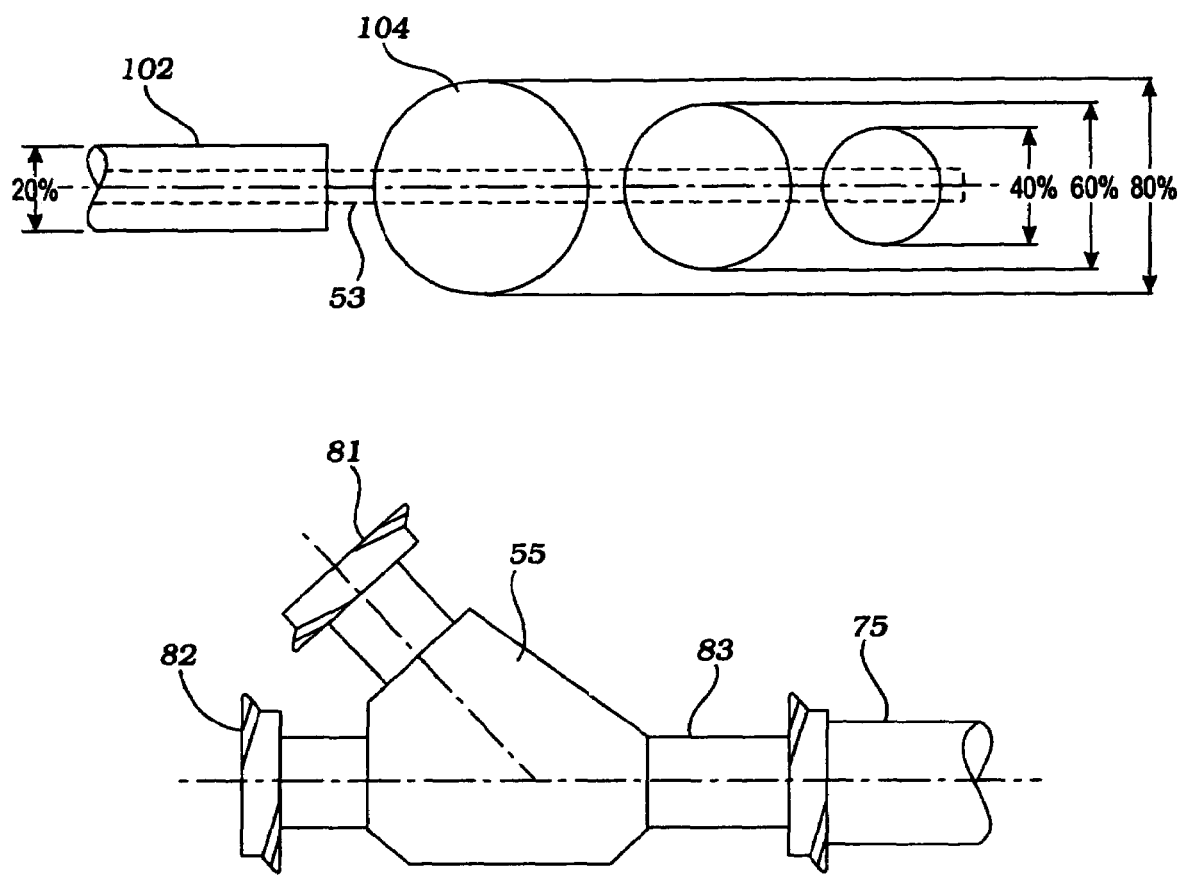
FIG. 12 illustrates another embodiment of the devices constructed according to the present invention having assorted balloon sizes.

In another embodiment as shown in FIG. 12, catheter 102 carries slideable inner shaft 53. Shaft 53 includes an inflation lumen and an assortment of constricting balloons 104 mounted at different positions. Each of these balloons has a different diameter of expansion to accommodate different degrees of constriction and different patient anatomy. In use, the first and smallest balloon is advanced from the distal port of catheter 102 and deployed. If a larger balloon is needed, then the second, larger balloon is advanced out of the catheter and deployed. If needed, the third balloon can be advanced into the vessel and deployed. At the proximal end of catheter 102 is outer sheath 75 and Y-adapter 55 with inflation/deflation port 81 and port 82 for a guidewire, for flushing, or for access by any other tools or instruments. Y-adapter 55 is connected to sheath 75 by hub 83 that has capabilities for multiple position adjustment.

Figure 13:
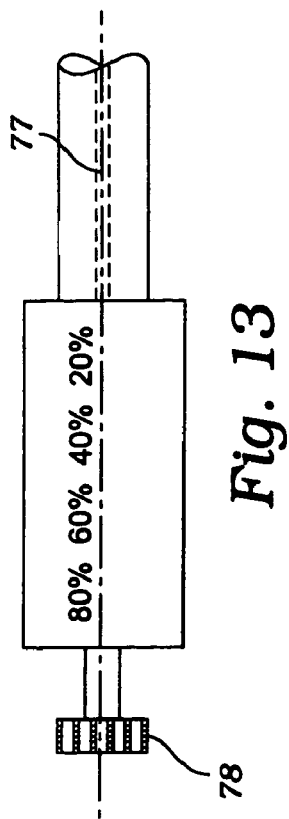
FIG. 13 illustrates another embodiment of the devices constructed according to the present invention having a control rod and membrane barrier.
Figure 13A:
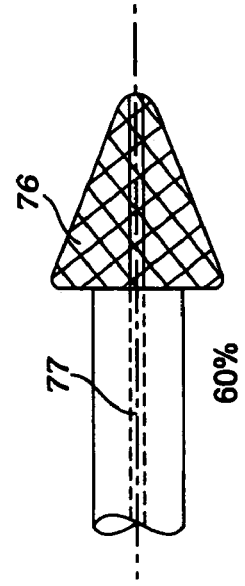
FIG. 13A illustrates the membrane barrier with a minimum (20%) cross-sectional profile.
Figure 13B:
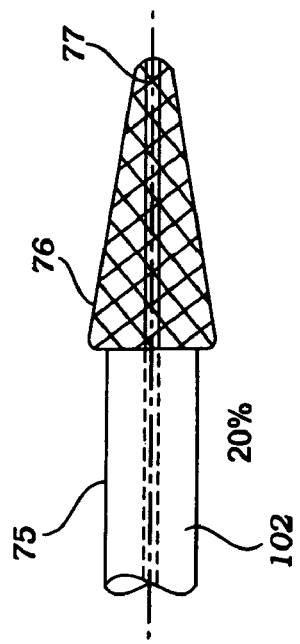
FIG. 13B illustrates the membrane barrier with an enlarged (40%) cross-sectional profile.
Figure 13C:
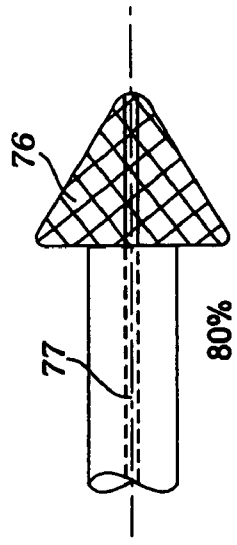
FIG. 13C illustrates the membrane barrier with a further enlarged (60%) cross-sectional profile.
Figure 13D:
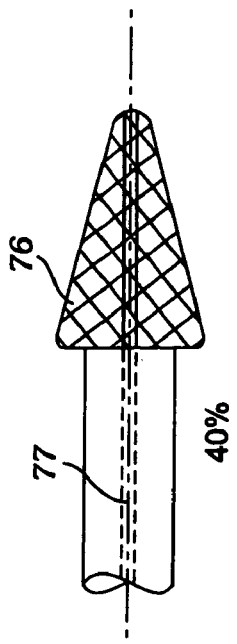
FIG. 13D illustrates the membrane barrier with a further enlarged (80%) cross-sectional profile.

FIG. 13 depicts occlusion membrane 76 that acts as an occluding member instead of using a balloon. Occlusion membrane 76 comprises a coated mesh. Catheter 102, having a flexible outer sheath, carries control rod 77. The distal end of control rod 77 is fixed to occlusion membrane 76 at its distal end. When control rod 77 is extended, occlusion membrane 76 is stretched as shown in FIG. 13, reducing the cross-sectional profile at the proximal end of occlusion membrane 76. As control rod 77 is withdrawn, occlusion membrane 76 progressively expands, increasing the cross-sectional profile at the proximal end as shown in FIGS. 13B, 13C, and 13D. At the proximal end, control rod 77 terminates in positioning handle 78 for adjusting the cross-sectional profile of the occlusion membrane 76.

Figure 14:
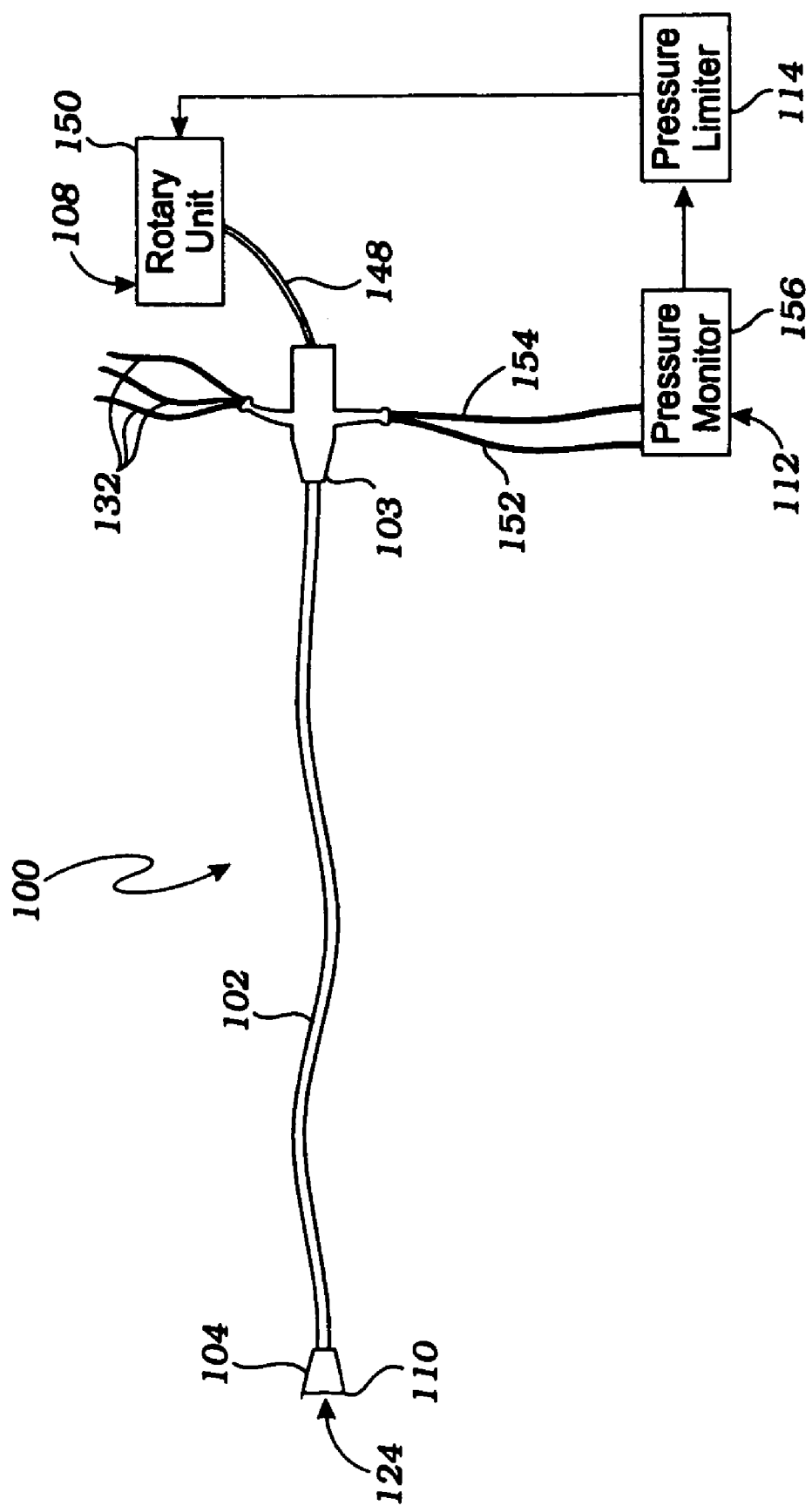
FIG. 14 illustrates another embodiment of the devices constructed according to the present invention for providing partial occlusion of a vessel.

FIG. 14 depicts occlusion catheter 100 for use in the methods described herein. The device includes elongate catheter 102, distally mounted expandable constrictor, i.e., occluder, 104 having distal opening 124 and variable flow mechanism 108. The constrictor, when expanded, has maximum periphery 110, which conforms to the inner wall of a vessel to form a secure seal with the vascular wall, such that blood flow through the vessel can be effectively controlled. Opening 124 receives blood from distal the constrictor and controls the passage of blood proximal the constrictor. Variable flow mechanism 108, connected to rotary unit 150, operates the constrictor, thereby controlling (1) the flow rate through the occlusion, and (2) upstream blood pressure. Preferably, the device includes manometer 112, which is connected to pressure monitor 156 and pressure limiter 114. Rotary unit 150 receives blood pressure measurements from the manometer. Pressure limiter 114, connected to the rotary unit and the pressure monitor, prevents the upstream and downstream blood pressure from exceeding, respectively, a set maximum and minimum pressure differential. A proximal end of the catheter is equipped with adapter 103, from which pull wires 132 can be manipulated for collapsing the occluder and to which the rotary unit, pressure monitor, and/or pressure limiter can be connected.

Referring to FIG. 15, the occlusion device comprises catheter 102 and constrictor 104. The catheter is constructed from a biocompatible and flexible material, e.g., polyurethane, polyvinyl chloride, polyethylene, nylon, etc. The catheter includes lumen 116 through which various operative elements pass. Alternatively, the catheter may include more than one lumen to support various operative elements. The catheter also includes proximal adapter 103 (see FIG. 14), which provides an interface between the catheter and the various instruments received by the catheter. The occluding mechanism consists of outer conical shell 118 and inner conical shell 136, each having a distal open base and a proximal apex. Pre-shaped ring 130 is affixed to base 120 of the outer shell to facilitate expansion of the constrictor. The ring is formed of a resilient material, capable of expanding the occluder to achieve a maximum periphery, which is defined by the outer circumference of the ring. Ring 130, may, in certain embodiments, further include an anchoring mechanism, such as hooks, bonded to the outer circumference of the ring. Expansion of the ring causes the grasping structure to engage the surface of the vessel wall, thereby securing the occluder and preventing displacement in the vessel due to force exerted by blood flow. In other embodiments, the anchoring is provided by an adhesive strip, vacuum, or merely by frictional engagement of the vessel lumen by the ring.

The constrictor can be collapsed to facilitate insertion into and removal from a vessel. A plurality of pull wires 132 (FIG. 14) are disposed within torque cable 148, and are distally connected to base 120 of outer shell 118 and proximally passes through adapter 103. The constrictor is collapsed by applying a tensile force on wires 132, using torque cable 148 to provide leverage to the pull wires, thereby drawing the circumference of the open base 120 towards its center and collapsing the occluder. A guide sheath (not shown) can be alternatively used to collapse the constrictor. Using this technique, the guide sheath would cover the constrictor and be withdrawn to release the constrictor and advanced to collapse the constrictor.

Opening 124 is formed in base 138 and 120 of the respective inner and outer conical shells to provide an inlet for blood flow. Conical interior 106 communicates with ports 128 of the outer shell. When the constrictor is deployed, blood flows into opening 124, through interior 106, and exits through ports 128. The occluding mechanism comprises inner conical shell 136 (partially shown in phantom in FIG. 15), which is rotatably disposed within outer shell 118 as shown in FIGS. 8, 9, and 10. The inner shell can be rotated relative to the outer shell through torque cable 148, which is disposed in lumen 116 of catheter 102.

Manometer 112 comprises upstream pressure tube 152 and downstream pressure tube 154, both connected proximally to a pressure monitor to provide respective blood pressure measurements upstream and downstream the constrictor. The upstream pressure tube extends distal to opening 124, or may be attached to the inner shell. The downstream pressure tube extends through an orifice in the catheter proximal to the constrictor. The upstream and downstream blood pressure measurements are recorded and displayed by the pressure monitor at a proximal end of the catheter. A pressure limiter, programmed with a maximum pressure threshold to limit the upstream blood pressure and a minimum pressure threshold to limit the downstream blood pressure, is connected to the pressure monitor to receive pressure measurements therefrom, and transmits information to a rotary unit. The limiter thereby prevents the rotary unit from rotating the inner shell relative to the outer shell in a manner that would cause the upstream blood pressure to exceed the maximum threshold, or the downstream blood pressure to fall below the minimum threshold. Without the rotary unit, torque cable 148 can also be manually rotated to obtain desired upstream and downstream blood pressures. An audible alarm may be incorporated into the pressure limiter to sound when blood pressures exceeds the thresholds. The pressure limiter may further comprise an interlocking device. The interlocking device, in operative association with upstream and downstream tubes 152 and 154, can lock inner shell 136 with respect to outer shell 118 as blood pressures approach the set thresholds. It should be noted that although the rotary unit, pressure monitor, and pressure limiter are shown as separate units, they may be incorporated into an integral unit.

Referring to FIGS. 16A and 16B, the expanded constrictor comprises outer conical shell 118 having base 120 and apex 122, and inner conical shell 136 having base 138 and apex 140. The constrictor is preferably composed of a biocompatible material coated with heparin to prevent blood clotting. The conical shape of the expanded constrictor minimizes turbulence caused by placement of the occluder in the vessel. The outer and inner shells include 2, 3, 4, 5, 6, or any other number of ports 128 and 144, respectively, in communication with the conical interior to permit blood flow through the occluder. The inner shell can be rotated relative to the outer shell, so that ports 144 communicate with ports 128. Apices 122 and 140 of the respective outer and inner shells further comprise collar 126 and 142. The collars may include engaging threads, so that collar 142 can be inserted and secured into collar 126, and bonded to a distal end of the torque cable, such that the inner shell is coupled to and rotates with the torque cable. A rotary unit, preferably including a stepper motor (not shown), may be mechanically coupled to a proximal end of the torque cable to provide precise rotational position of the inner shell relative to the outer shell, thereby providing variable flow through the occluder.

Figure 17:
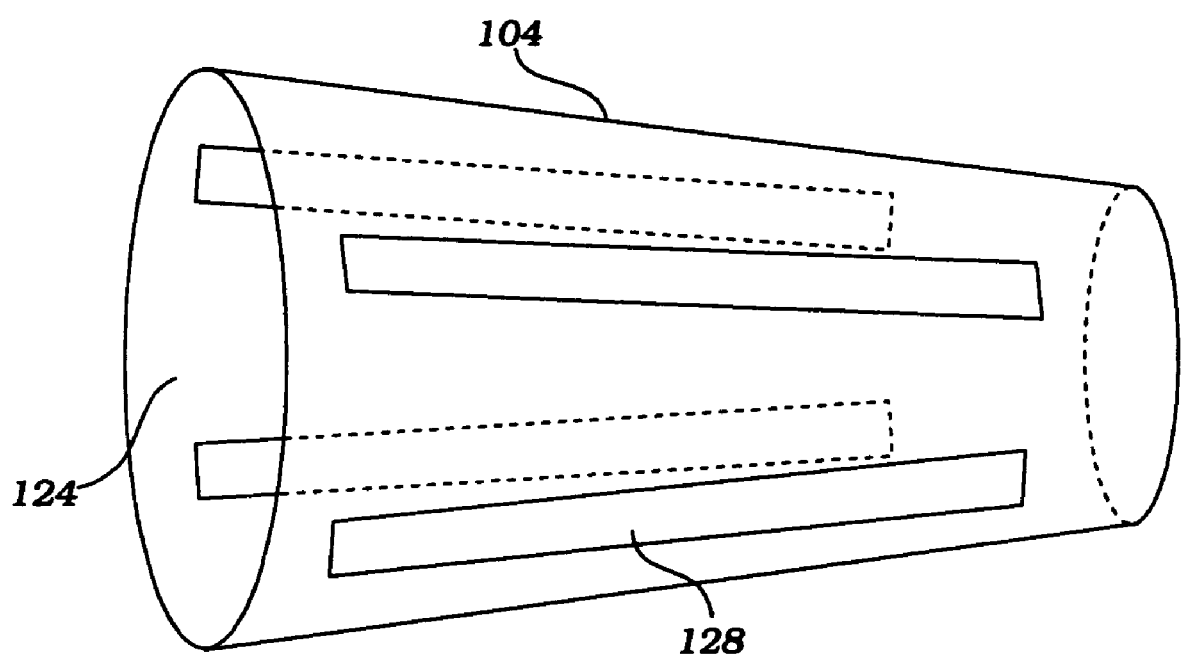
FIG. 17 illustrates an alternative embodiment of the constrictors of FIG. 15 having elongate rectangular ports.

Instead of having the circular ports in the inner and outer shells as depicted in FIGS. 16A and 16B, the constrictor may include 2, 3, 4, 5, 6, or any other number of ports having other suitable geometric shapes. FIG. 17 depicts constrictor 104 having a plurality of ports constructed as elongate rectangular slots 175.

Figure 18:
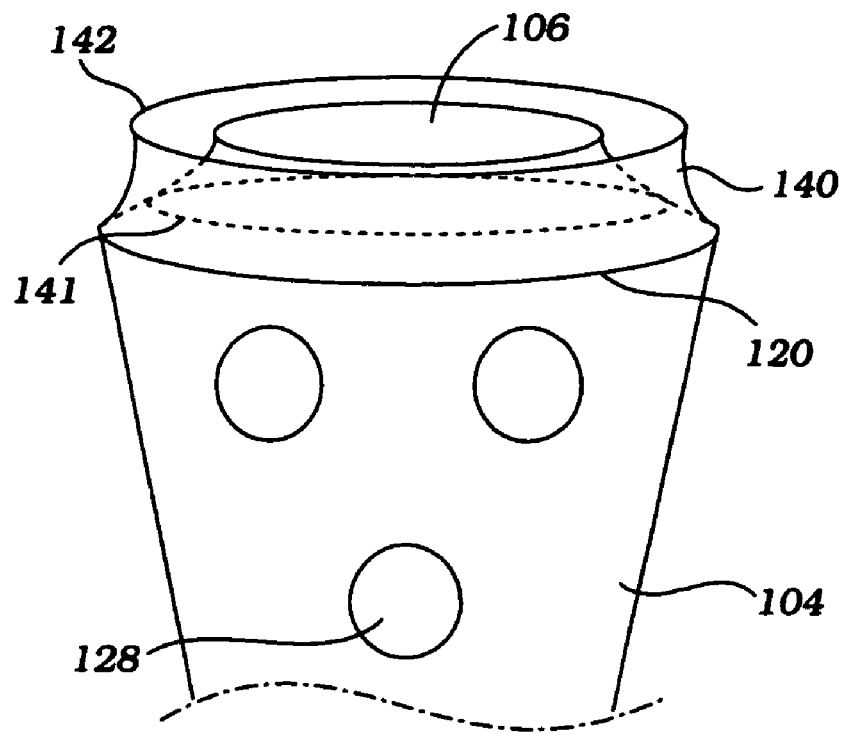
FIG. 18 illustrates another embodiment of the occluder having a beveled lip.

FIG. 18 depicts another embodiment of the constrictor, which comprises beveled lip 140 having distal end 142 and proximal end 141. The proximal end is affixed to base 120 of the outer conical shell. The proximal end has a larger diameter than the distal end and is everted to prevent the constrictor from being displaced in the direction of blood flow, thereby securing the constrictor in the vessel.

Figure 19:
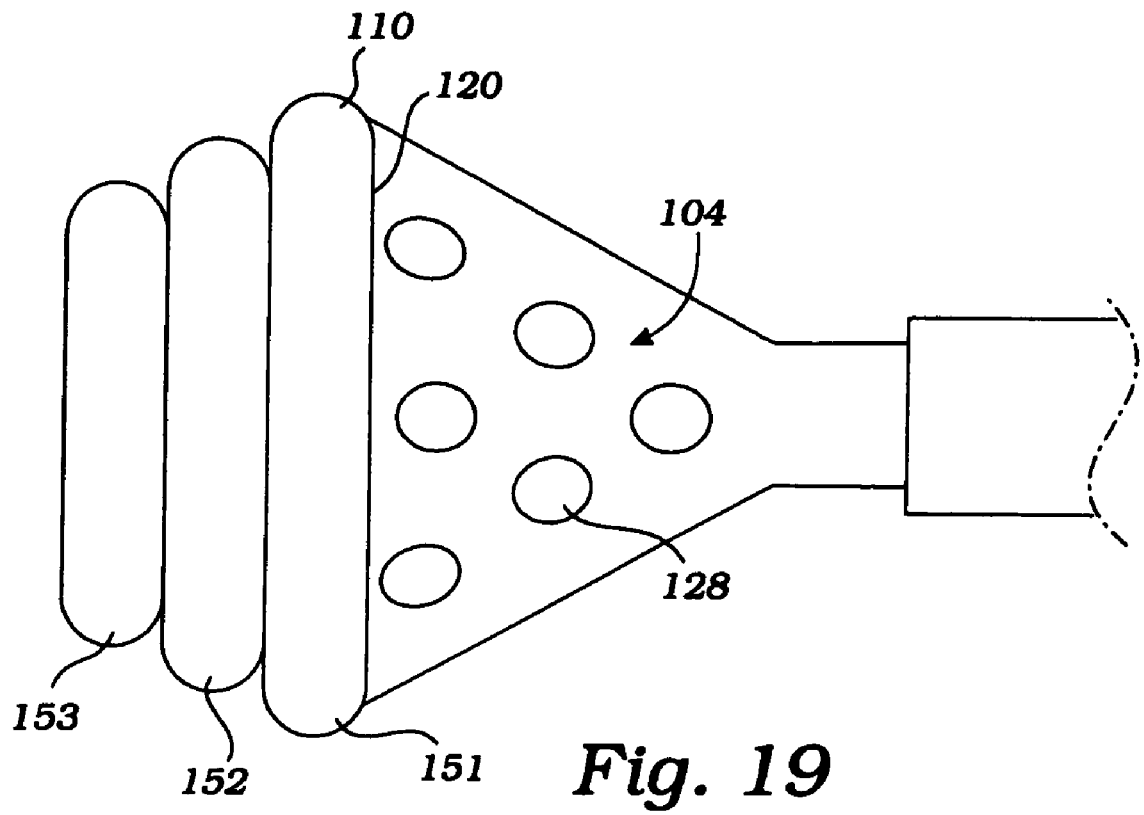
FIG. 19 illustrates another embodiment of the occluder having a plurality of graduated rings.

Still another embodiment of the occluder may includes 1, 2, 3, 4, 5, or any other number of graduated inflatable rings. In FIG. 19, ring 151 is affixed to the base of the conical shell. Ring 153, having the smallest inflated diameter, is attached to ring 152, which is then attached to ring 151, having the largest inflatable diameter. The fully inflated rings will have a thickness of approximately 2 to 3 millimeters. Similar to the beveled lip of FIG. 20, the rings prevent the outer conical shell from being displaced in the direction of blood flow, thereby securing the constrictor in the vessel.

Figure 20:
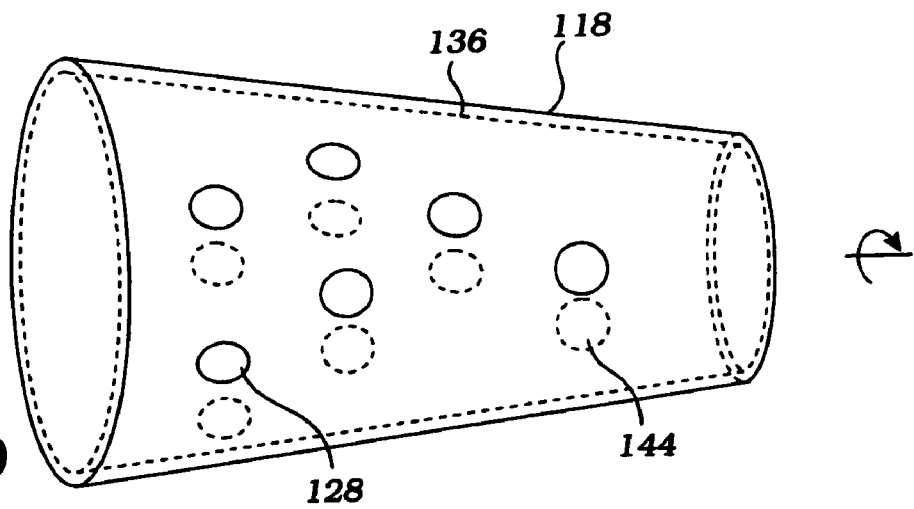
FIG. 20 illustrates complete misalignment of the ports on the outer and inner conical shells.
Figure 21:
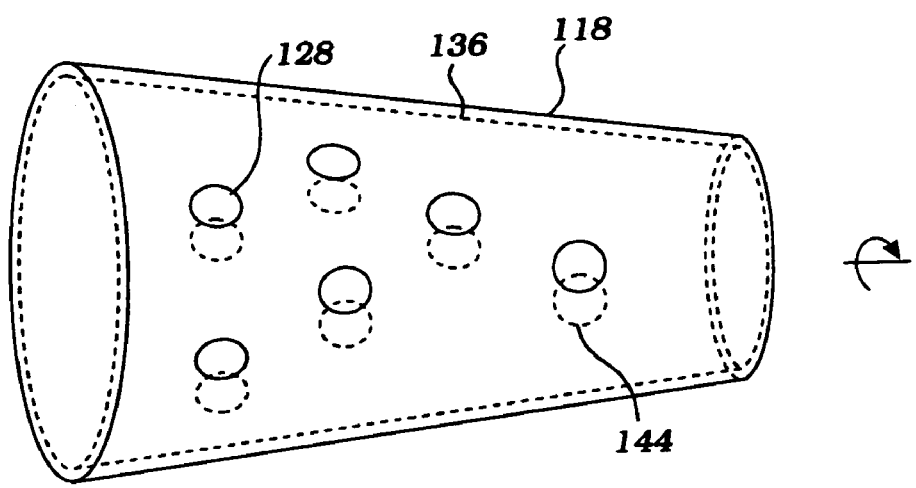
FIG. 21 illustrates partial alignment of the ports on the outer and inner conical shells.
Figure 22:
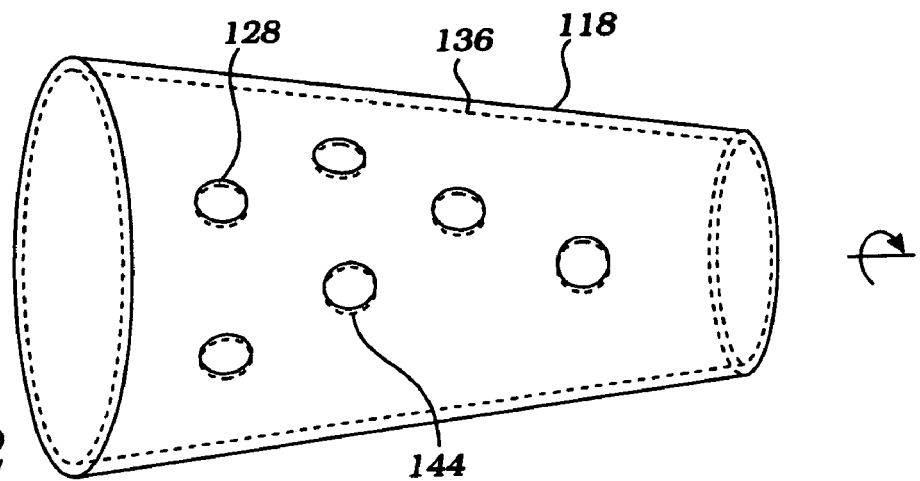
FIG. 22 illustrates complete alignment of the ports on the outer and inner conical shells.

The flow rate of blood through the constrictor can be easily controlled by rotating inner conical shell 136 (shown with dotted lines) relative to outer conical shell 118 as depicted in FIGS. 20, 21, and 22. In FIG. 20, the inner shell is rotated so that ports 144 and 128 are completely misaligned, thereby achieving no flow through the ports and complete vascular occlusion distally. As the inner shell is rotated clockwise relative to the second shell in FIG. 21, ports 144 on the inner shell become partially aligned with ports 128 on the outer shell, thereby achieving partial flow through the ports and partial vascular occlusion. In FIG. 22, with continuing clockwise rotation of the inner shell, ports 144 become completely aligned with ports 128, thereby achieving maximum flow through the ports. To provide a broader and more predictable range of blood flow through the conduit, the ports of the inner and outer shells are preferably of equal size and number such that they may align with each other.

Figure 23:
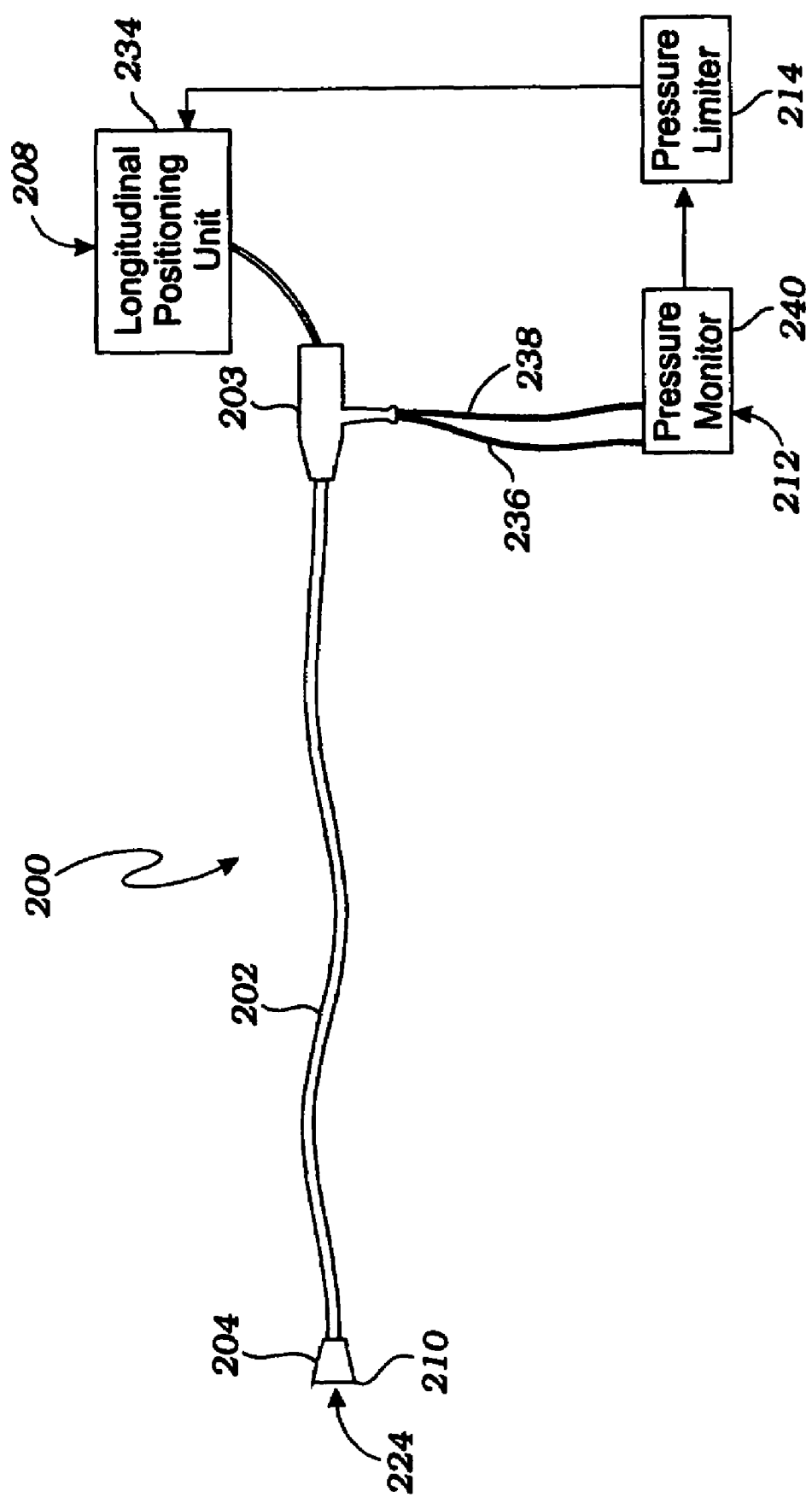
FIG. 23 illustrates another embodiment of the device for providing partial occlusion of a vessel.

FIG. 23 depicts another embodiment of the occlusion device for partial occlusion of blood flow in a vessel. Device 200 comprises elongate catheter 202, distally mounted expandable constrictor 204 with maximum periphery 210, opening 224, and variable flow mechanism 208 operatively associated with the constrictor. The catheter includes adapter 203 at its proximal end. Preferably, the device includes manometer 212 and pressure limiter 214, and pressure monitor 240. The pressure monitor records and displays blood pressure data received from the manometer. Longitudinal positioning unit 208, receiving signals from pressure limiter 214, and controls variable flow mechanism 208 to provide variable blood flow through the constrictor.

Figure 24:
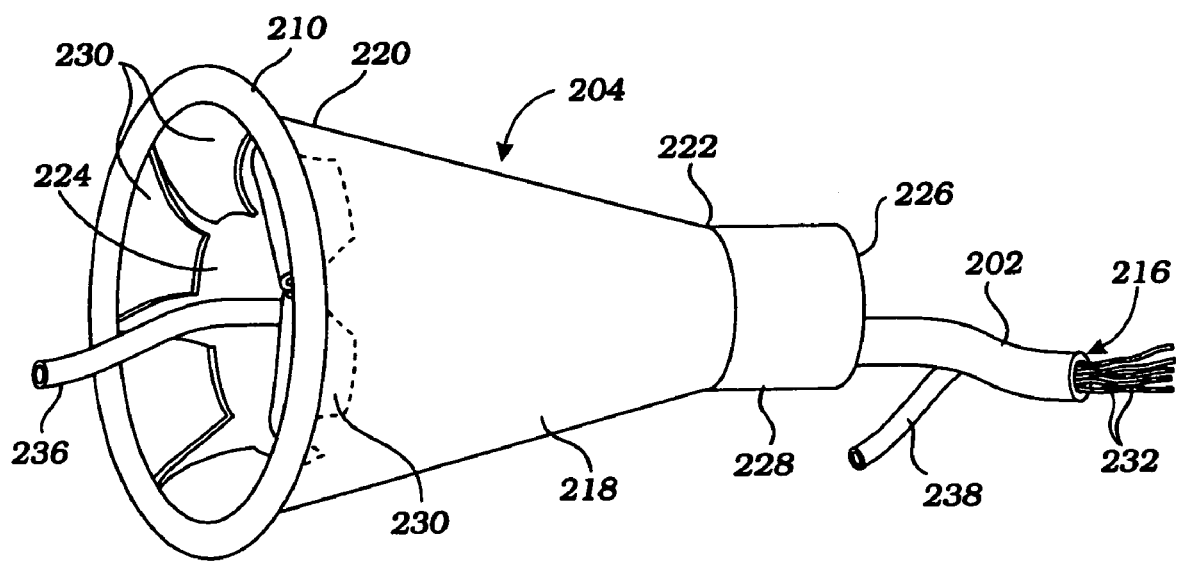
FIG. 24 illustrates another embodiment of the constrictor employed in the device of FIG. 23.

Referring to FIG. 24, catheter 202 includes lumen 216. Constrictor 204 comprises hollow conical shell 218 having base 220 and apex 222. The inner circumference of the base forms opening 224, which provides a distal inlet for blood flow through the constrictor. The inner circumference of apex 222 forms collar 228 with proximal opening 226, which provide an outlet for blood flow through the constrictor. The conical interior, disposed within shell 218, communicates with opening 224 distally and opening 226 proximally. When the base of the constrictor is positioned upstream in a vessel, blood flows into opening 224, through the conical interior, and exits downstream through opening 226. The catheter is bonded to collar 228 about a portion of its inner circumference. The constrictor is expanded by operation of ring 230, a beveled lip, or a series of graduated toroidal balloons as described above. The constrictor is collapsed and may be delivered to a vessel location by using a guide sheath.

The manometer comprises upstream pressure tube 236 and downstream pressure tube 238, which are disposed in lumen 216 of the catheter and connected proximally to a pressure monitor. The upstream pressure tube extends distal from the constrictor or may be bonded to the inner surface of the conical shell, thereby providing upstream blood pressure measurement. The downstream pressure tube extends through an orifice in the catheter proximal to the constrictor, thereby providing downstream blood pressure measurement.

The variable flow mechanism comprises a plurality of flaps 230 pivotally affixed to base 220. The flaps are preferably made of a resilient material, such as Nitinol, to resist movement caused by blood flow through the conduit. A plurality of pull wires 232, disposed through lumen 216, are distally connected to flaps 230, such that applying a tensile force to the wires pivotally displaces flaps 230 from their preformed position. Three of the flaps (shown in dotted lines) are displaced inward. Releasing the wires allows the resilient flaps to relax and return to their preformed position. The pull wires are coupled proximally to the longitudinal positioning unit, which provides precise displacement of the flaps relative to opening 224. Alternatively, wires 232 can be manually tensed to operate the flaps. The pressure limiter receives pressure measurements from the pressure monitor and transmits signals to the longitudinal positioning unit to prevent the upstream and downstream blood pressures from exceeding the set thresholds.

Figure 25A:
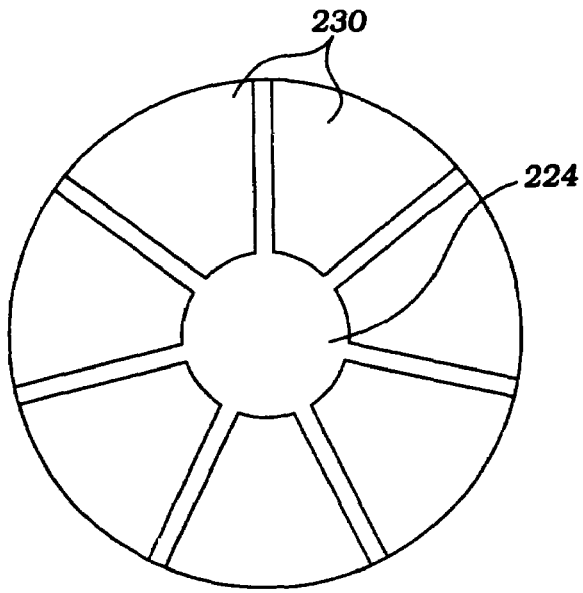
FIG. 25A illustrates a frontal view of the constrictor of FIG. 24 having a plurality of preformed flaps extending perpendicular to the longitudinal axis of the constrictor.
Figure 25C:
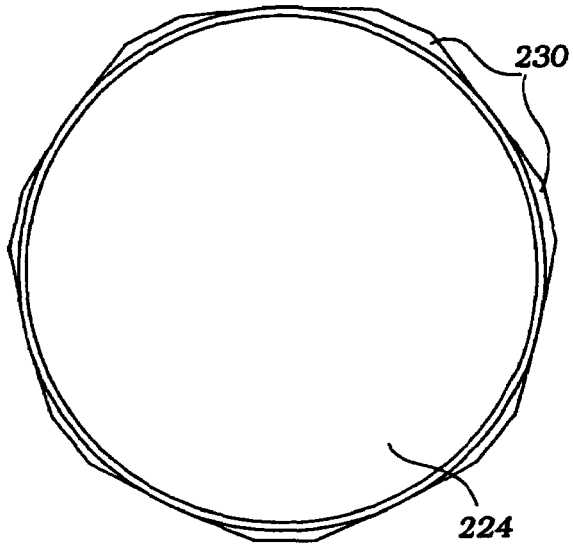
FIG. 25C illustrates a frontal view of the constrictor of FIG. 24 having a plurality of preformed flaps extending parallel to the longitudinal axis of the constrictor.
Figure 25B:
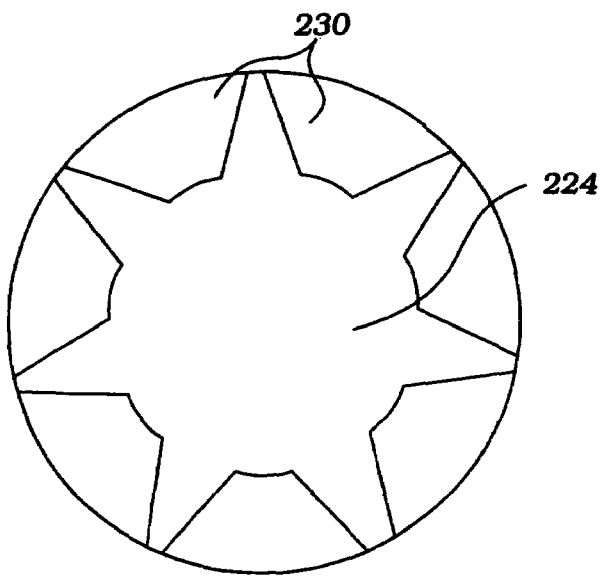
FIG. 25B illustrates a frontal view of the flaps of FIG. 25A under an external force.

FIGS. 25A, 25B, 25C, and 25D depict frontal views of the constrictor having flaps in various positions for controlling blood flow. In FIG. 25A, preformed flaps 230 extend radially inward toward the longitudinal axis of the catheter, as in the absence of a displacing force, i.e., an external force other than that created by blood flow. When the constrictor is positioned in the descending aorta, for example, the size of opening 224 and blood flow through the opening is minimized, thereby providing maximal aortic occlusion. In the presence of a displacing force, such as pulling the wires to displace flaps 230 from their preformed position as depicted in FIG. 25B, the size of aperture 224 and blood flow through the conduit increases, thereby providing partial aortic occlusion.

Figure 25D:
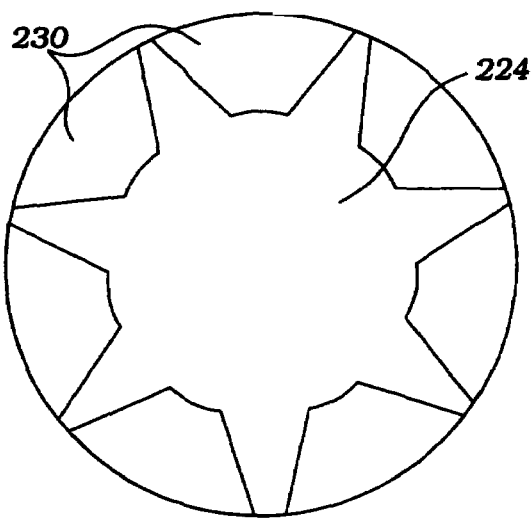
FIG. 25D illustrates a frontal view of the flaps of FIG. 25C under an external force.

Alternatively, preformed flaps 230 extend parallel to the longitudinal axis of opening 224 in the absence of a displacing force as depicted in FIG. 25C. The size of opening 224 and blood flow through the conduit are maximized, thereby providing minimal blood flow occlusion. In the presence of a displacing force, flaps 230 are pivotally displaced from their preformed position as depicted in FIG. 25D. The size of opening 224 and blood flow through the opening are minimized, thereby providing maximal blood flow occlusion. Thus, by pivotally displacing flaps 230 relative to opening 224, the size of the opening and flow rate through the constrictor is controlled to provide variable vessel occlusion.

Figure 26:
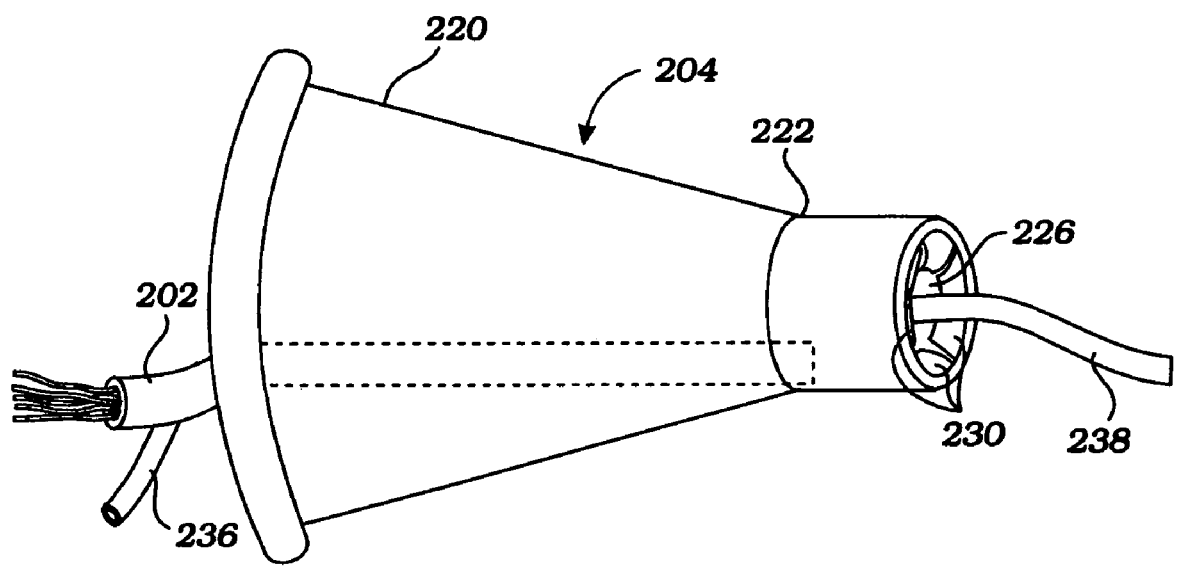
FIG. 26 illustrates another embodiment of the occluder having flaps included in the collar of the outer conical shell.

The constrictor shown in FIG. 24 can be alternatively mounted on catheter 202, such that base 220 is proximal to apex 222 as shown in FIG. 26. In this embodiment, flaps 230 are formed on open apex 222. When constrictor 204 is inserted downstream in the aorta, for example, pressure tube 238 extends distally from opening 226 to provide downstream blood pressure measurements, whereas pressure tube 236 extends proximally through an orifice in the catheter to provide upstream blood pressure measurements.

Figure 27:
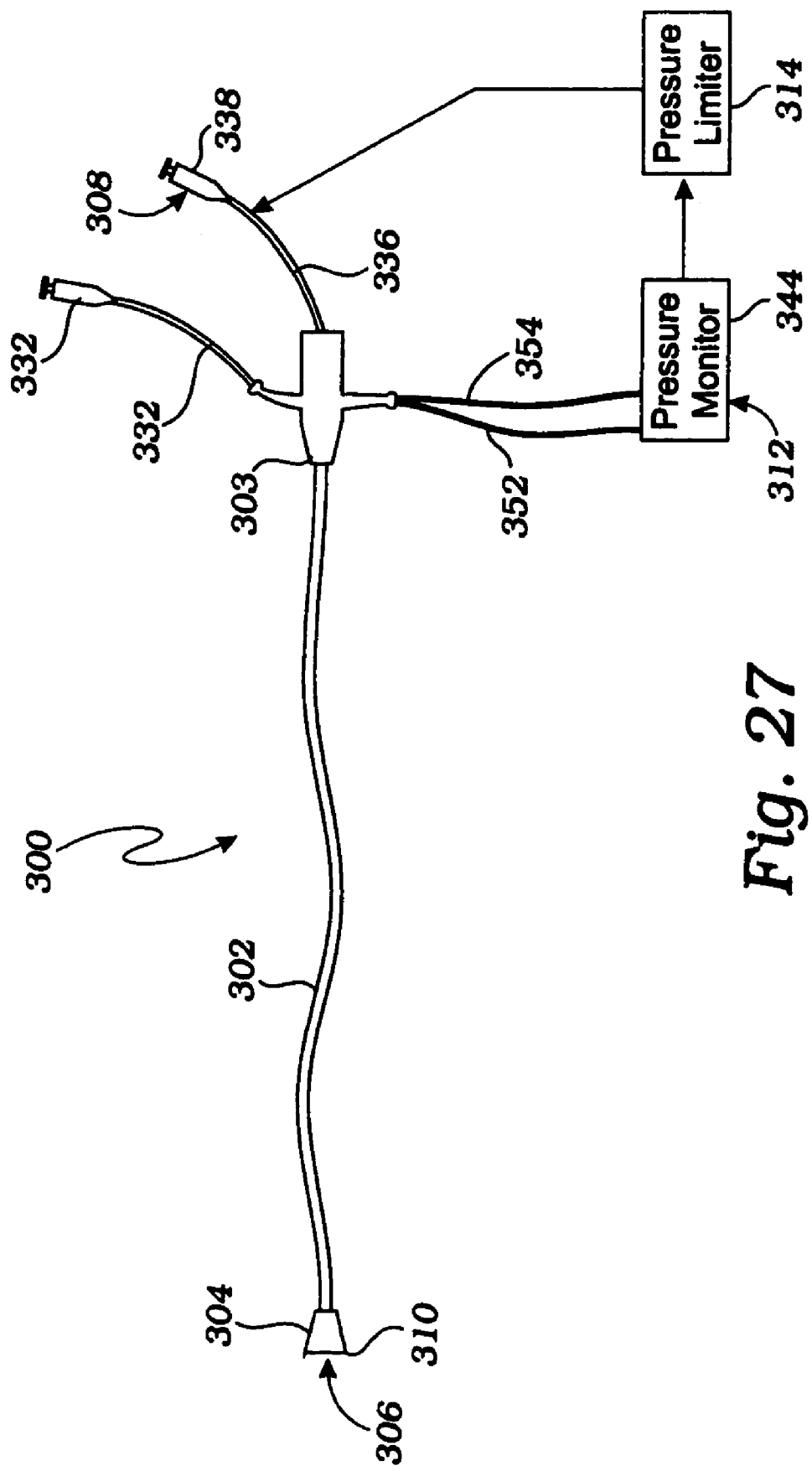
FIG. 27 illustrates still another embodiment of the device for providing partial occlusion of a vessel.

In FIG. 27, another embodiment of the device comprises catheter 302, a distally mounted occluder 304 with maximum periphery 310, blood passage 306 disposed within the constrictor, and variable flow mechanism 308 in operative association with the blood conduit. Inflation device 334 communicates with the constrictor, and inflation device 338 communicates with the variable flow mechanism. The device preferably includes proximal adapter 303, manometer 312, and pressure limiter 314. Pressure monitor 312 records and displays blood pressure data from the manometer. The pressure limiter is connected to the pressure monitor and to an interlocking valve on inflation device 338, such that the blood pressure upstream and downstream the constrictor can be controlled to prevent from exceeding set thresholds.

Figure 28:
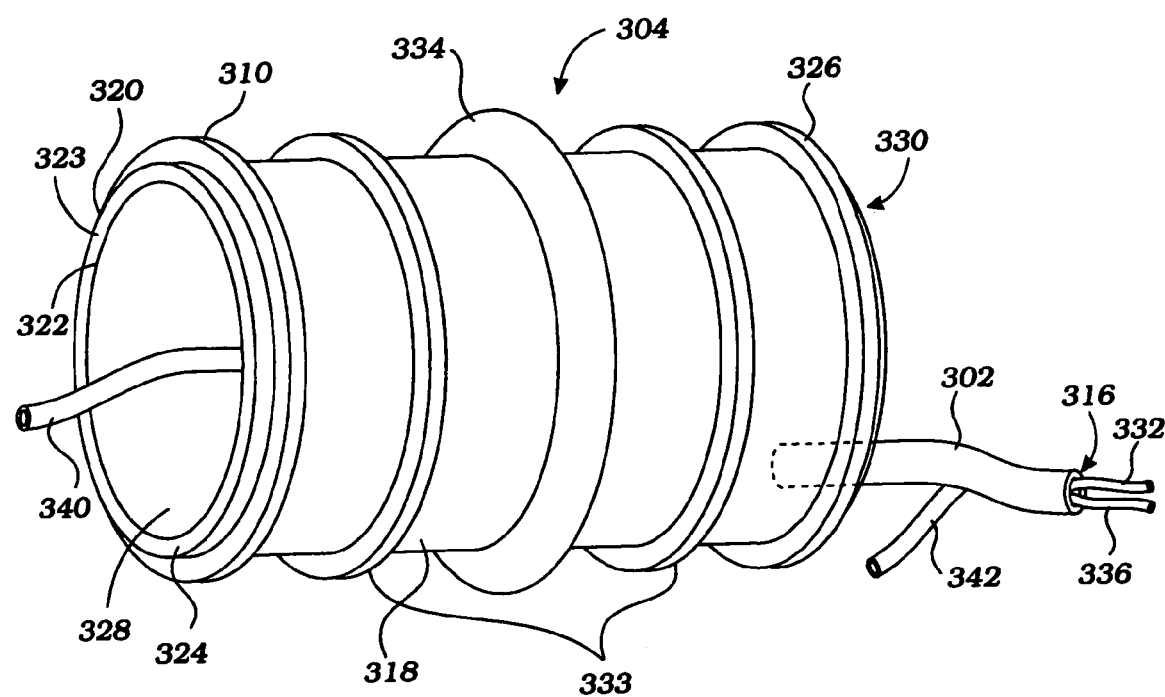
FIG. 28 illustrates an embodiment of the constrictor employed in the device of FIG. 27.

Referring to FIG. 28, constrictor 304 is mounted to a distal end of catheter 302 having lumen 316. The constrictor comprises a sleeve or cylindrical balloon 318 having outer wall 320 and inner wall 322, which enclose chamber 323. The cylindrical balloon has first end 324 with opening 328 and second end 326 with opening 330. Catheter 302 is bonded to inner wall 322 of the cylindrical balloon. Inflation tube 332, housed within lumen 316 of the catheter, communicates distally with the cylindrical balloon and proximally with a syringe or other inflation device. The cylindrical balloon can be expanded or collapsed by injecting or removing air, saline, or other medium. Occlusion is provided by toroidal balloon 334 disposed about the outer or inner surface of sleeve 318 and communicating with inflation tube 336 and a syringe. The inflation device may include an interlocking valve to prevent unintended deflation.

Lumen 306 communicates with opening 328 distally and opening 328 proximally. When deployed in a vessel, blood flows through lumen 306 and exits downstream opening 330. The constrictor may further include an anchoring structure, shown in FIG. 28 as rings 333, which are disposed about outer wall 320 of the cylindrical sleeve and define maximum periphery 310 of the occluder.

Manometer 312 comprises upstream pressure tube 340 and downstream pressure tube 342, which are operatively connected proximally to a pressure monitor. Pressure tube 340 is bonded to the lumen of the cylindrical balloon and extends distal to provide upstream blood pressure measurements, while tube 342 emerges from the catheter proximal the occluder to provide downstream blood pressure measurements.

Figure 29:
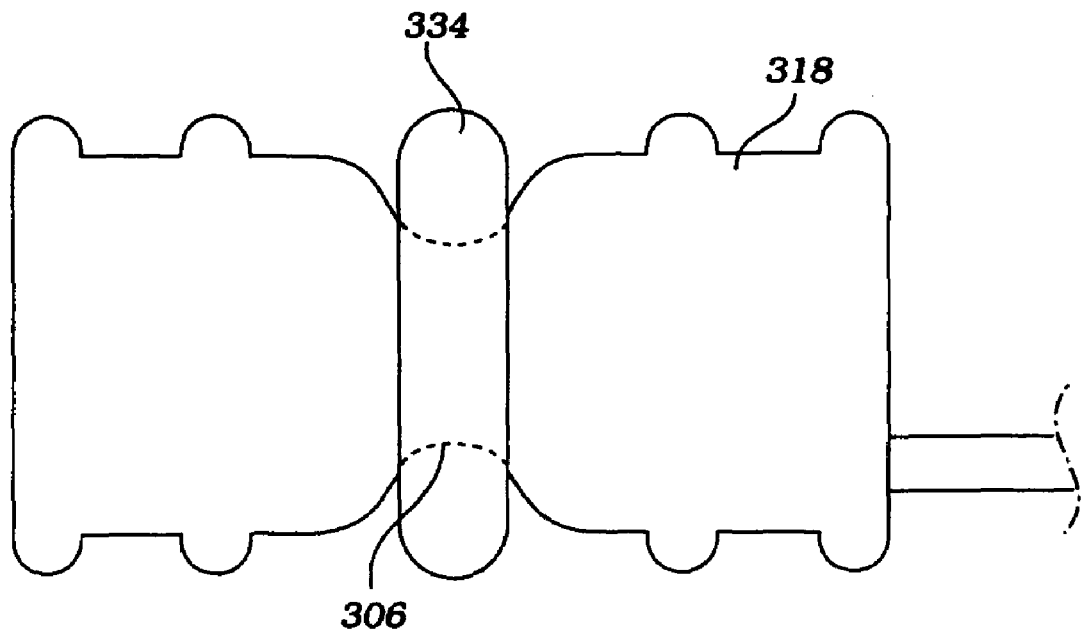
FIG. 29 illustrates the constrictor of FIG. 28, having an inflated ring-shaped balloon for reducing blood flow through a blood conduit.
Figure 30:
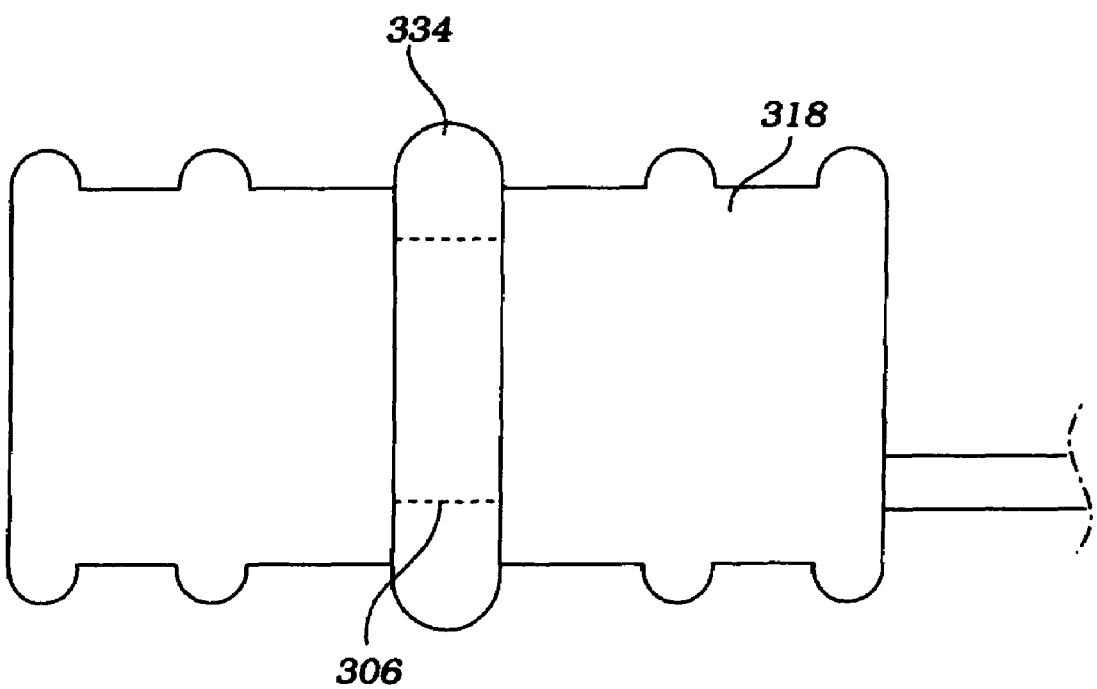
FIG. 30 illustrates the occluder of FIG. 28, having a deflated ring-shaped balloon.

In FIG. 29, fluid is injected to expand balloon 334, thereby constricting sleeve 318. As a result, blood flow is constricted. In FIG. 30, balloon deflation allows sleeve 318 to revert back to its pre-shaped geometry, increasing blood flow therethrough. Thus, balloon 334 can be inflated and deflated to vary the cross-sectional diameter of lumen 306 to vary flow rate.

Figure 31:
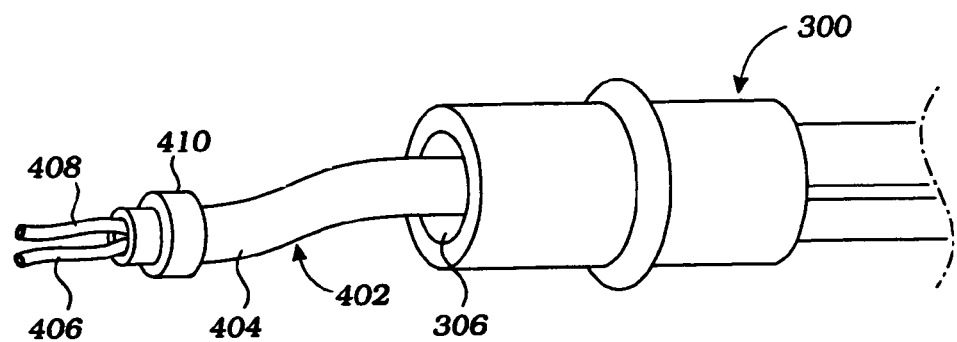
FIG. 31 illustrates a suction/atherectomy catheter introduced through the constrictor of FIG. 28.

The occlusion devices described herein can be employed with a variety of therapeutic catheters to treat vascular abnormalities. For example, as depicted in FIG. 31, suction/atherectomy catheter 402 can be inserted through lumen 306, such that the suction/atherectomy catheter is independently movable relative to occlusive device 300. Catheter 402 includes elongate tube 404 and distally located aspiration port 406, cutting device 408, and balloon 410 for removing thromboembolic material in a vessel.

Figure 32:
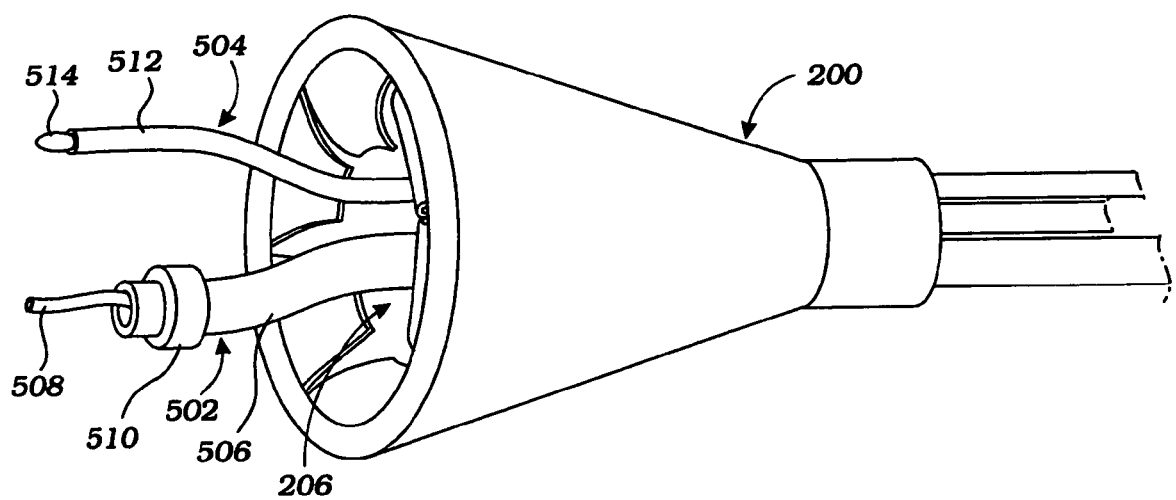
FIG. 32 illustrates a perfusion and an EPS catheter introduced through the constrictor of FIG. 28.

In FIG. 32, infusion catheter 502 and EPS catheter 504 are inserted through opening 206 of occlusion device 200, such that catheter 502 and 504 are independently movable relative to occlusion device 200. The infusion catheter, which includes elongate tube 506, distally located perfusion port 508, and expandable balloon 510, can be used to remove thromboembolic material in a vessel. EPS catheter 504, which includes elongate tube 512 and distally located ablation device 514, may be used to map out or ablate an extra conduction pathway in the myocardial tissue, e.g., in patients suffering from Wolff-Parkinson-White syndrome. The occlusion device, capable of augmenting cerebral perfusion, is therefore useful not only in facilitating definitive treatment but also in cerebral ischemia prevention during EPS and other cardiac interventions or cardiac surgery, such as coronary catheterization, where sudden fall in cerebral blood flow may occur due to arrhythmia, myocardial infarction, or congestive heart failure.

Figure 33A:
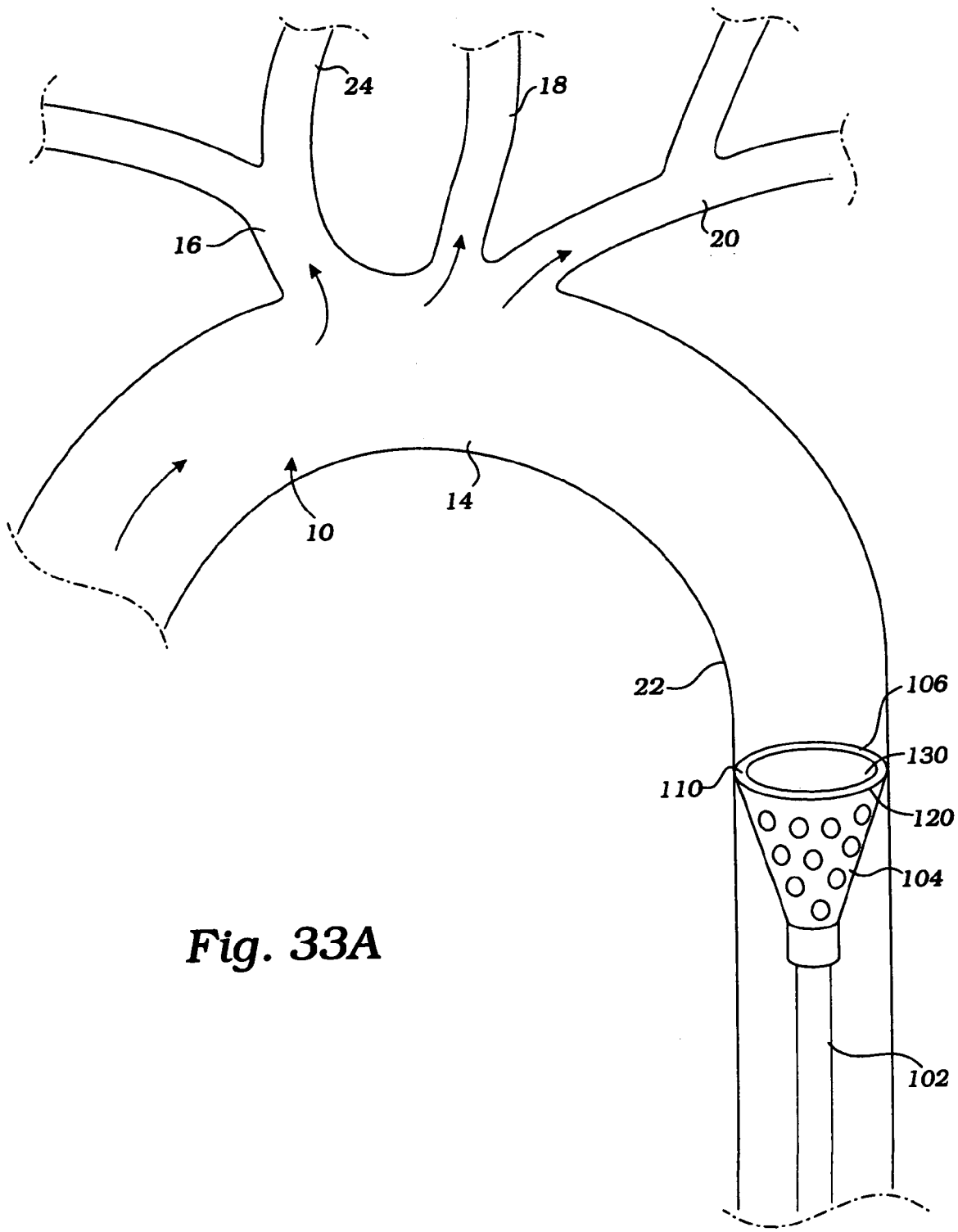
FIG. 33A illustrates the constrictor of FIG. 15 inserted in the aorta downstream from the left subclavian artery and partially occluding aortic blood flow.

Referring to FIG. 33A, occlusion device 100 described above can be used to partially occlude blood flow in aorta 10 of a patient suffering from global cerebral ischemia due to, e.g., septic shock, congestive heart failure, or cardiac arrest. Constrictor 104 can be introduced in its collapsed geometry through an incision on a peripheral artery, such as the femoral, subclavian, axillary, or radial artery, into the patient's aorta. A guide wire may first be introduced over a needle, and the collapsed constrictor is then passed over the guide wire and the needle to position distal to the takeoff of left subclavian artery 20 in the descending aorta. The constrictor is expanded, such that maximum periphery 110 of the occluder, formed by expandable ring 130, sealingly contacts the inner aortic wall. The position and orientation of the collapsed or expanded device can be checked by TEE, TTE, aortic arch cutaneous ultrasound in the emergency room, or IVUS and angiography in the angiogram suite.

The expanded constrictor is maintained during systole, during diastole, or during systole and diastole, during which blood distal to the brachiocephalic artery is forced to pass through opening 106, thereby providing a continuous partial occlusion of aortic blood flow. Alternatively, partial occlusion of aortic blood flow can be intermittent. As a result, blood flow to the descending aorta is partially diverted to brachiocephalic artery 16, left subclavian artery 20, and left carotid artery 18, thereby augmenting blood flow to the cerebral vasculature. In treating global ischemia, such as in shock, cerebral perfusion is increased by increasing blood flow through both carotid and vertebral arteries. Additionally, blood flow to the aorta is partially diverted to the coronary arteries by using the occlusion device, thereby augmenting flow to the coronary arteries. Using the partial occlusion methods during systemic circulatory failure may, therefore, improve cardiac performance and organ perfusion. By selectively increasing cerebral and coronary blood flow in this manner, the dosage of commonly used systemic vasoconstrictors, such as dopamine and norepinephrine, may be reduced or eliminated.

Figure 33B:
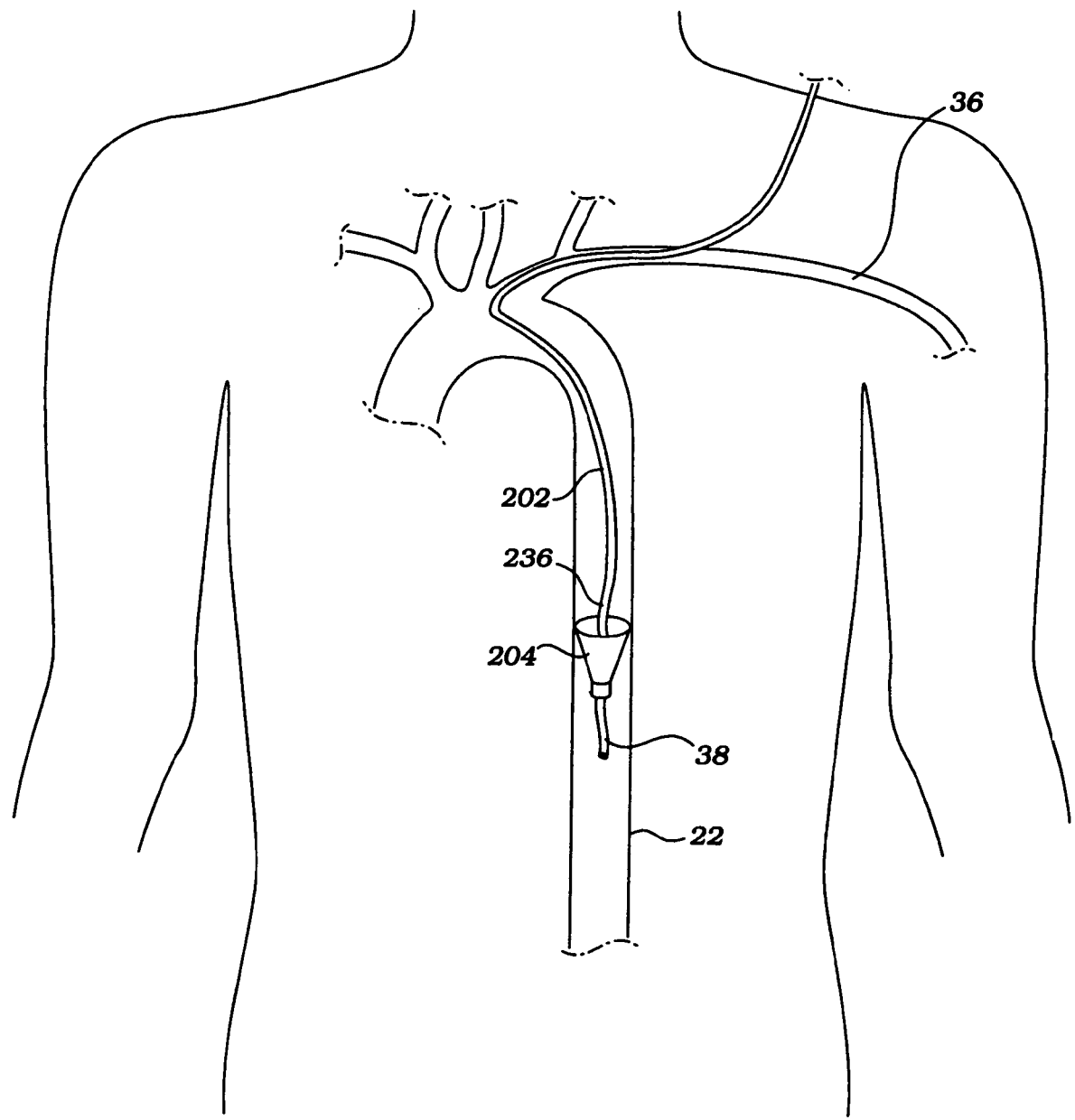
FIG. 33B illustrates the constrictor of FIG. 26 inserted in the aorta downstream from the left subclavian artery and partially occluding aortic blood flow.

Alternatively, the device of FIG. 26, much like the device used to extinguish the flame of a candle, can be introduced through an incision on left subclavian artery 36 as depicted in FIG. 33B. Constrictor 204 is inserted in aorta 22 distal to the takeoff of the left subclavian artery to provide partial, variable, and/or continuous aortic occlusion and is advanced antegrade into the descending aorta. This device is particularly useful in situations where peripheral incision cannot be made on the femoral arteries due to arteriosclerosis, thrombosis, aneurysm, or stenosis. The device may alternatively be inserted into the left or right brachial, left or right subclavian, left or right radial arteries, and then advanced into the aorta. It will be understood that these alternative approaches do not require a stiffening mandrel because the device is under tension rather than compressive loading. Any of the devices described herein can be used in these alternative approaches. These alternative approaches may also permit devices that are more flexible and smaller in diameter.

The devices and methods described in FIGS. 33A and 33B are useful in treating stroke patients within few minutes of stroke symptom, and the treatment can be continued up to 96 hours or more. For example, in treating focal ischemia due to a thromboembolic occlusion in the right internal carotid artery the constrictor may be position distal to the takeoff of the left subclavian. As a result, blood flow is diverted to brachiocephalic artery 16 and left CCA to augment both ipsilateral and contralateral collateral circulation by reversing direction of flow across the Circle of Willis, i.e., increasing flow in the right external carotid artery and left common carotid artery. The collateral cerebral circulation is further described in details in U.S. Pat. No. 6,165,199, incorporated herein by reference.

Figure 34:
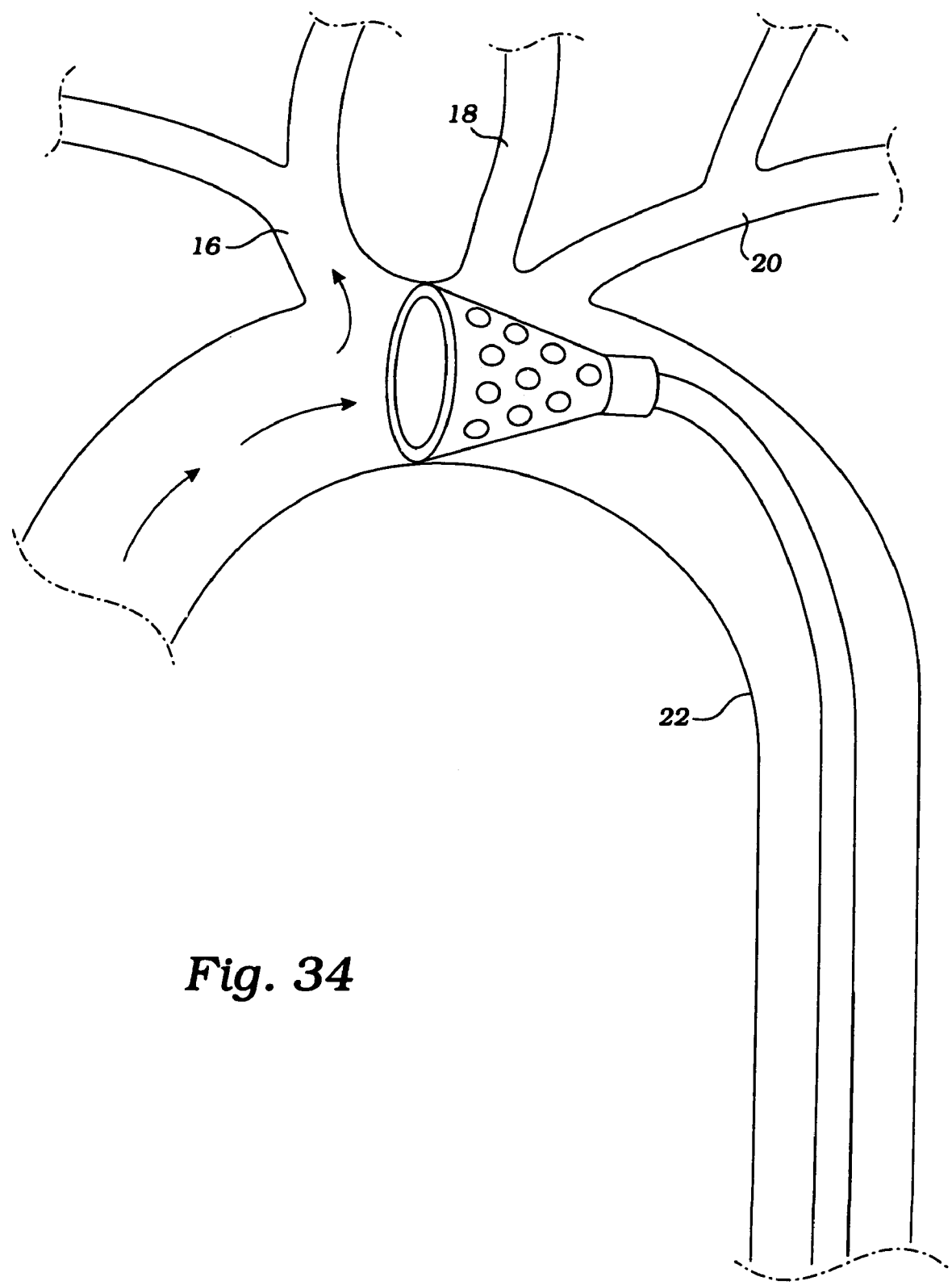
FIG. 34 illustrates the constrictor of FIG. 15 inserted in the aorta downstream from the right brachiocephalic artery and partially occluding aortic blood flow.

In treating focal ischemia due to a thromboembolic occlusion in the left internal carotid artery, for example, the constrictor can be positioned proximal to the takeoff of left carotid artery 18 and distal to the takeoff of brachiocephalic artery 16 as shown in FIG. 34. Contralateral collateral enhancement is provided by increasing flow through the brachiocephalic artery, thereby reversing blood flow in the right posterior communicating artery, right PCA, left posterior communicating artery 68 and anterior communicating artery, resulting in increased perfusion to the ischemic area distal to the occlusion and minimizing neurological deficits. Alternatively, the constrictor may be positioned distal to the takeoff of the left subclavian artery to provide both ipsilateral and contralateral collateral augmentation. Ipsilateral circulation is enhanced by increasing flow through the left external carotid artery and reversing flow along the left ophthalmic artery, both of which contribute to increased flow in the left ICA distal to the occlusion.

As a result of partially occluding aortic blood flow, blood pressure distal to the aortic occlusion may decrease, and this may result in a reduction in renal output. Blood pressure proximal the aortic occlusion will increase and may result in excessive rostral hypertension. The blood pressures, measured by the manometer, are monitored continuously, and based on this information the occlusion is adjusted to avoid peripheral organ damage. After resolution of the cerebral ischemia, the constrictor is collapsed and removed, thereby removing the aortic occlusion and restoring normal blood flow in the aorta.

Figure 35:
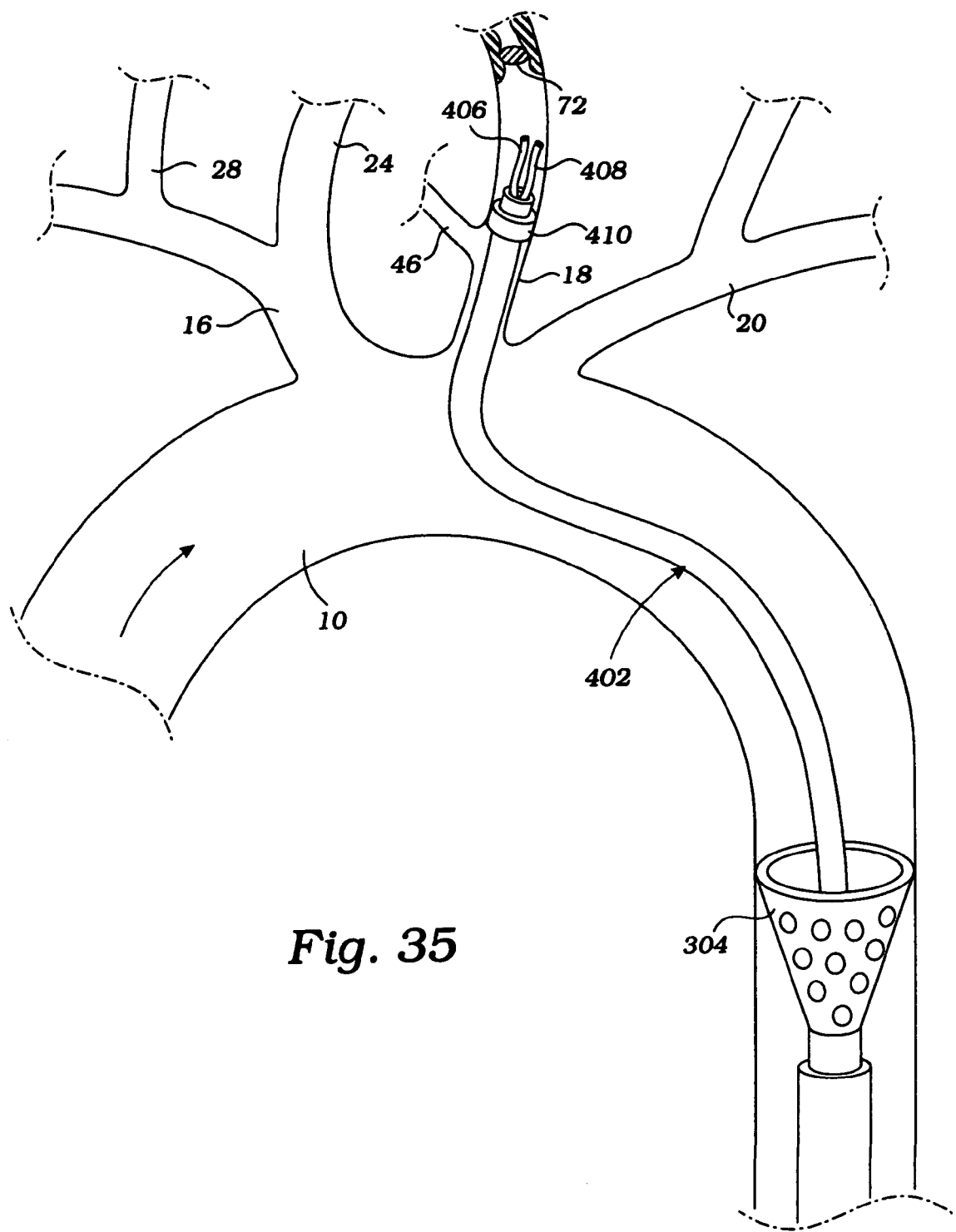
FIG. 35 illustrates a suction/atherectomy catheter introduced through the constrictor of FIG. 15 and inserted in the left carotid artery proximal to a thromboembolic occlusion.

In FIG. 35, constrictor 304 is inserted in aorta 10 and can be used to remove thromboembolic material 72 from left common carotid artery 18, while augmenting and maintaining cerebral perfusion distal to the occluding lesion. The occluder may be introduced through a guide sheath until it is positioned distal to left subclavian artery 20. In emergency situations, the constrictor can be inserted through a femoral incision in the emergency room, and atherectomy/suction catheter 402 can be inserted through the constrictor under angioscopic vision in the angiogram suite after the patient is stabilized hemodynamically. The atherectomy/suction catheter, which includes expandable balloon 410, distal aspiration port 406, and atherectomy device 408, is introduced through opening 306 until its distal end is positioned in left common carotid artery 18 proximal to the thromboembolic occlusion.

Constrictor 304 is then expanded to partially occlude aortic blood flow, thereby increasing perfusion to the ischemic region distal to the occluding lesion by enhancing ipsilateral collateral flow through left external carotid artery 46 and left vertebral artery 34 and contralateral collateral flow to right carotid artery 24 and right vertebral artery 28. The variable flow mechanism of constrictor 304 can be adjusted to control blood flow to the cerebral vasculature and the blood pressure. Balloon 410 of catheter 402 is expanded in the left common carotid artery, thereby creating a closed chamber between constrictor 410 and the thromboembolic occlusion. Suction can be applied to aspiration port 406 to create a negative pressure in the closed chamber, thereby increasing the pressure differential across the thromboembolic occlusion, which may dislodge the occluding lesion onto the aspiration port and remove the occluding lesion. Thromboembolic material 72 may be further removed by atherectomy device 408. The methods herein can also be used to remove thromboembolic occlusion in the vertebral artery. The occlusion device 304, therefore, not only augments cerebral perfusion in patients suffering from focal stroke or global ischemia, but also maintains cerebral perfusion while waiting for invasive or noninvasive intervention. The devices and methods of using atherectomy/suction catheter 102 are further described in U.S. Pat. No. 6,165,199, incorporated herein by reference.

Figure 36:
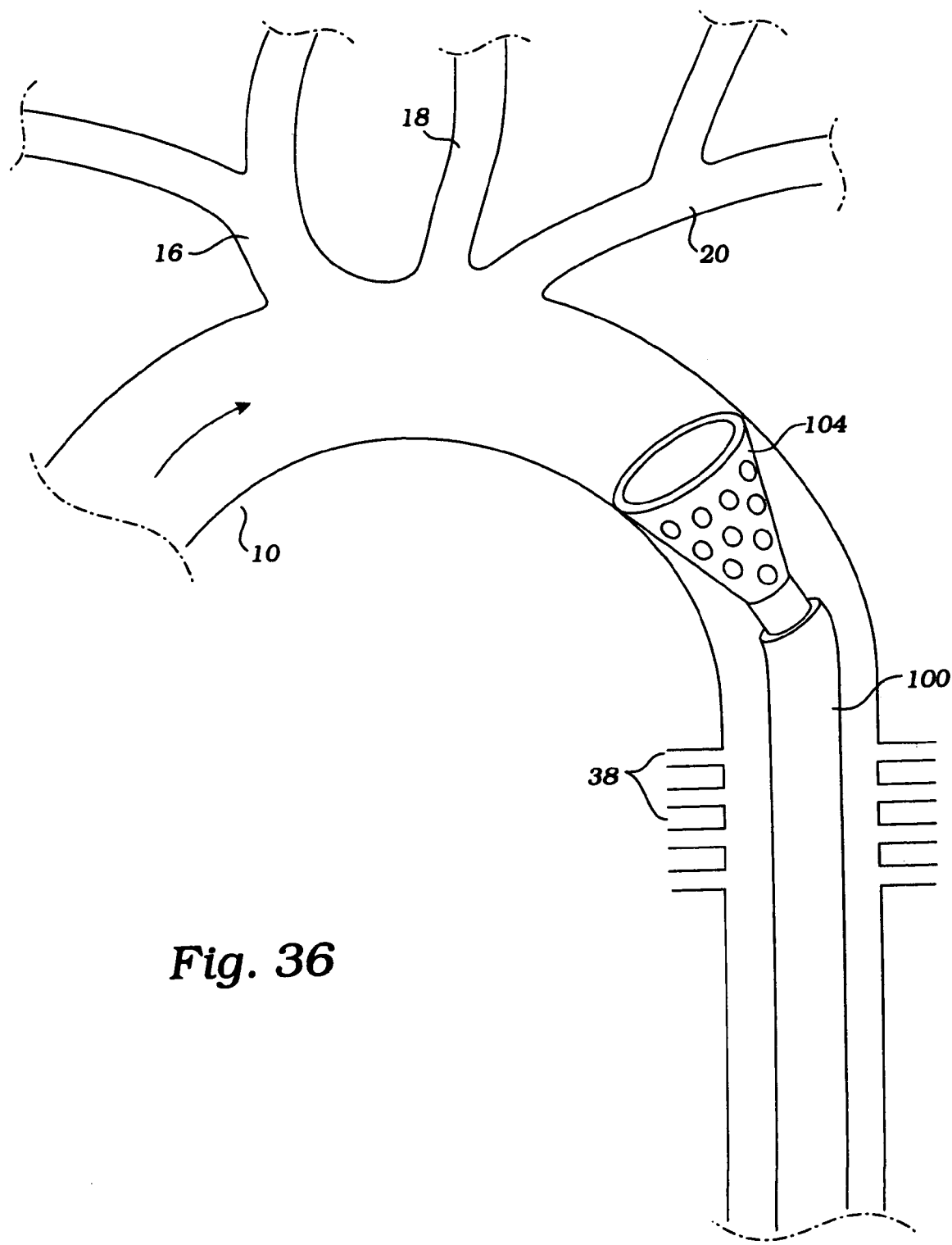
FIG. 36 illustrates the constrictor of FIG. 15 inserted in the aorta upstream from the lumbar or lumbar or spinal arteries.

During abdominal aortic aneurysm (AAA) surgery, lumbar or spinal arteries, which provide blood supply to the spinal cord, are often dissected away from the diseased abdominal aorta, resulting in reduction of blood flow to the spinal cord. The devices herein disclosed may be used to condition the spinal cord prior to AAA repair, thereby reducing the damage resulting from spinal ischemia during surgery. In FIG. 36, constrictor 104 is inserted in aorta 10 and expanded preferably distal to left subclavian artery 20 and proximal to lumbar arteries 38. As a result, blood flow to the lumbar or spinal arteries is reduced. When this device is used in patients anticipating a major thoracoabdominal surgery, such as AAA repair, approximately 24 hours prior to surgery, blood flow to the lumbar arteries can be intentionally reduced to induce mild spinal ischemia, thereby conditioning the spinal cord to produce neuroprotective agents which may protect the spinal cord from more significant ischemic insult during surgery.

Figure 37:
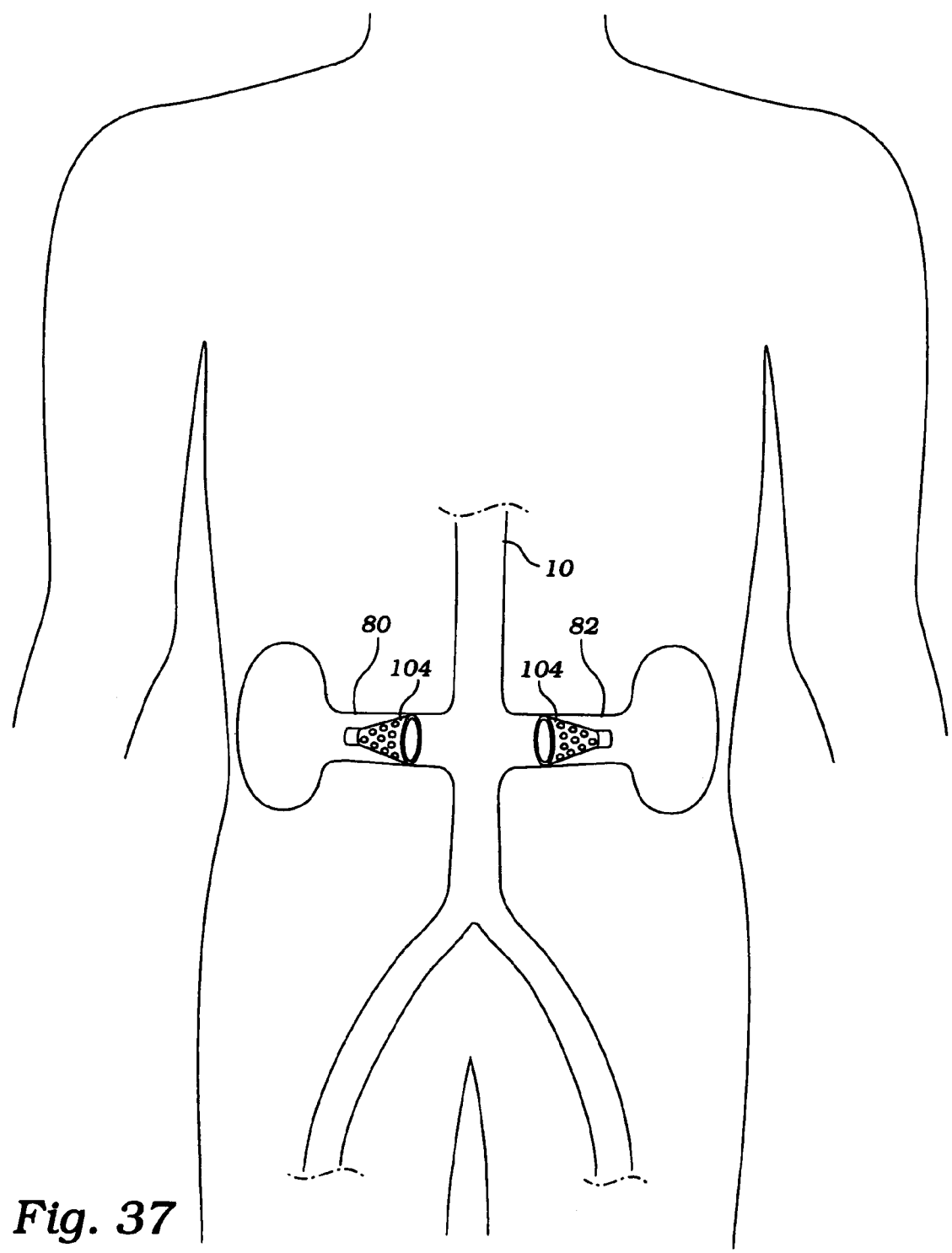
FIG. 37 illustrates the constrictor of FIG. 15 inserted in the renal arteries.

In hypertension, end organ damage often results, e.g., cardiac, renal, and cerebral ischemia and infarction. The devices and methods herein may be employed in hypertension to protect the kidneys from ischemic insult. In FIG. 37, constrictors 104, which can be introduced through a femoral artery, are inserted in right renal artery 80 and left renal artery 82. The constrictors are expanded to partially occlude blood flow from descending aorta 10 to the renal arteries, thereby reducing blood pressure distal to the occlusion. The constrictors can be deployed for the duration of any systemic hypertensive condition, thereby protecting the kidneys from damage that might otherwise be caused by the hypertension.

In another embodiment, the constrictor will be provided with capabilities for mounting on a standard catheter, e.g., a standard angioplasty balloon catheter, a stent deployment catheter, an ultrasound catheter, or an atherectomy catheter. Such a device having capabilities for removable mounting on a standard catheter is depicted in FIGS. 44A-44H. The constrictor shown in FIG. 44A includes elongate tubular member 601 having lumen 605 for passage of blood extending from a proximal to a distal end of tubular member 601. The device includes constrictor 602, here a balloon mounted on tubular member 601 and communicating with inflation lumen 603. Inflation lumen 603 extends proximal, and extends through the incision in the patient so that it remains operable outside the patient's body. Tubular member 601 is constructed of a flexible and deformable material so that inflation of balloon 602 causes a reduction in the cross-sectional diameter of lumen 605 as shown in FIG. 44B to reduce blood flow.

In use, tubular member 601 is positioned in the descending aorta and balloon 602 is inflated the outer diameter of balloon 602 expands until it engages the lumen of the descending aorta. Further inflation of balloon 602 will cause deformation of tubular member 601 to thereby reduce lumenal diameter 605. In this manner, peripheral blood flow is reduced, resulting in an increase blood pressure upstream of the device. Because the device shown in FIGS. 44A and 44B is mounted on a standard catheter (not shown), the standard catheter having diagnostic or therapeutic capabilities extends beyond tubular member 601 and may access any of the coronary arteries, carotid arteries, or any other vessels upstream of the descending aorta.

Figure 44A:
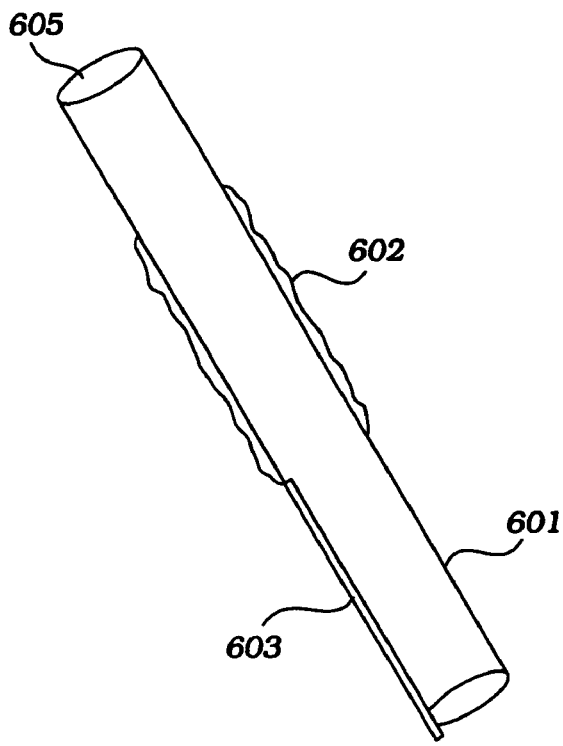
FIG. 44A depicts an embodiment of a constrictor that can be removably mounted on a standard catheter.
Figure 44B:
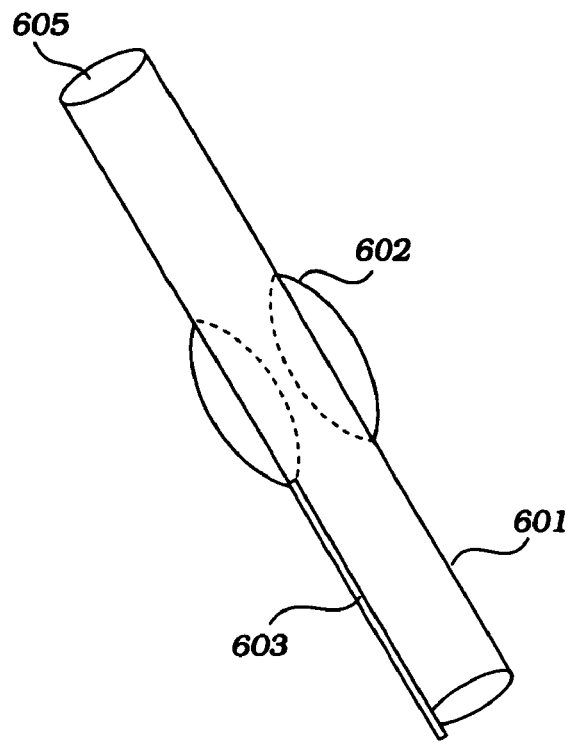
FIG. 44B depicts the inflated constrictor of FIG. 44A.
Figure 44C:
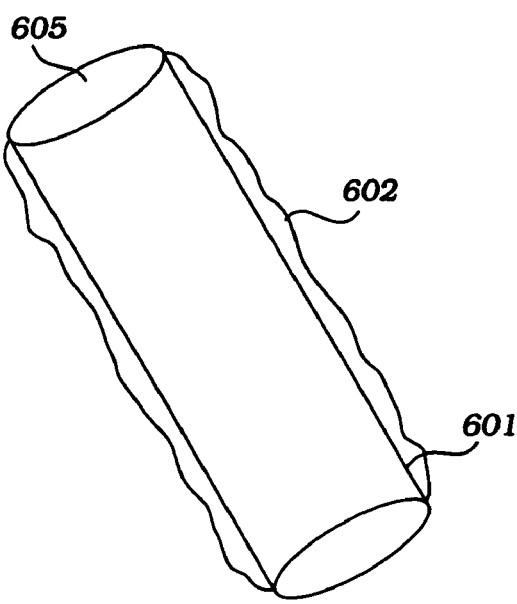
FIG. 44C depicts another embodiment of a constrictor that can be removably mounted on a standard catheter.
Figure 44D:
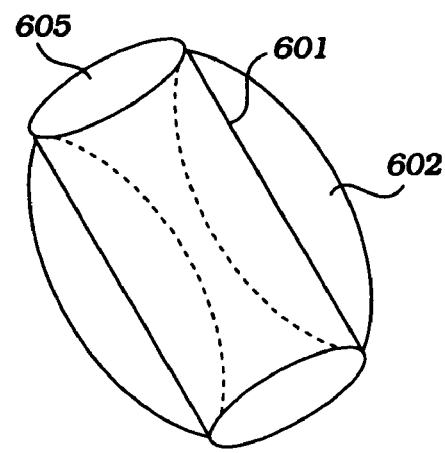
FIG. 44D depicts the inflated constrictor of FIG. 44C.

FIG. 44C depicts an alternative mountable constrictor having a shortened tubular member 601, shortened by comparison with tubular member 601 shown in FIG. 44A. FIG. 44D shows the constrictor of FIG. 44C with balloon 602 inflated. It should be noted that inflation of balloon 602 proceeds until the outer diameter of balloon 602 engages the lumen of the aorta, whereupon further inflation causes deformation of tubular member 601 inwardly to reduce the diameter of lumen 605, thereby constricting blood flow.

In another embodiment, a removably mountable constrictor is provided as depicted in FIGS. 44E and 44F. Referring to FIG. 44E, balloon constrictor 602 communicates with a proximally extending inflation lumen (not shown), and balloon 602 includes first lumen 620 for passage of blood, second lumen 615 for passage of a standard catheter, and manometer 610. Blood flow lumen 620 is equipped with deformable walls 621, shown in FIG. 44F at three different levels of deformation. Lumen 615 is shaped to receive a standard catheter (angioplasty, stent, ultrasound, or atherectomy). Lumen 615 is also equipped with a locking mechanism, shown here as first and second flexible clips 630 mounted at a position along lumen 615. In use, clips 630 are operated to clear a passage for advancement of a standard catheter through lumen 615. The clips are then released to frictionally engage the catheter and thereby ensure that the constrictor maintains a fixed position along the catheter.

In another embodiment shown in FIGS. 44G and 44H, elongate tubular member 601 having lumen 605 is constructed of a flexible deformable material. Spring 635 is disposed about an intermediate portion of tubular member 601. Spring 635 is operable between a relaxed configuration (FIG. 44H) and a constricted configuration (FIG. 44G). The spring is operable by way of an actuating mechanism, such as a cinch strap.

Figure 45A:
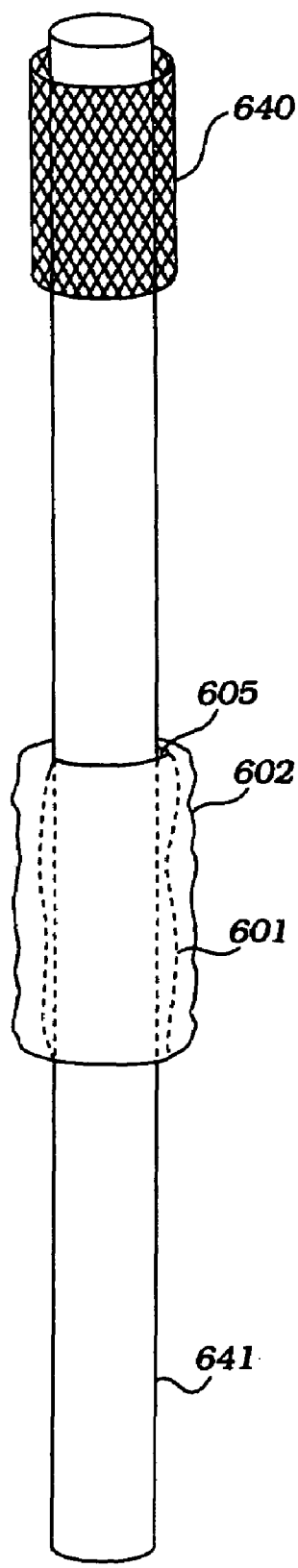
FIG. 45A depicts a constrictor mechanism mounted on a stent deployment catheter.
Figure 45B:
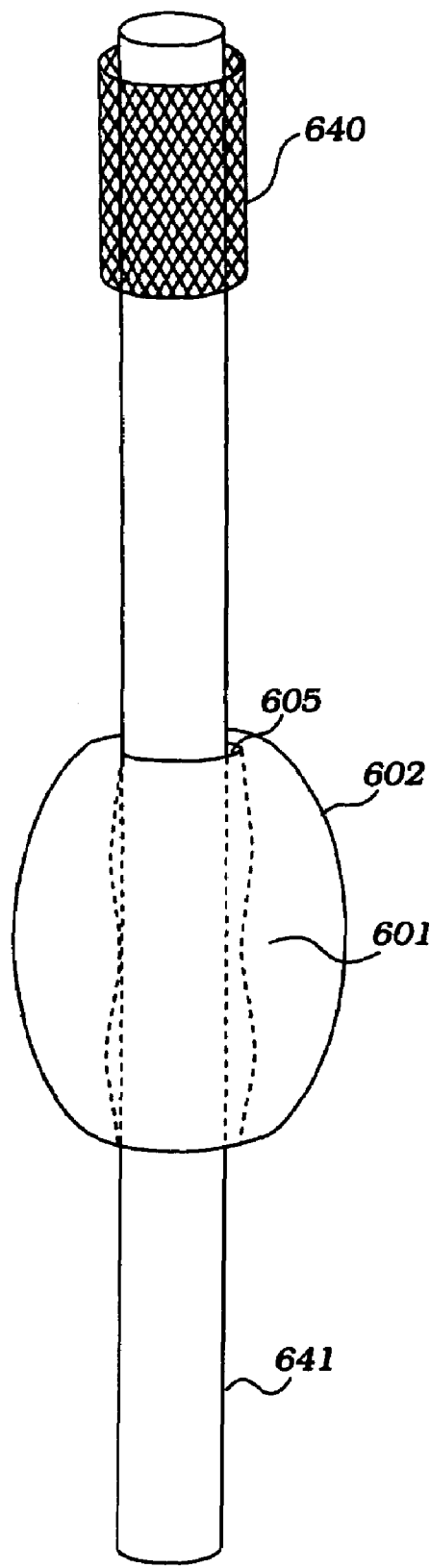
FIG. 45B depicts the catheter and constrictor of FIG. 45A with the constrictor expanded.

A stand alone coarctation device as depicted in any of FIGS. 44A-44H can be mounted on a standard catheter as depicted in FIGS. 45A and 45B. Catheter 641 in FIGS. 45A and 45B carries stent 640 at a distal end of catheter 641. In other embodiments the catheter may carry an angioplasty balloon, an atherectomy device, and/or intravascular ultrasound capabilities. Catheter 641 passes through lumen 605 of elongate tubular member 601. Catheter 641 is releasably engaged by tubular member 601 in a manner that allows open space for passage of aortic blood through lumen 605. Balloon 602 is mounted circumferentially about tubular member 601. In use, balloon 602 is inflated to engage the lumen of the aorta, and further inflation constricts the diameter of lumen 605, thereby reducing aortic blood flow. Tubular member 601 is constructed of a deformable material that allows inward flexing upon further inflation of balloon 602.

Figures 46A, 46B:
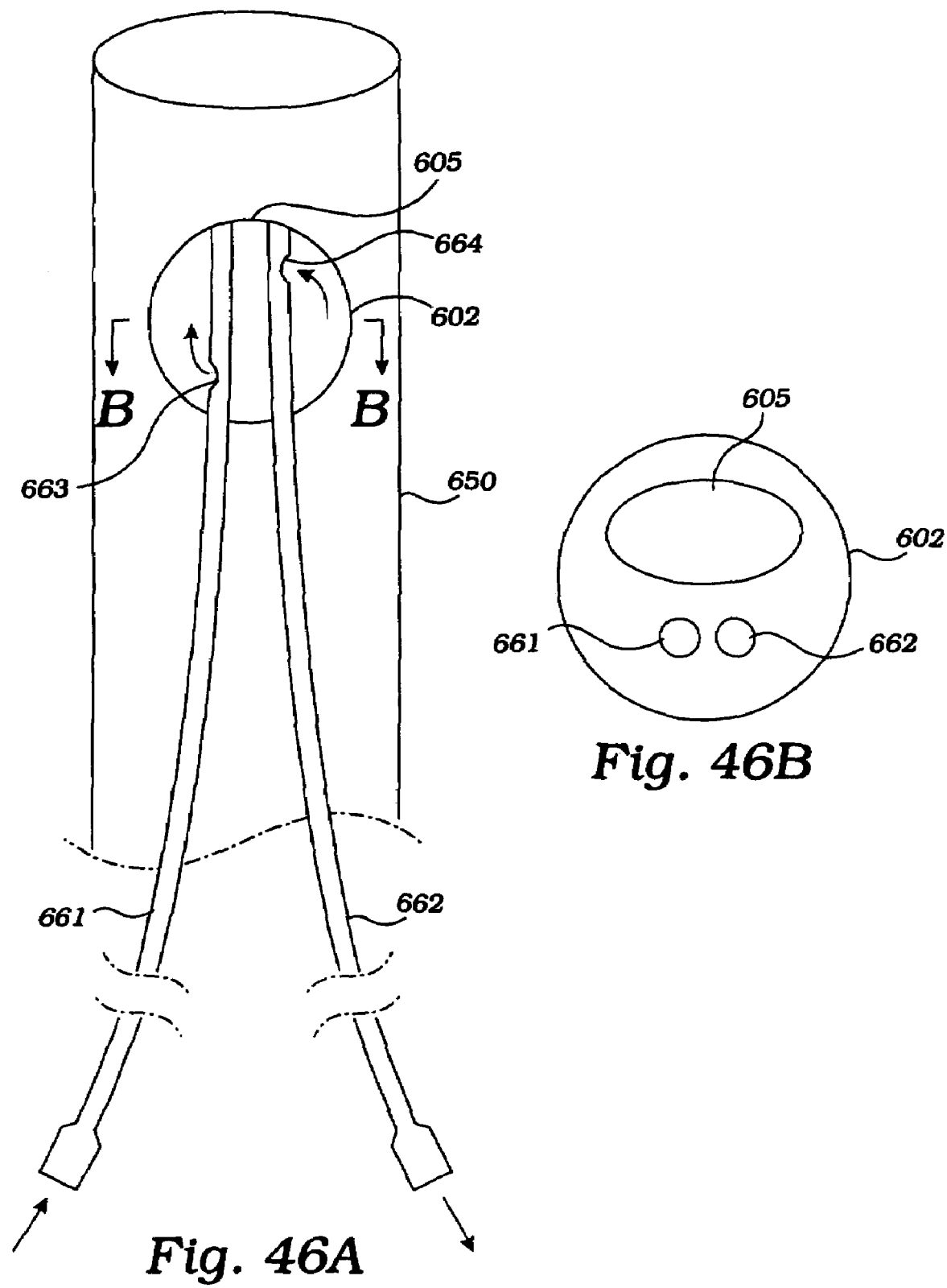
FIG. 46A depicts another embodiment of a constrictor having an introducer sheath and an inflatable balloon catheter within the sheath.
FIG. 46B depicts a cross-sectional view of the catheter of FIG. 46A through sectional line B-B.

A balloon having capabilities for purging gas is depicted in FIGS. 46A and 46B. Introducer sheath 650 is disposed about balloon 602 to facilitate entry into a major vessel, e.g., a femoral artery. Balloon 602 communicates with first catheter 661 and second catheter 662, both having a lumen extending to outside the patient's body. Saline is injected through catheter 661 and fills balloon 662 through infusion port 663. Any gas within balloon 602 is purged through port 664 until balloon 602 is entirely filled with saline. Air passes through catheter 662 and exits the patient's body. Catheter 662 is then sealed, allowing balloon 602 to be inflated upon infusion of additional saline. Blood flow lumen 605 is surrounded by a deformable wall. Balloon expansion engages the lumen of the aorta, and further expansion reduces the diameter of blood flow lumen 605, increasing blood pressure upstream of the coarctation device. FIG. 46B shows a cross-section of the catheter taken through the balloon.

Figure 47A:
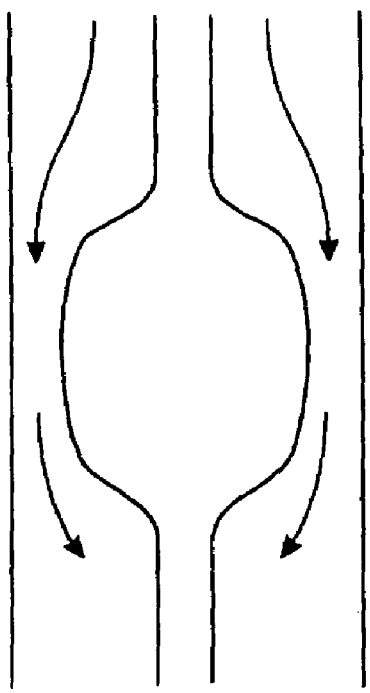
FIG. 47A depicts a mechanism for partial obstruction of the aorta.
Figure 47B:
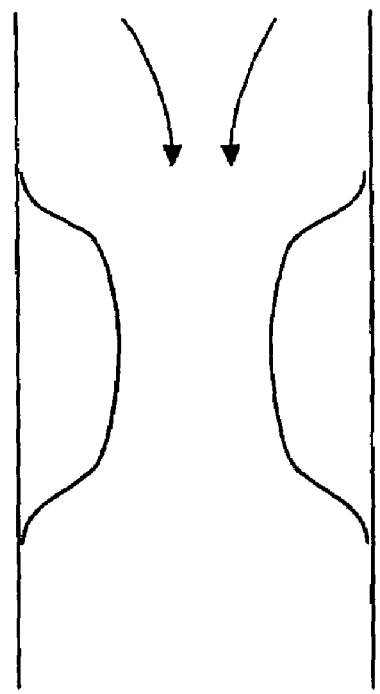
FIG. 47B depicts another mechanism for partial obstruction of the aorta.
Figure 47C:
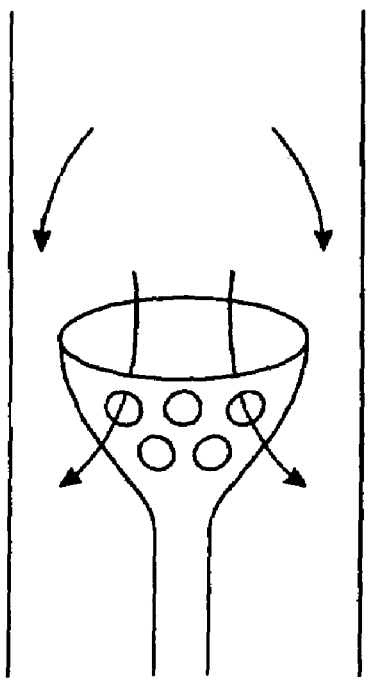
FIG. 47C depicts another mechanism for partial obstruction of the aorta.
Figure 47D:
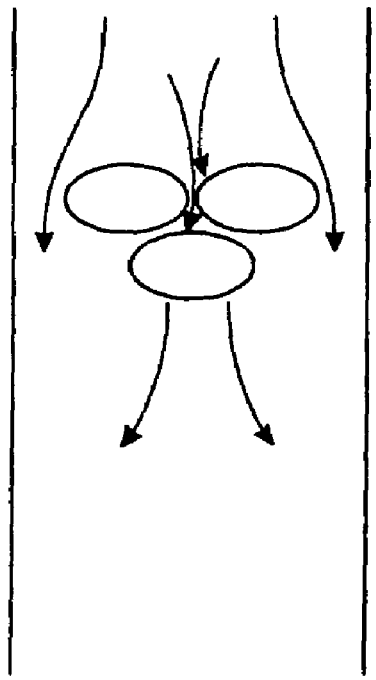
FIG. 47D depicts another mechanism for partial obstruction of the aorta.

FIGS. 47A-47D depict alternative arrangements for partial aortic obstruction as contemplated herein. FIG. 47A shows a device that expands radially outward, and where blood flows around the expandable member. FIG. 47B shows a device that expands inward, and where blood flows through the expandable member. FIG. 47C shows a device that expands outward, and where blood flows through ports in the expandable member. FIG. 47D shows a device that expands outward, and where blood flows both through and around the expandable members.

Figures 48, 48A:
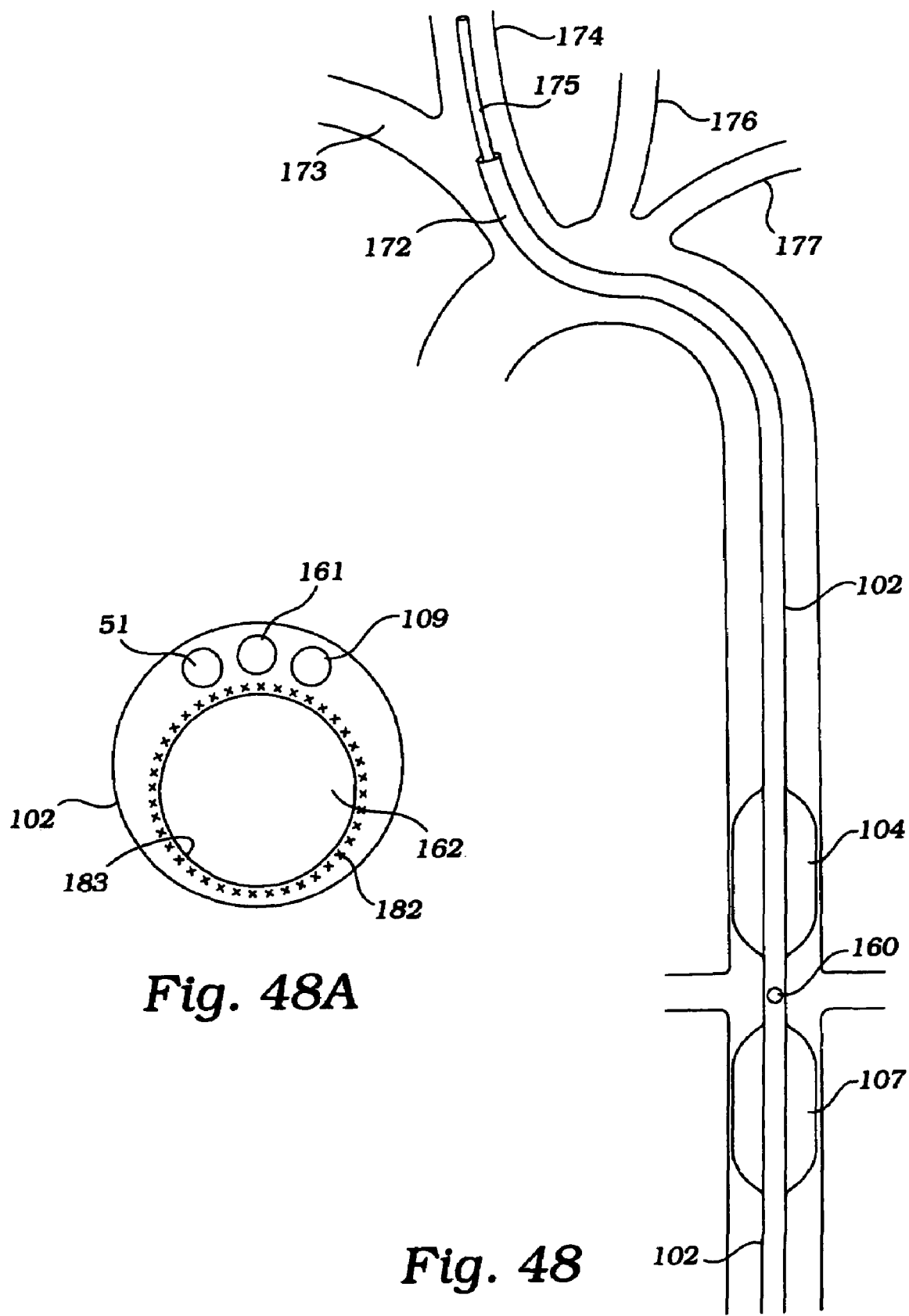
FIG. 48 depicts another embodiment of the devices constructed according to the present invention for providing partial occlusion of a vessel.
FIG. 48A depicts a cross-sectional view of the catheter of FIG. 48.

FIG. 48 depicts a device that can be used as an adjunctive treatment when combined with other technology to treat stroke. Catheter 102 includes flexible distal region 172 adapted to access cranial vasculature. Catheter 102 includes a through lumen to pass interventional devices, e.g., microinfusion catheters, pressure wires, stent catheters, angioplasty catheters, atherectomy devices, pharmaceuticals, cooling mechanisms, and alike. Distal end 172 is sufficiently long to reach the vessels of the upper aortic arch. The occlusion mechanism may comprise any of a variety of expandable members as described in the various embodiments herein. Catheter 102 is shown in cross-section in FIG. 48A. The catheter includes pressure lumen 161, proximal balloon inflation lumen 51, and distal balloon inflation lumen 109. Main lumen 162 is, in certain cases, Teflon lined at surface 183, and 0.060 inches. Braid 182 reinforces catheter 102.

In use, as shown in FIG. 48, catheter 102 is positioned with balloon 104 suprarenal, balloon 107 infrarenal, and pressure port 160 in between. The distal end 172 extends into the right brachiocephalic artery. Interventional instrument 175 passes through the lumen of catheter 102 and is directed into right common carotid artery 174 for the purpose of treating a lesion. Distal end 172 of catheter 102 may alternatively access right subclavian artery 173, the right vertebral artery, the right internal carotid artery, the right external carotid artery, left common carotid artery 176, the left internal carotid artery, the left external carotid artery, left brachiocephalic artery 177, and/or the left vertebral artery.

Figure 48B:
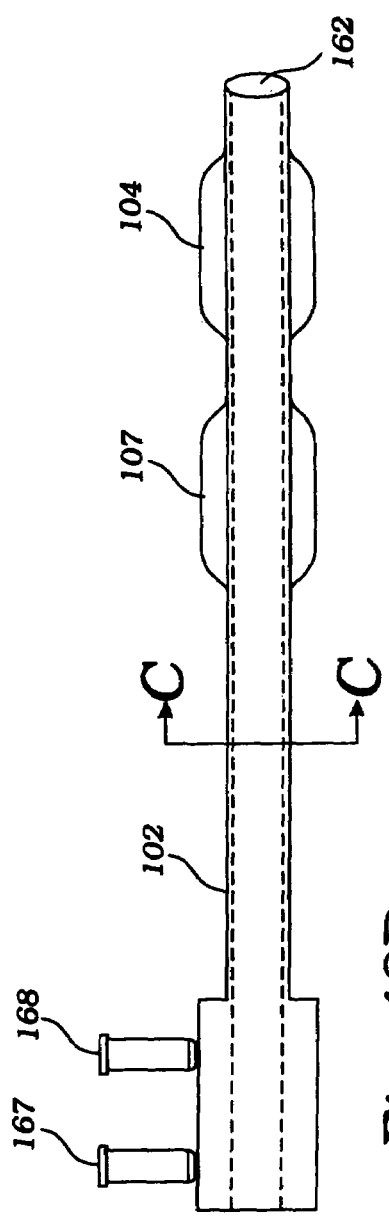
FIG. 48B depicts another embodiment of the devices constructed according to the present invention for providing partial occlusion of a vessel.
Figure 48C:
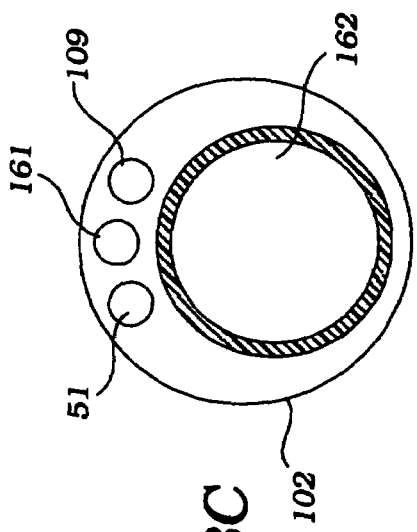
FIG. 48C depicts a cross-sectional view of the catheter of FIG. 48B.
Figure 48D:
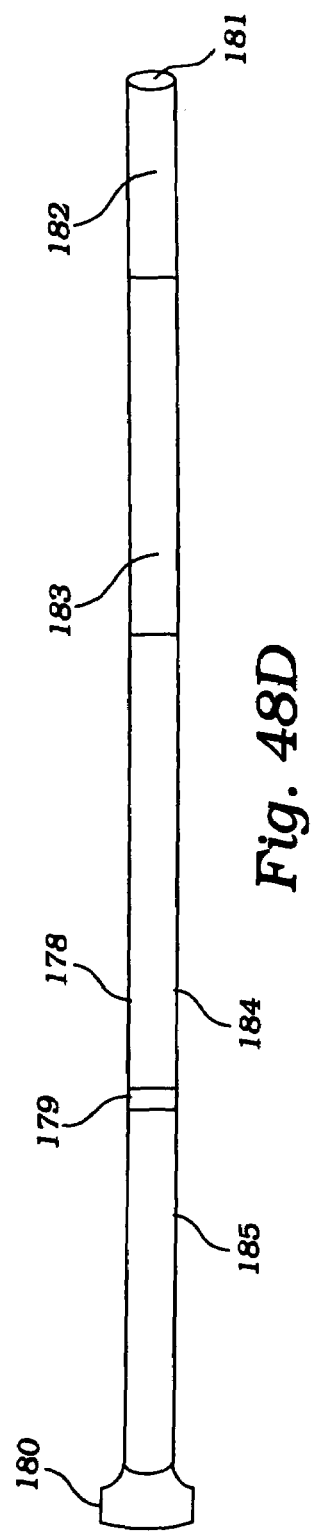
FIG. 48D depicts a guiding catheter for use with the catheter of FIG. 48B.

FIGS. 48B-48F depict a further alternative design. FIG. 48B shows catheter 102 having sufficient strength to resist the forces applied by blood flow during partial obstruction of the aorta, yet sufficiently flexible to be easily inserted into the femoral artery and tracked into the iliac and into the aorta. FIG. 48C is a cross-sectional view of catheter 102. FIG. 48D shows guiding catheter 178 with varying stiffness along its length. Distal most region 182 is soft, flexible and atraumatic. Intermediate region 183 is a transitionary stiffness zone for introduction into the body. Proximal region 185 is very stiff and stabilizes the system. Bond 179 marks the insertion interface. Guiding catheter 178 is slideably interfaced into lumen 162 of catheter 102 depicted in FIG. 48B. The catheter 102 of FIG. 48B is, in certain cases, 8 F compatible and approximately 70 cm in length. The guiding catheter 178 shown in FIG. 48D is, in certain cases, a 5 F catheter and approximately 100-120 cm in length to facilitate placement in the cerebral vasculature. The foregoing ranges are set forth solely for the purpose of illustrating typical device dimensions. The actual dimensions of a device constructed according to the principles of the present invention may obviously vary outside of the listed ranges without departing from those basic principles.

In use, guiding catheter 178 is inserted into lumen 162 of catheter 102 until indicator band 179 is flushed with manifold 186 shown in FIG. 48E. A guidewire is placed within the aorta near the aortic arch. The assembled device of FIG. 48E is then tracked over the guidewire. Contrast media can be injected through guiding catheter 178 to aid positioning the device. Notably, the transitionary stiffness zone is within catheter 102 when assembled as shown in FIG. 48E. When catheter 102 is properly positioned in the descending aorta, guiding catheter 178 is further advanced up the descending aorta to engage a separate vasculature, e.g., coronary, carotid, or cerebral vasculature. Alternatively, at least partial obstruction of the aorta to increase cerebral blood flow may begin with the assembly as delivered, and at a later time guiding catheter 178 may be advanced.

EXAMPLE 1

In order to study the efficacy of the coarctation devices disclosed herein, an experiment was conducted using rats. The rat was placed under anaethesia, and an incision was made over one or more of the carotid arteries. The middle cerebral artery was ligated and the CCA was clamped using a hemostat to abolish blood flow to the ipsilateral cerebral hemisphere, thereby inducing a stroke. The aorta was then ligated, thereby causing immediate and sustained elevation in the systolic blood pressure (SBP), diastolic blood pressure (DBP), and mean arterial pressure (MAP) proximal to the constriction. It was found that the ligation tended to produce doubling of MAP.

Figure 38:
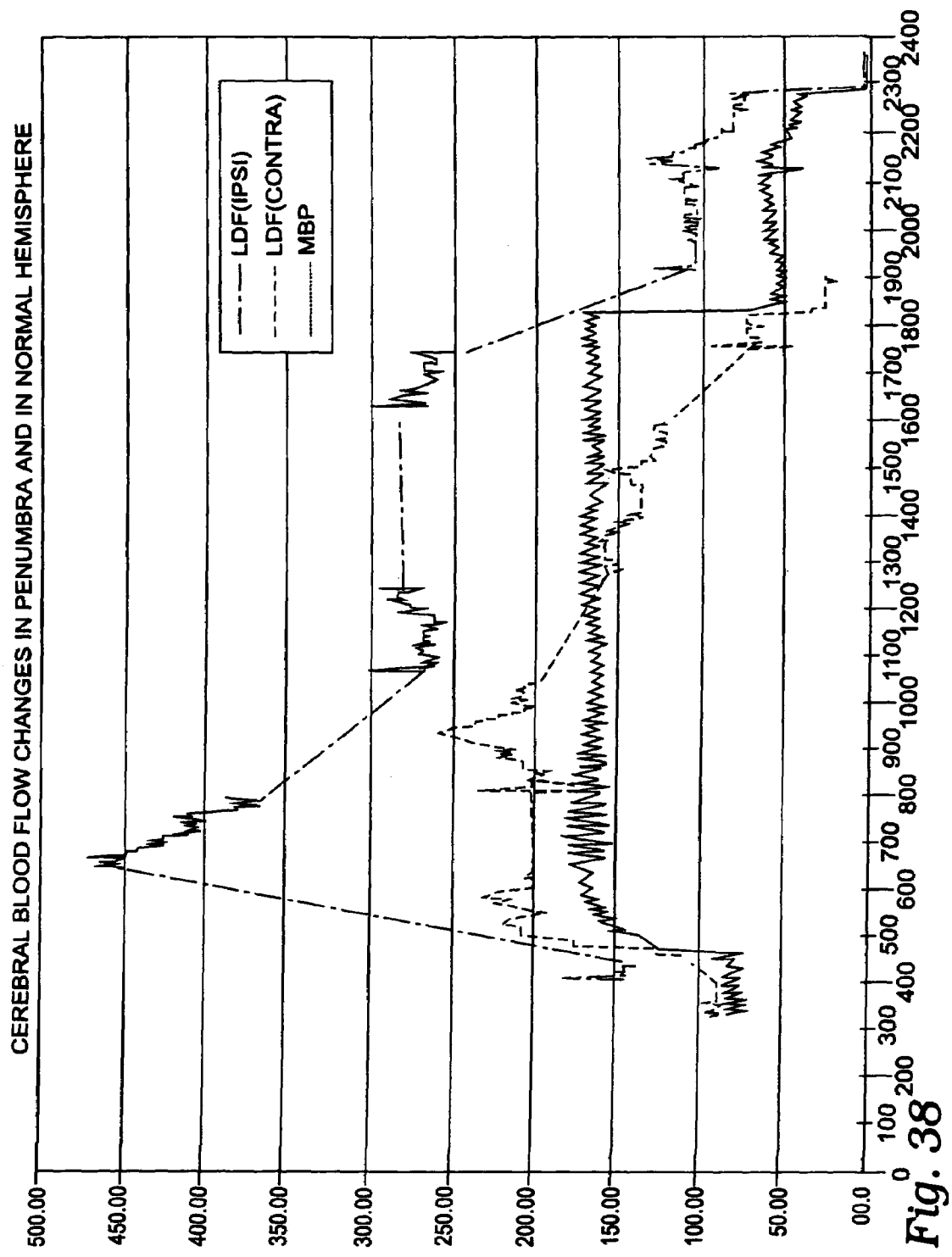
FIG. 38 depicts a graph of cerebral blood flow versus time in a stroke induced rat brain.

FIG. 38 shows a plot of cerebral blood flow (cc blood/100 grams brain tissue/min) versus time (minutes) in a rate stroke model. Cerebral blood flow (CBF) can be measured using Laser Doppler Flow (LDF) measurement. As shown in FIG. 38, IPSI refers to the cerebral hemisphere where the stroke was induced, CONTRA refers to the cerebral hemisphere where the stroke was not induced (i.e., normal brain), and MBP refers to the mean blood pressure proximal to the aortic occlusion.

At "initiation," the descending aorta was ligated. CBF is shown in FIG. 38 to increase immediately following aortic ligation as indicated by the rise in MBP. The rise in CBF can be seen at any level of placement of the ligation in the descending aorta, e.g., infrarenally or suprarenally. Infrarenal placement of the coarctation devices may be preferred since renal complications associated with occlusion of the renal blood supply are minimized, and prolonged use of the devices in stroke patients is permitted. The increased CBF tended to fall over a forty-minute time period in some animals.

The CBF in the ipsilateral hemisphere is also shown in FIG. 38 to increase immediately following ligation. Ipsilateral CBF on ligation increased by approximately two times. The fact that any increase is observed here is an unexpected result because this region of the brain represents the penumbra of the stroke. A five fold increase CBF in the core of the stroke was also observed. This was highly unexpected. The increased ipsilateral CBF tends to fall in some animals over a forty-minute time period as well.

The CBF in the contralateral hemisphere is also shown to increase immediately following aortic ligation, as high as up to 500% of baseline value. The increased contralateral CBF also tends to fall over a forty-minute time period. The increase in perfusion was so marked that the devices described herein may only need to be inflated very minimally, and the degree of inflation varied with time.

After "termination," CBF is shown in FIG. 38 to fall immediately after ligation is released as indicated by the fall in MBP. The CBF in the ipsilateral and contralateral hemispheres are also shown in FIG. 38 to fall immediately after ligation is released.

It was also noted that release followed by re-ligation of the aorta reproduced the desired increase in CBF, even when the sequence was repeated several times. Thus, changes in MAP induce a hyperperfusional state best maintained by periodic re-inflation of the device (e.g., twenty-minute periods of inflation with a few seconds of deflation in between as in the case for prolonged use of the coarctation device). One hour of coarctation may be sufficient in treatment of stroke, and thus repeated inflations would not be needed. Cerebral autoregulation during aortic ligation was clearly overridden in this model. It is conceivable that autoregulatory curves are quite different when blood pressure and CBF are increased using aortic constriction as compared to those obtained using injection of epinephrine, a cerebral vasoconstrictor.

This example further explains the important differences between aortic ligation as described herein versus IABP. First, SBP increases when the aorta is ligated much more than SBP increases for IABP. Second, IABP increases DBP but not SBP, and IABP pulls blood from the brain during systole. By contrast, ligation increases both DBP and SBP, and therefore increases cerebral blood flow at all times. Third, mean CBF is increased for ligation whereas mean CBF is unchanged for IABP. Ligation effectively shifts the blood pressure curve upward at all points, systole and diastole. Fourth, ligation as described herein increases blood flow in the brain during stroke by 100% or more, 200% or more, 300% or more, 400% or more, and 500% or more. IABP by contrast, has been shown to increase CBF by no more than 30-40% and in some studies has caused a decrease in CBF by 10-12%. Fifth, the occlusion produced with IABP is inadequate for the purpose of treating stroke, since the increase in cerebral perfusion is so marked during total occlusion that, the coarctation device will only need to constrict the aortic lumen, rather than occlude it.

Sixth, IABP provides sudden, jerky increases and decreases in blood pressures, since inflation or deflation is an all or none process. Deflation of IABP is associated with sudden, severe drops in MAP to below baseline values and a corresponding dramatic fall in CBF, thereby causing dangerous hypoperfusion. Cyclical deflations and inflations of IABP fail to provide a smooth and manipulable pressure proximally. The coarctation device disclosed herein incorporates a mechanism for a very slow deflation to avoid the "rebound" hypoperfusion.

Seventh, EKG linkage and external pumping are essential for the operation of IABP, but not required for the coarctation devices. Eighth, air embolization is a known complication of using IABP since air or gas is often used to inflate the balloon. The coarctation devices avoid air embolization by using liquid inflation or a spring mechanism. Tenth, spinal ischemia, aortic dissection, and renal ischemia are common complications associated with high aortic positioning of IABP, e.g., at the level of subclavian takeoff. Insertion and positioning of IABP often requires fluoroscopy in an angiogram suite. The coarctation devices, on the other hand, can be inserted either suprarenally or infrarenally. The infrarenal positioning avoids the complications associated with IABP and allows insertion of the coarctation devices in the ER without the use of fluoroscopy. Eleventh, IABP is indicated in treatment of heart failure to boost coronary perfusion. By contrast, the coarctation devices can be used in treatment of stroke and non-cardiogenic shock to boost cerebral perfusion.

EXAMPLE 2

Figure 39:
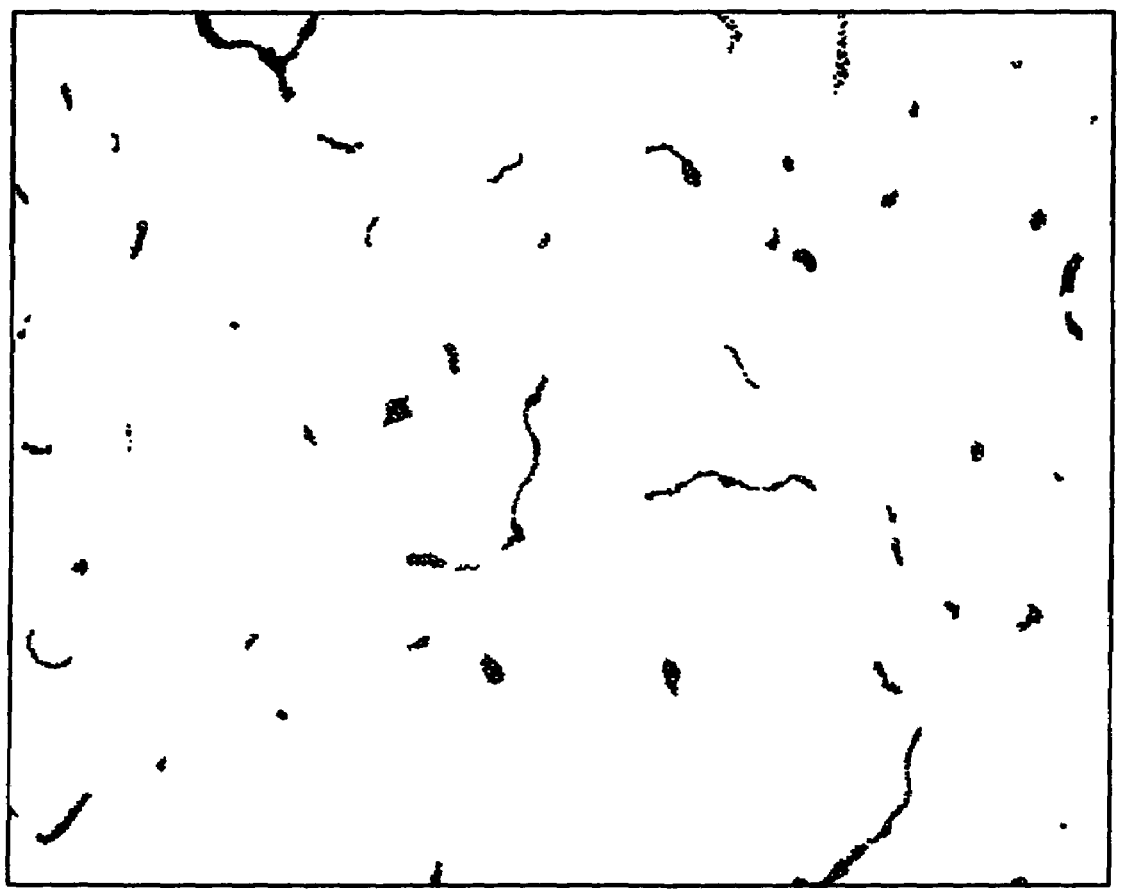
FIG. 39 depicts a fluorescent stain of a rat brain section having normal capillary perfusion.

Sections of rat brain were taken before and after deployment of the devices disclosed herein using fluorescent-labeled capillary perfusion techniques. After induction of three-vessel stroke, the rat was injected with a red dye, followed by deployment of a coarctation device, followed by injection of a fluorescent green dye that has affinity for patent capillary. The rat is then sacrificed and sections of the rat brain were taken and exposed microscopically under fluorescent light. FIG. 39 depicts a normal rat brain having numerous fluorescent staining capillaries.

Figure 40:
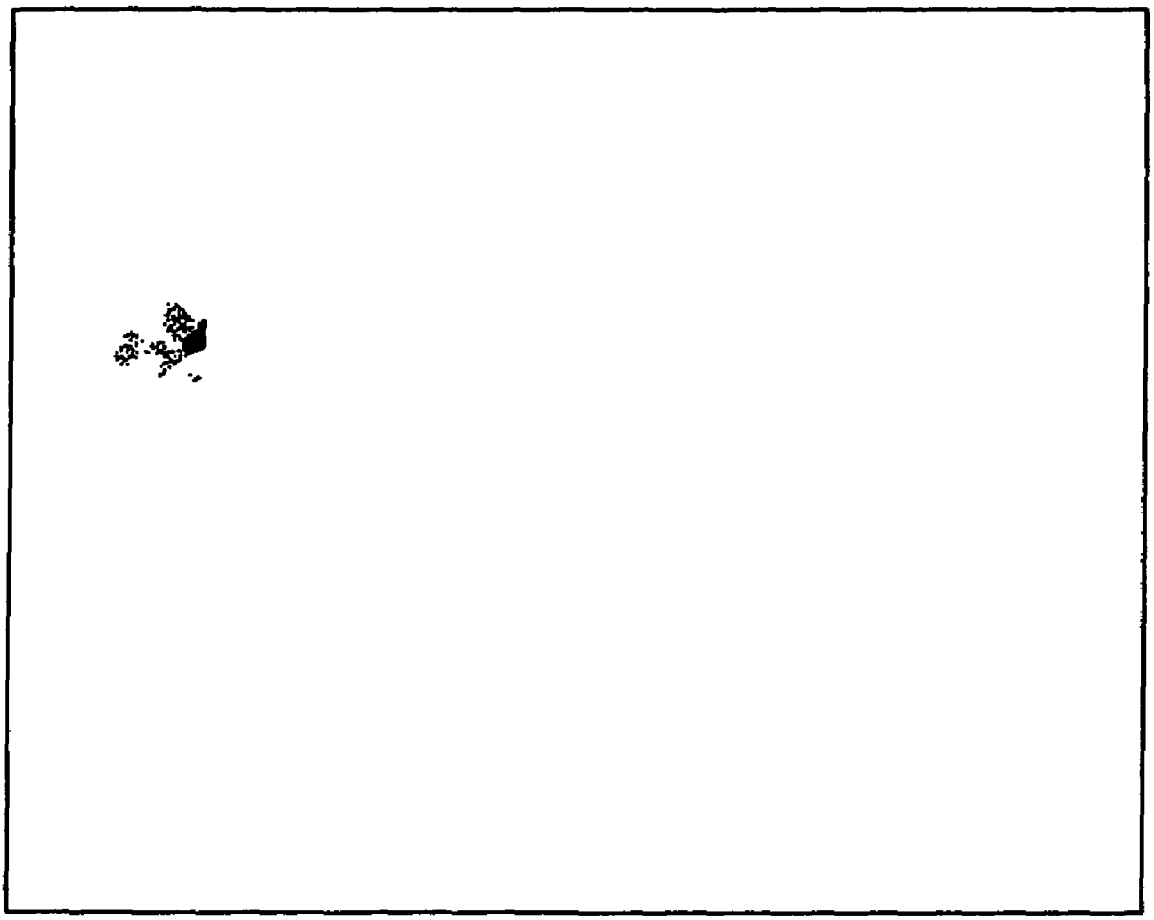
FIG. 40 depicts a fluorescent stain of the stroke center in a rat brain section after induction of stroke.
Figure 41:
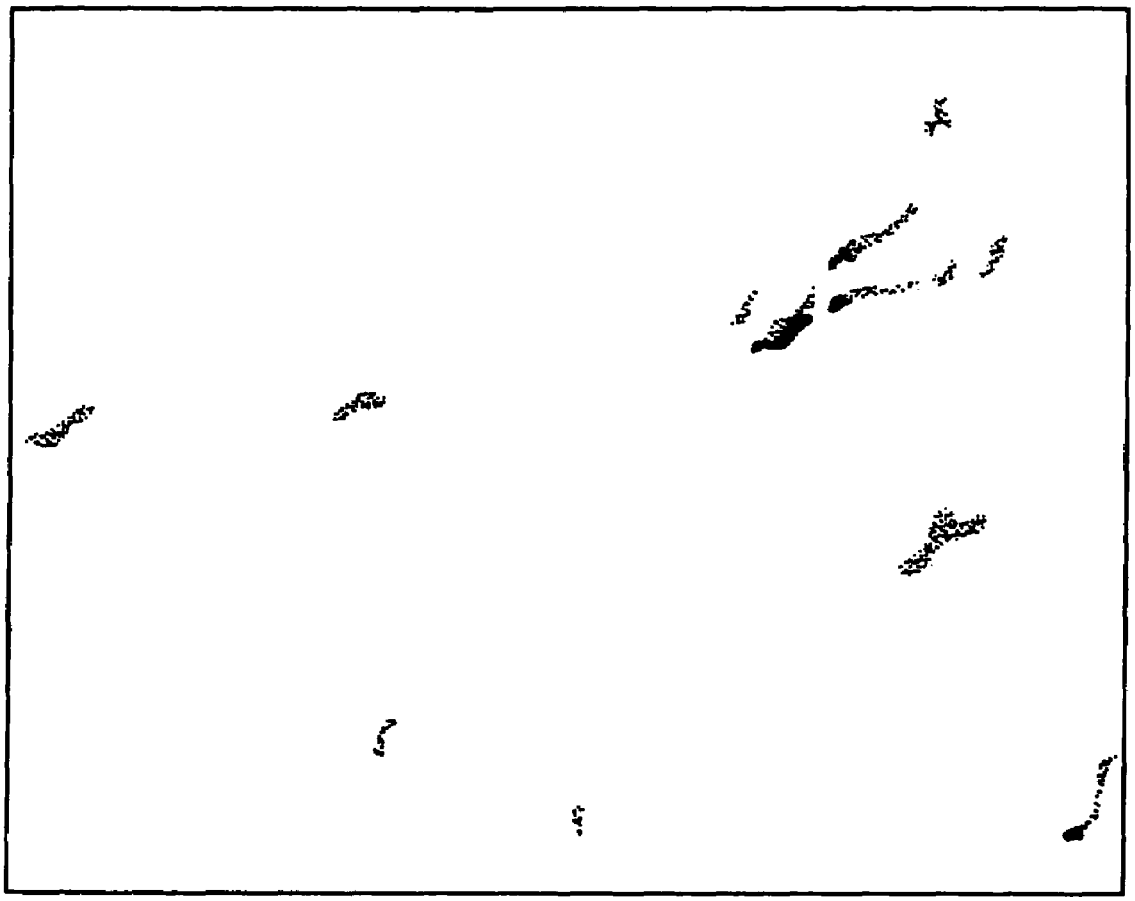
FIG. 41 depicts a fluorescent stain of the stroke penumbra in a rat brain section after induction of stroke.
Figure 42:
FIG. 42 depicts a fluorescent stain of the stroke center in a rat brain section after placement of a coarctation device.
Figure 43:
FIG. 43 depicts a fluorescent stain of the stroke penumbra in a rat brain section after placement of a coarctation device.

In stroke induced rat model using the method described in Example 1, 10 rats were used in a control group and 10 rats in a treatment group. In the control group (stroke but no coarctation) a fluorescent green dye was injected prior to sacrificing the animal as described above. A dramatic reduction in the number of patent capillaries is evident in the stroke center as depicted in FIG. 40 and in the stroke penumbra of the ipsilateral hemisphere as depicted in FIG. 41. In the rats treated with the coarctation devices, the fluorescent dye is injected after constriction of the aorta. No cerebral hemorrhages were noted microscopically in the stroke center or the surrounding tissue. The number of patent cerebral capillaries is clearly increased in the treated rats using the coarctation devices, evident in the stroke center as depicted in FIG. 42 and in the stroke penumbra as depicted in FIG. 43. A comparison of the stroke control using green dye, for which there were eight open blood vessels, to the group treated with coarctation, for which there were 20 open vessels, shows that coarctation opened more than 100% more capillaries. This example further demonstrates the efficacy of using the coarctation devices in improving cerebral blood flow for treatment of stroke.

EXAMPLE 3

Infarct Volume Reduction Using Coarctation Device

Using the TTC technique (technetium stain) to determine infarct (stroke) volume, one hour of treatment with a coarctation device inflated at the level of the kidneys, and started 90 minutes after the onset of stroke (induced by CCA and MCA occlusion plus occlusion of contralateral carotid artery plus occlude CCA on good side for one hour), reduced stroke volume at 24 hours from 1100 to 400. Thus, one hour of treatment achieved a 66% reduction in stroke volume. In certain animals, up to 80% reduction in stroke volume was achieved, and the stroke was not visible at low magnification. Thus, the devices and methods disclosed herein provide for a reduction in stroke volume of at least 60%, more preferably at least 70%, more preferably at least 80%, and most preferably greater than 80%.

EXAMPLE 4

Use of Coarctation Device in Dryden Dogs

Figure 2B:
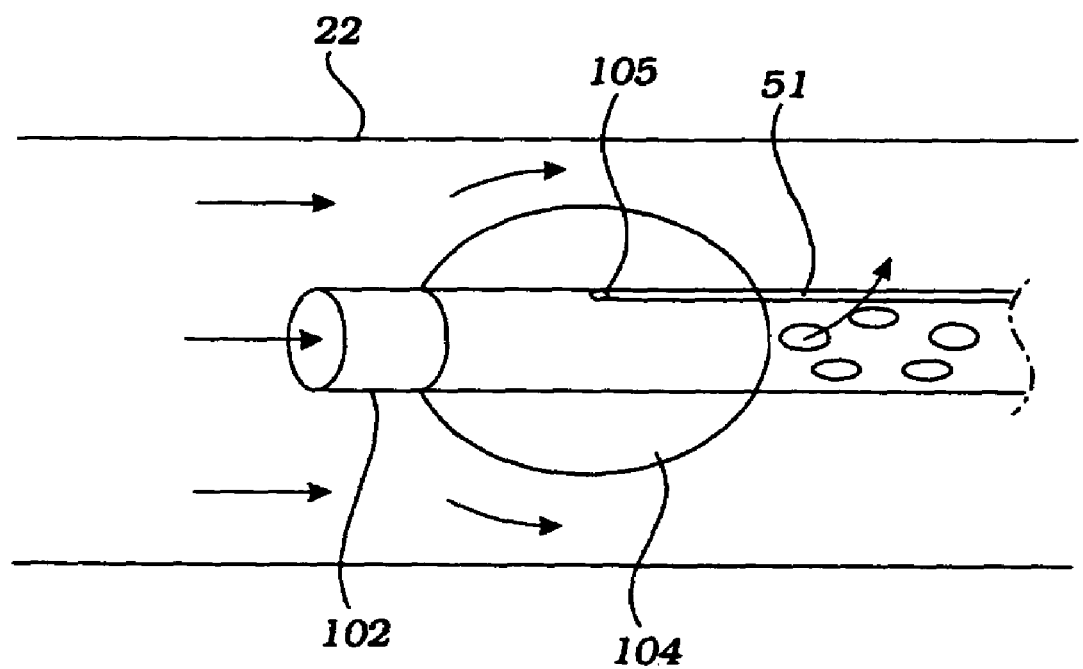
FIG. 2B illustrates another embodiment of the devices constructed according to the present invention for providing partial occlusion of a vessel.

A coarctation device as depicted in FIG. 2B, consisting of a balloon with a central passage allowing blood flow through it, was introduced transfemorally into the aorta. Correct placement was confirmed by fluoroscopy by injecting dye into balloon 104. An inflation of 1-3 cc provides incomplete occlusion, allowing blood passage through the center and around the edges of the device. At 4-5 cc inflation, blood only flows through the center of the device. Blood pressure above and below the device was recorded. The effect of the device in different positions (infrarenal, suprarenal, supracoeliac, and thoracic) on blood pressure was noted. The effect of changes in blood volume on pressure at different levels of constriction were examined (shock induced by hemorrhage). Infrarenally, 17-25% increased pressure was noted starting at 3 cc of inflation, which correlates with incomplete occlusion. This increase in pressure is sustainable. Suprarenally, 50-60% increased pressure was noted starting at 3 cc of inflation, which correlates with incomplete occlusion. This increase in pressure is sustainable. Further inflations either suprarenally or infrarenally will not increase blood pressure and cause bulging of the aorta outward.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for increasing cerebral blood flow, comprising the steps of:
   providing an elongate tubular member having a proximal end, a distal end, a lumen therebetween, and an elongate non-spherical balloon approximately 3-6 cm in length mounted on the distal end of the elongate tubular member and communicating with the lumen, the balloon having a compliance of approximately 0.3-1.25 mm per psi and configured such that it has an initial wrinkle-free diameter of approximately 10-15 mm, and thereafter expands upon inflation, and the elongated tubular member and the balloon being configured for placement in the descending aorta downstream from the takeoff of the brachiocephalic artery;
   inserting the elongate tubular member into the descending aorta;
   locating the balloon downstream from the takeoff of the brachiocephalic artery in the descending aorta; and
   expanding the balloon to at least partially obstruct blood flow in the descending aorta.

2. The method of claim 1, further comprising the step of measuring cerebral blood flow before the step of expanding the balloon to at least partially obstruct blood flow in the aorta.

3. The method of claim 2, further comprising the step of measuring cerebral blood flow after the step of expanding the balloon to at least partially obstruct blood flow in the aorta.

4. The method of claim 3, further comprising the step of adjusting the expansion of the balloon based on measured cerebral blood flow.

* * * * *